US012146883B2

(12) United States Patent
Cuero Rengifo et al.

(10) Patent No.: US 12,146,883 B2
(45) Date of Patent: Nov. 19, 2024

(54) GLUCOSE SENSORS AND METHODS OF USE THEREOF

(71) Applicant: BIOCAPITAL HOLDINGS, LLC, Houston, TX (US)

(72) Inventors: Raul Cuero Rengifo, Cypress, TX (US); Laura Sanchez Londono, Manizales (CO)

(73) Assignee: BIOCAPITAL HOLDINGS, LLC, Houston, TX (US)

( * ) Notice: Subject to any disclaimer, the term of this patent is extended or adjusted under 35 U.S.C. 154(b) by 631 days.

(21) Appl. No.: 17/311,106

(22) PCT Filed: Dec. 4, 2019

(86) PCT No.: PCT/US2019/064470
§ 371 (c)(1),
(2) Date: Jun. 4, 2021

(87) PCT Pub. No.: WO2020/117937
PCT Pub. Date: Jun. 11, 2020

(65) Prior Publication Data
US 2021/0382063 A1    Dec. 9, 2021

Related U.S. Application Data

(60) Provisional application No. 62/775,994, filed on Dec. 6, 2018.

(51) Int. Cl.
*G01N 33/66*    (2006.01)
*C07K 14/39*    (2006.01)
(Continued)

(52) U.S. Cl.
CPC ............. *G01N 33/66* (2013.01); *C07K 14/39* (2013.01); *C12N 9/1051* (2013.01);
(Continued)

(58) Field of Classification Search
CPC .. G01N 33/66; G01N 21/6428; G01N 33/582; G01N 2333/91148;
(Continued)

(56) References Cited

U.S. PATENT DOCUMENTS

2003/0096264 A1 * 5/2003 Altar ................... G01N 33/5023
435/6.16
2005/0130302 A1 * 6/2005 Nakauchi ............. C12N 5/0623
435/372

(Continued)

FOREIGN PATENT DOCUMENTS

WO    WO-2006026478 A2 *    3/2006    ............. A61K 38/45
WO    20120145459    10/2012
WO    WO-2017182634 A1 *    10/2017    ......... A61K 39/0011

OTHER PUBLICATIONS

Ma et al., Protein O-GlcNAcylation in diabetes and diabetic complications, Aug. 2013, Expert Rev Proteomics, 10(4):365-80. (Year: 2013).*

(Continued)

*Primary Examiner* — Soren Harward
*Assistant Examiner* — Naghmeh Nina Moazzami
(74) *Attorney, Agent, or Firm* — Thomas | Horstemeyer, LLP

(57) ABSTRACT

Described herein are glucose sensors. The sensors are composed of host cells incorporating DNA devices specifically designed to produce fluorescence when the cells come into contact with glucose from a patient sample. Once the fluorescence has been quantified, it can be correlated with the amount of glucose present in the sample. Also described herein are extracts from the host cells that can sense and measure glucose levels in a patient. The devices and extracts disclosed herein are inexpensive but sensitive and accurate enough for use in both home and clinical testing situations. The devices and extracts disclosed herein are also useful for (Continued)

diagnosis of diabetes, pre-diabetes, or other diseases associated with elevated glucose levels.

34 Claims, 2 Drawing Sheets

Specification includes a Sequence Listing.

(51) Int. Cl.
  *C12N 9/10* (2006.01)
  *C12N 9/24* (2006.01)
  *G01N 21/64* (2006.01)
(52) U.S. Cl.
  CPC .... *C12N 9/2402* (2013.01); *C12Y 204/01255* (2013.01); *C12Y 302/01031* (2013.01); *G01N 21/6428* (2013.01)
(58) Field of Classification Search
  CPC .. G01N 33/5023; C07K 14/39; C07K 14/395; C12N 9/1051; C12N 9/2402; C12N 15/81; C12Y 204/01255; C12Y 302/01031; C12Y 302/01169; C12Q 1/48
  See application file for complete search history.

(56) References Cited

U.S. PATENT DOCUMENTS

| | | | |
|---|---|---|---|
| 2010/0330594 A1 | 12/2010 | Hart et al. | |
| 2014/0287425 A1* | 9/2014 | Rengifo | C12Q 1/6897 435/254.2 |
| 2017/0166897 A1* | 6/2017 | Rubenstein | A61P 17/02 |

OTHER PUBLICATIONS

Arpino et al., Crystal Structure of Enhanced Green Fluorescent Protein to 1.35 Å Resolution Reveals Alternative Conformations for Glu222, 2012, PLoS One;7(10):e47132 (Year: 2012).*
Sinfield, O., Warwick (2014), p. 1-5. https://warwick.ac.uk/study/csde/gsp/eportfolio/directory/pg/lsujcw/gibsonguide/. (Year: 2014).*
Francis and Page, Strategies to Optimize Protein Expression in *E. coli.*, 2010, Current Protocols in Protein Science, 61: 5.24.1-5.24.29 (Year: 2010).*
Lubas et al., Functional Expression of O-linked GlcNAc Transferase, 2000, Jour of Biological Chem, vol. 275, No. 16, p. 10983-88 (Year: 2000).*
Li et al., Isoforms of Human O-GlcNAcase Show Distinct Catalytic Efficiencies, 2010, Biochemistry (Moscow), vol. 75, No. 7, p. 938-943 (Year: 2010).*
ThermoFisher Scientific and Invitrogen, YES Vector Collection, 2002, https://www.thermofisher.com/document-connect/document-connect.html?url=https://assets.thermofisher.com/TFS-Assets%2FLSG%2Fbrochures%2F710_021524_pyes_bro.pdf. (Year: 2002).*
AY039679, 2001, GenEmbl database. (Year: 2001).*
Kaletsky, et al. Transcriptome analysis of adult Caenorhabditis elegans cells reveals tissue-specific gene and soform expression. PLoS Genet vol. 14, No. 8, pp. e1007559; Abstract, p. 3, 18, 24; Supplementary Materials, S1 Table, entry 937, 1709, 5487.
Cuero, et al. Construct of DNA glucose sensor yeast plasmid for early detection of diabetes. Integrative Obesity and Diabetes 2017, vol. 3, No. 5, pp. 1-9; Abstract, p. 2, col. 2.
Nakanishi, et al. Yeast cells as an assay system for in vivo O-GlcNAc modification. Biochim Biophys Acta Gen Subj. 2017, vol. 1861, No. 5 Pt A, pp. 1159-1167; Abstract, p. 1163, col. 2 to p. 1164, col. 1.
International Search Report and Written Opinion for Application No. PCT/US2019/064470 mailed Feb. 28, 2020.

* cited by examiner

GLUCOSE SENSORS AND METHODS OF USE THEREOF

CROSS REFERENCE TO RELATED APPLICATIONS

This application claims priority upon U.S. provisional application Ser. No. 62/775,994 filed on Dec. 6, 2018. This application is hereby incorporated by reference in its entirety.

CROSS REFERENCE TO SEQUENCE LISTING

The genetic components described herein are referred to by a sequence identifier number (SEQ ID NO). The SEQ ID NO corresponds numerically to the sequence identifiers <400>1, <400>2, etc. The Sequence Listing, in written computer readable format (CRF) is hereby incorporated by reference in its entirety.

BACKGROUND

Diabetes is a degenerative disease caused by abnormal levels of glucose in the cell. These abnormal levels of glucose are not easily predictable and/or measurable. Current home use technologies to determine glucose levels in the blood are not always accurate and may not be able to determine extremely low levels of glucose (below 20 mg/dL). In type 1 diabetes, the body is unable to produce insulin. In type 2 diabetes, insulin is produced but the body destroys it or is unable to recognize it. Pre-diabetes, meanwhile, is a condition where blood glucose is higher than normal but not high enough to be considered type 2 diabetes. Prediabetes can often be addressed with lifestyle changes. Metabolic syndrome is a group of conditions occurring in the same individual including hypertension, high blood sugar, excess body fat around the waist, and high cholesterol. People with metabolic syndrome exhibit insulin resistance, as well.

Popular devices and methods for determining glucose levels employ enzyme reactions and use whole blood, plasma, or serum for samples. Enzymes used include glucose oxidase, hexokinase, and glucose dehydrogenase. The products of these enzymatic reactions and blood sugar can be determined using colorimetric or spectrophotometric assays, or by measuring electric current produced during the enzymatic reaction, as is the case for most commercially-available glucose meters. These methods can detect glucose in the range of 0-500 mg/dL for laboratory assays and 20-500 mg/dL for home assays and are becoming more sensitive, but falsely high readings can occur depending on environmental conditions and/or specific medical treatments a patient is undergoing. Use of home meters with incompatible strips as well as poor calibration of meters can also give unreliable results.

The cost of current methods for monitoring blood sugar levels is also an impediment and can range from $0.35 to $1 per test strip for home monitoring methods. Type 1 diabetics may test as often as four to ten times per day, making daily testing expensive. For clinical laboratories, glucose determinations can range from $3 to over $100 in the US and/or overseas. Diagnostic tests to detect the condition of diabetes in a previously-undiagnosed patient can range between $190 and $350. Furthermore, current methods require the use of lancing devices to generate blood samples; these devices can also be expensive and their use can cause pain in patients.

What is needed is an inexpensive and sensitive method to test glucose levels and diagnose diabetes and/or prediabetic conditions in patients. Ideally, the method would be non-invasive and not require the use of lancing devices.

SUMMARY

Described herein are glucose sensors. The sensors are composed of host cells incorporating DNA devices specifically designed to produce fluorescence when the cells come into contact with glucose from a patient sample. Once the fluorescence has been quantified, it can be correlated with the amount of glucose present in the sample. Also described herein are extracts from the host cells that can sense and measure glucose levels in a patient. The devices and extracts disclosed herein are inexpensive but sensitive and accurate enough for use in both home and clinical testing situations. The devices and extracts disclosed herein are also useful for diagnosis of diabetes, pre-diabetes, or other diseases associated with elevated glucose levels.

The advantages of the invention will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

DETAILED DESCRIPTION

Figure 1:
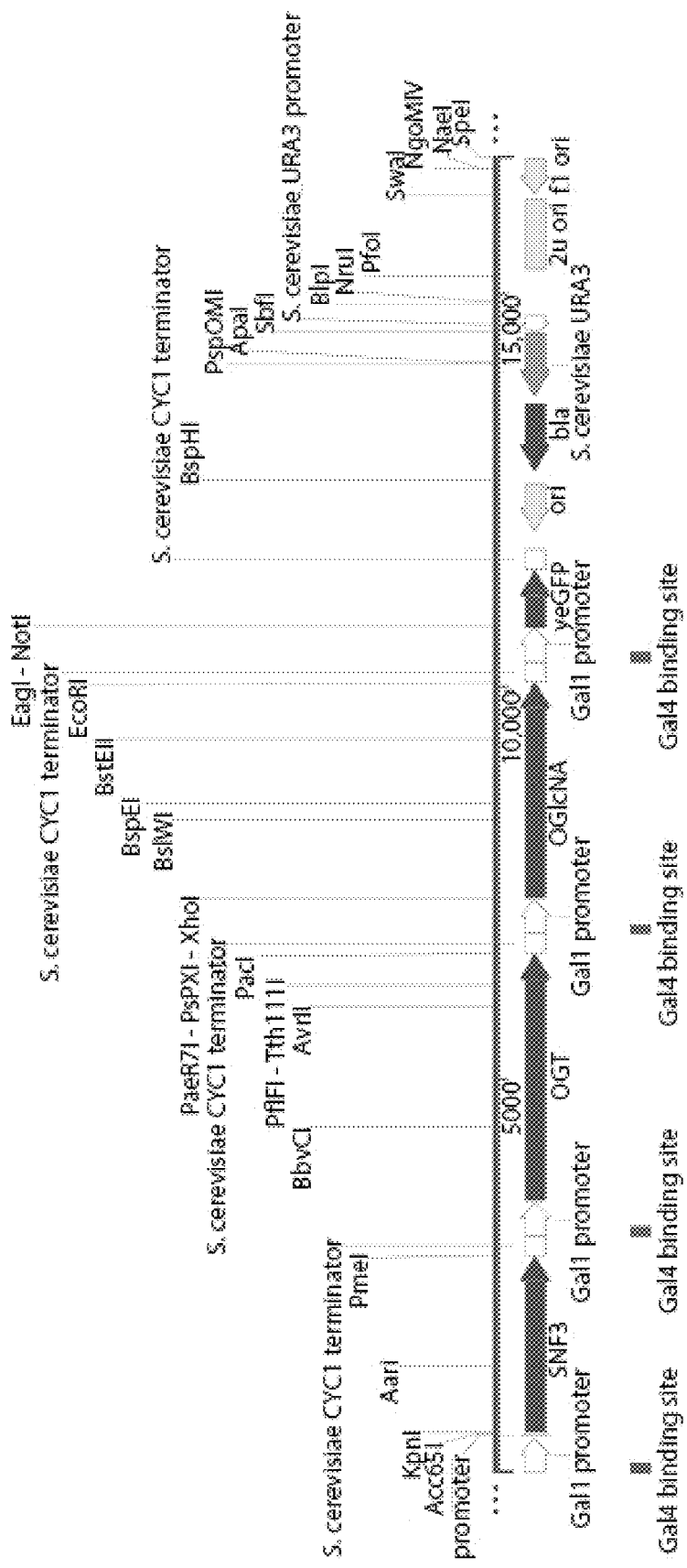
FIG. 1 shows a linear schematic of a vector described herein, wherein the vector has SEQ ID NO. 5.

Before the present compounds, compositions, articles, devices, and/or methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and appended claims, the singular forms "a," "an," and "the" include plural referents unless the context clearly dictates otherwise. Thus, for example, reference to "an isolated nucleic acid" includes mixtures of two or more such nucleic acids, and the like.

"Optional" or "optionally" means that the subsequently described event or circumstance can or cannot occur, and that the description includes instances where the event or circumstance occurs and instances where it does not. For example, the phrase "optionally includes a gene for a selective marker" means that the gene may or may not be present.

Throughout this specification, unless the context dictates otherwise, the word "comprise," or variations such as "comprises" or "comprising," will be understood to imply the inclusion of a stated element, integer, step, or group of elements, integers, or steps, but not the exclusion of any other element, integer, step, or group of elements, integers, or steps.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

Disclosed are materials and components that can be used for, can be used in conjunction with, can be used in preparation for, or are products of the disclosed compositions and methods. These and other materials are disclosed herein, and it is understood that when combinations, subsets, interactions, groups, etc. of these materials are disclosed that while specific reference of each various individual and collective combination and permutation of these compounds may not be explicitly disclosed, each is specifically contemplated and described herein. For example, if a yeast is disclosed and discussed and a number of different compatible yeast plasmids are discussed, each and every combination and permutation of yeast and yeast plasmid that is possible is specifically contemplated unless specifically indicated to the contrary. For example, if a class of molecules A, B, and C are disclosed as well as a class of molecules D, E, and F, and an example of a combination molecule A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E is specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if a variety of additional steps can be performed, it is understood that each of these additional steps can be performed with any specific embodiment or combination of embodiments of the disclosed methods, and that each such combination is specifically contemplated and should be considered disclosed.

References in the specification and concluding claims to parts by weight, of a particular element or component in a composition or article, denote the weight relationship between the element or component and any other elements or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

I. DNA Constructs

DNA constructs are provided herein for the production of SNF3, O-linked N-acetylglucosamine transferase (OGT), and O-linked N-acetylglucosamine-selective-N-acetyl-β-D-glucosaminidase (OGlcNa) for the production of devices and extracts that can be used to measure glucose levels in a patient sample. It is understood that one way to define the variants and derivatives of the genetic components and DNA constructs described herein is in terms of homology/identity to specific known sequences. Those of skill in the art readily understand how to determine the homology of two nucleic acids. For example, the homology can be calculated after aligning the two sequences so that the homology is at its highest level. Another way of calculating homology can be performed according to published algorithms (see Zuker, M., *Science*, 244:48-52, 1989; Jaeger et al., *Proc. Natl. Acad. Sci. USA*, 86:7706-7710, 1989; and Jaeger et al., *Methods Enzymol.*, 183:281-306, 1989, which are herein incorporated by reference for at least material related to nucleic acid alignment).

As used herein, "conservative" mutations are mutations that result in an amino acid change in the protein produced from a sequence of DNA. When a conservative mutation occurs, the new amino acid has similar properties as the wild type amino acid and generally does not drastically change the function or folding of the protein (e.g., switching isoleucine for valine is a conservative mutation since both are small, branched, hydrophobic amino acids). "Silent mutations," meanwhile, change the nucleic acid sequence of a gene encoding a protein but do not change the amino acid sequence of the protein.

It is understood that the description of mutations and homology can be combined together in any combination, such as embodiments that have at least 70%, 75%, 80%, 85%, 90%, 95%, or 99% homology to a particular sequence wherein the variants are conservative or silent mutations. It is understood that any of the sequences described herein can be a variant or derivative having the homology values listed above.

In one aspect, a database such as, for example, GenBank, can be used to determine the sequences of genes and/or regulatory regions of interest, the species from which these elements originate, and related homologous sequences.

In one aspect, genes of interest can be incorporated into a DNA construct. In a further aspect, the DNA construct can be incorporated as part of a vector for transfection into microbial cells. In a still further aspect, the vector can be a plasmid, a phagemid, a cosmid, a yeast artificial chromosome, a bacterial artificial chromosome, a virus, a phage, or a transposon. In another aspect, the microorganisms are fungi or bacteria. In one aspect, the fungi are yeasts such as, for example, *Saccharomyces cerevisiae*. In another aspect, the bacteria are *Escherichia coli*.

Vectors capable of high levels of expression of recombinant genes and proteins are well known in the art. Vectors useful for the transformation of a variety of host cells are common and commercially available and include, for example, pWLneo, pSV2cat, pOG44, pXT1, pSG, pSVK3, pBSK, pBR322, pYES, pYES2, pBSKII, pUC, and pET-Duet-1. The skilled practitioner will be able to choose a plasmid based on such factors as (a) the amount of nucleic acid (i.e., number of genes and other elements) to be inserted, (b) the host organism, (c) culture conditions for the host organism, and other related factors.

In one aspect, the DNA construct includes the following genetic components: (a) a gene that expresses SNF3, (b) a gene that expresses OGT, and (c) a gene that expresses OGlcNA.

In one aspect, the nucleic acids (e.g., genes that express the SNF3, OGT, and OGlcNA) used in the DNA constructs described herein can be amplified using polymerase chain reaction (PCR) prior to being ligated into a plasmid or other vector. Typically, PCR amplification techniques make use of primers, or short, chemically-synthesized oligonucleotides that are complementary to regions on each respective strand flanking the DNA or nucleotide sequence to be amplified. A person having ordinary skill in the art will be able to design or choose primers based on the desired experimental conditions. In general, primers should be designed to provide for both efficient and faithful replication of the target nucleic acids. Two primers are required for the amplification of each gene, one for the sense strand (that is, the strand containing the gene of interest) and one for the antisense strand (that is, the strand complementary to the gene of interest). Pairs of primers should have similar melting temperatures that are close to the PCR reaction's annealing temperature. In order to facilitate the PCR reaction, the following features should be avoided in primers: mononucleotide repeats, complementarity with other primers in the mixture, self-complementarity, and internal hairpins and/or loops. Methods of primer design are known in the art; additionally, computer programs exist that can assist the skilled practitioner with primer design. Primers can optionally incorporate restriction enzyme recognition sites at their 5' ends to assist in later ligation into plasmids or other vectors.

PCR can be carried out using purified DNA, unpurified DNA that is integrated into a vector, or unpurified genomic DNA. The process for amplifying target DNA using PCR consists of introducing an excess of two primers having the characteristics described above to a mixture containing the sequence to be amplified, followed by a series of thermal cycles in the presence of a heat-tolerant or thermophilic DNA polymerase, such as, for example, any of Taq, Pfu, Pwo, Tfl, rTth, Tli, or Tma polymerases. A PCR "cycle" involves denaturation of the DNA through heating, followed by annealing of the primers to the target DNA, followed by extension of the primers using the thermophilic DNA polymerase and a supply of deoxynucleotide triphosphates (i.e., dCTP, dATP, dGTP, and TTP), along with buffers, salts, and other reagents as needed. In one aspect, the DNA segments created by primer extension during the PCR process can serve as templates for additional PCR cycles. Many PCR cycles can be performed to generate a large concentration of target DNA or gene. PCR can optionally be performed in a device or machine with programmable temperature cycles for denaturation, annealing, and extension steps. Further, PCR can be performed on multiple genes simultaneously in the same reaction vessel or microcentrifuge tube since the primers chosen will be specific to selected genes. PCR products can be purified by techniques known in the art such as, for example, gel electrophoresis followed by extraction from the gel using commercial kits and reagents.

In a further aspect, the plasmid can include an origin of replication, allowing it to use the host cell's replication machinery to create copies of itself.

As used herein, "operably linked" refers to the association of nucleic acid sequences on a single nucleic acid fragment so that the function of one affects the function of another. For example, if sequences for multiple genes are inserted into a single plasmid, their expression may be operably linked. Alternatively, a promoter is said to be operably linked with a coding sequence when it is capable of affecting the expression of that coding sequence.

As used herein, "expression" refers to transcription and/or accumulation of an mRNA derived from a gene or DNA fragment. Expression may also be used to refer to translation of mRNA into a peptide, polypeptide, or protein.

In one aspect, disclosed herein are biological devices incorporating a gene that expresses SNF3. Without wishing to be bound by theory, SNF3 is a protein from yeasts and other organisms that has a high affinity glucose in the environment and that is further involved in glucose uptake; glucose at low concentrations stimulates SNF3 to regulate activity of genes encoding glucose transporters. In one aspect, SNF3 is a plasma membrane protein with a long C-terminal tail that extends into the cytoplasm. In some aspects, SNF3 may also respond to the presence of galactose in the environment.

In one aspect, the gene that expresses SNF3 is isolated from *Pichia stipitis* (also known as *Scheffersomyces stipitis*) and can be found in GenBank with GI number XM_0013863691 In a further aspect, the gene that expresses SNF3 has SEQ ID NO. 1 or at least 70% homology thereto, at least 75% homology thereto, at least 80% homology thereto, at least 85% homology thereto, at least 90% homology thereto, or at least 95% homology thereto. In one aspect, the gene that expresses SNF3 is isolated from a yeast of one of the following genera: *Babjeviella, Candida, Clavispora, Cyberlindnera, Debaryomyces, Hyphopichia, Kazachstania, Komagataella, Kuraishia, Lachancea, Lodderomyces, Metschnikowia, Meyerosyma, Naumovozyma, Pichia, Saccharomyces, Saccharomycetaceae, Saccharomycopsis, Scheffersomyces, Spathaspora, Vanderwaltozyma*, or *Wickerhamomyces*. In another aspect, the gene that expresses SNF3 is isolated from one of the following strains of *Saccharomyces cerevisiae*: Y169, X55, KSD-Yc, SY14, BY4742, CEN.PK113-7D, YPS128, Y12, SK1, DBVPG6044, S288c, YJM1381, YJM1549, YJM1401, YJM1304, YJM1190, YJM1400, YJM1355, YJM1273, T63, HB S BILANCHER, HB C OMARUNUI, WA C MATES, WA C WAITAKEREROAD, T.52 5A, WA C KINGSMILL, WA C MATES, T78, HCNTHsf, T52.2H, T52.3C, YJM1439, YJM1342, YJM1479, YJM1434, YJM1389, YJM1388, YJM1248, or NSERVsf. In still another aspect, the gene that expresses SNF3 is isolated from one of the following strains of *Candida albicans*: SC5314-P0 or SC5314-GTH12. In an alternative aspect, the gene that expresses SNF3 is isolated from a plant such as, for example, *Hordeum vulgare* or *Arabidopsis thaliana*. In an alternative aspect, the gene that expresses SNF3 is isolated from a mammal such as, for example, a mouse. In still another aspect, the gene that expresses SNF3 has SEQ ID NO. 6, 7, 8, 9, 10, 11, 12, 13, 14, or 15.

Other sequences expressing SNF3 or related or homologous genes can be identified in a database such as, for example, GenBank. In one aspect, sequences useful herein include those with the GI numbers listed in Table 1.

TABLE 1

| SNF3 Genes | | |
|---|---|---|
| Source Organism | Sequence Description | GI Number |
| *Scheffersomyces stipitis* | high-affinity glucose transporter SNF3 | XM_001386379.1 |
| *Scheffersomyces stipitis* | chromosome 8 sequence | CP000502.1 |
| *Candida tanzawaensis* | general substrate transporter | XM_020208803.1 |

TABLE 1-continued

SNF3 Genes

| Source Organism | Sequence Description | GI Number |
|---|---|---|
| *Spathaspora passalidarum* | hypothetical protein | XM_007376130.1 |
| *Debaryomyces hansenii* | chromosome B sequence | CR382134.2 |
| *Debaryomyces hansenii* | genomic DNA | XM_457565.1 |
| *Debaryomyces fabryi* | hypothetical protein | XM_015611621.1 |
| *Candida orthopsilosis* | glucose and galactose sensor | XM_003868724.1 |
| *Candida orthopsilosis* | chromosome 3 sequence | HE681721.1 |
| *Meyerosyma guilliermondii* | hypothetical protein | XM_001486109.1 |
| *Candida dubliniensis* | glucose sensor (putative) | XM_002419355.1 |
| *Candida dubliniensis* | chromosome 3 sequence | FM992690.1 |
| *Metschnikowia bicuspidata* | hypothetical protein | XM_018856772.1 |
| *Candida parapsilosis* | genomic DNA | HE605208.1 |
| *Candida auris* | hypothetical protein | XM_018315448.1 |
| *Lodderomyces elongisporus* | hypothetical protein | XM_001526242.1 |
| *Candida pseudohaemutonii* | hypothetical protein | XM_024859329.1 |
| *Candida duobushaemulonis* | hypothetical protein | XM_025483142.1 |
| *Candida albicans* | chromosome 3 sequence | CP032018.1 |
| *Candida viswanathii* | high-affinity glucose transporter SNF3 | XM_026737497.1 |
| *Candida albicans* | chromosome 3B sequence | CP025160.1 |
| *Candida albicans* | chromosome 3A sequence | CP025152.1 |
| *Candida albicans* | chromosome 3B sequence | CP025177.1 |
| *Candida albicans* | chromosome 3A sequence | CP025169.1 |
| *Candida albicans* | chromosome 3 sequence | CP017625.1 |
| *Candida albicans* | glucose sensor | XM_718080.1 |
| *Candida tenuis* | hypothetical protein | XM_006688525.1 |
| *Clavispora lusitaniae* | hypothetical protein | XM_002618452.1 |
| *Candida viswanathii* | high-affinity glucose transporter SNF3 | XM_026731331.1 |
| *Candida haemulonis* | hypothetical protein | XM_025488849.1 |
| *Candida tropicalis* | hypothetical protein | XM_002547995.1 |
| *Hyphopichia burtonii* | general substrate transporter SNF3 | XM_020218846.1 |
| *Candida intermedia* | chromosome II sequence | LT635765.1 |
| *Candida intermedia* | chromosome II sequence | LT635757.1 |
| *Pichia sorbitophila* | chromosome C sequence | FO082057.1 |
| *Pichia sorbitophila* | chromosome D sequence | FO082056.1 |
| Saccharomycetaceae sp. "Ashbya aceri" | chromosome IV sequence | CP006023.1 |
| *Cyberlindnera fabianii* | genomic DNA | LK052888.1 |
| *Saccharomyces kudriavzevii* | chromosome IV sequence | CP030965.1 |
| *Lachancea lanzarotensis* | genomic DNA | XM_022772444.1 |
| *Wickerhamomyces ciferrii* | high-affinity glucose transporter | XM_011278392.1 |
| *Wickerhamomyces anomalus* | hypothetical protein | XM_019182027.1 |
| *Babjeviella inositovora* | hypothetical protein | XM_019129516.1 |
| *Lachancea thermotolerans* | genomic DNA | XM_002555927.1 |
| *Lachancea thermotolerans* | chromosome H sequence | CU928180.1 |
| *Saccharomyces jurei* | chromosome IV sequence | LT986465.1 |
| *Naumovozyma castellii* | hypothetical protein | XM_003676753.1 |
| *Naumovozyma castellii* | chromosome 5 sequence | HE576756.1 |
| *Kuraishia capsulate* | uncharacterized protein | XM_022605974.1 |
| *Kazachstania naganishii* | hypothetical protein | XM_022611574.1 |
| *Saccharomyces paradoxus* | chromosome IV sequence | CP020313.1 |
| *Kazachstania naganishii* | chromosome 2 sequence | HE978315.1 |
| *Saccharomycopsis fibuligera* | chromosome B5 sequence | CP012820.1 |
| *Vanderwaltozyma polyspora* | hypothetical protein | XM_001643718.1 |
| *Saccharomyces eubayanus* | chromosome IV sequence | CP030948.1 |
| *Saccharomyces eubayanus* | SNF3-like protein | XM_018364102.1 |
| *Saccharomyces cerevisiae* | chromosome 4 sequence | CP033473.1 |
| *Saccharomyces cerevisiae* | chromosome 4 sequence | CP033490.1 |
| *Saccharomyces cerevisiae* | chromosome 4 sequence | CP023998.1 |
| *Saccharomyces cerevisiae* | chromosome I sequence | CP029160.1 |
| *Saccharomyces cerevisiae* | chromosome IV sequence | CP026298.1 |
| *Saccharomyces cerevisiae* | chromosome IV sequence | CP022969.1 |
| *Komagataella phaffii* | chromosome 1 sequence | LT962476.1 |
| *Saccharomyces cerevisiae* | chromosome IV sequence | CP020211.1 |
| *Saccharomyces cerevisiae* | chromosome IV sequence | CP020194.1 |
| *Saccharomyces cerevisiae* | chromosome IV sequence | CP020177.1 |
| *Saccharomyces cerevisiae* | chromosome IV sequence | CP020143.1 |
| *Saccharomyces cerevisiae* | chromosome IV sequence | CP020126.1 |
| *Saccharomyces cerevisiae* | chromosome IV sequence | CP004718.2 |
| *Pichia membranifaciens* | hypothetical protein | XM_019160717.1 |
| *Saccharomyces cerevisiae* | chromosome IV sequence | CP004747.2 |
| *Saccharomyces cerevisiae* | chromosome IV sequence | CP004727.2 |
| *Saccharomyces cerevisiae* | chromosome IV sequence | CP004707.2 |
| *Saccharomyces cerevisiae* | chromosome IV sequence | CP004697.2 |

TABLE 1-continued

SNF3 Genes

| Source Organism | Sequence Description | GI Number |
|---|---|---|
| Komagataella phaffii | chromosome 1 sequence | CP014715.1 |
| Komagataella phaffii | chromosome 1 sequence | CP014708.1 |
| Saccharomyces cerevisiae | chromosome IV sequence | CP004726.2 |
| Saccharomyces cerevisiae | chromosome IV sequence | CP004716.2 |
| Saccharomyces cerevisiae | chromosome IV sequence | CP004706.2 |
| Saccharomyces cerevisiae | chromosome IV sequence | CP008307.1 |
| Saccharomyces cerevisiae | chromosome IV sequence | CP008273.1 |
| Saccharomyces cerevisiae | chromosome IV sequence | CP008426.1 |
| Saccharomyces cerevisiae | chromosome IV sequence | CP008579.1 |
| Saccharomyces cerevisiae | chromosome IV sequence | CP008562.1 |
| Saccharomyces cerevisiae | chromosome IV sequence | CP008664.1 |
| Saccharomyces cerevisiae | chromosome IV sequence | CP008613.1 |
| Saccharomyces cerevisiae | chromosome IV sequence | CP008596.1 |
| Saccharomyces cerevisiae | chromosome IV sequence | CP007950.1 |
| Saccharomyces cerevisiae | chromosome IV sequence | CP007933.1 |
| Saccharomyces cerevisiae | chromosome IV sequence | CP007848.1 |
| Saccharomyces cerevisiae | chromosome IV sequence | CP007814.1 |
| Saccharomyces cerevisiae | chromosome IV sequence | CP004735.2 |
| Saccharomyces cerevisiae | chromosome IV sequence | CP004715.2 |
| Saccharomyces cerevisiae | chromosome IV sequence | CP004744.2 |
| Saccharomyces cerevisiae | chromosome IV sequence | CP004734.2 |
| Saccharomyces cerevisiae | chromosome IV sequence | CP004724.2 |
| Saccharomyces cerevisiae | chromosome IV sequence | CP004723.2 |
| Saccharomyces cerevisiae | chromosome IV sequence | CP004703.2 |
| Saccharomyces cerevisiae | chromosome IV sequence | CP008290.1 |
| Saccharomyces cerevisiae | chromosome IV sequence | CP007899.1 |

In one aspect, disclosed herein are biological devices incorporating a gene that expresses OGT, also known as O-linked N-acetylglucosamine transferase, O-GlcNAc transferase, and UDP-N-acetylglucosamine-peptide N-acetylglucosaminyltransferase. Without wishing to be bound by theory, OGT is a protein from a variety of organisms including birds, primates, rodents, carnivores, and other mammals that catalyzes the addition of a single N-acetylglucosamine to serine or threonine residues of intracellular proteins through an O-glycosidic linkage. OGT activity may compete with phosphorylation and reaction rate and specificity may be affected by steric and/or electrostatic effects or protein conformation and residue accessibility. OGT activity is implicated in a variety of functions in humans and animals. In one aspect, OGT is involved in insulin resistance in muscle and fat cells.

In one aspect, the gene that expresses OGT is isolated from Urocitellys parryii (commonly known as the arctic ground squirrel) and can be found in GenBank with GI number XM_02651267.1. In a further aspect, the gene that expresses OGT has SEQ ID NO. 2 or at least 70% homology thereto, at least 75% homology thereto, at least 80% homology thereto, at least 85% homology thereto, at least 90% homology thereto, or at least 95% homology thereto. In another aspect, the gene that expresses OGT is isolated from a human, a domestic or wild mammal, or a bird. In still another aspect, the gene that expresses OGT is isolated from a arctic ground squirrel, thirteen-lined ground squirrel, water buffalo, wild yak, grizzly bear, domestic cow, olive baboon, polar bear, gelada, sooty mangabey, drill, mountain lion, giant panda, crab-eating macaque, Angola colobus, domestic goat, rhesus macaque, domestic sheep, mouflon, southern pig-tailed macaque, golden snub-nosed monkey, alpine marmot, dingo, domestic horse, domestic dog, green monkey, domestic cat, white-tailed deer, leopard, European rabbit, red fox, Sumatran orangutan, gorilla, Siberian tiger, common marmoset, Weddell seal, Tibetan antelope, common chimpanzee, donkey, bonobo, human, aardvark, beluga whale, society finch white rhinoceros, gray mouse lemur, or black-capped squirrel monkey.

Other sequences expressing OGT or related or homologous genes can be identified in a database such as, for example, GenBank. In one aspect, sequences useful herein include those with the GI numbers listed in Table 2.

TABLE 2

OGT Genes

| Source Organism | Sequence Description | GI Number |
|---|---|---|
| Urocitellus parryii | O-linked N-acetylglucosamine transferase | XM_026412627.1 |
| Urocitellus parryii | O-linked N-acetylglucosamine transferase | XM_026412628.1 |
| Ictidomys tridecemlineatus | O-linked N-acetylglucosamine transferase | XM_021719915.1 |
| Ictidomys tridecemlineatus | O-linked N-acetylglucosamine transferase | XM_005339941.2 |
| Ictidomys tridecemlineatus | O-linked N-acetylglucosamine transferase | XM_005339942.2 |
| Bubalus bubalis | O-linked N-acetylglucosamine transferase | XM_006050820.2 |
| Bos mutus | O-linked N-acetylglucosamine transferase | XM_005900810.2 |
| Bubalus bubalis | O-linked N-acetylglucosamine transferase | NM_001290907.1 |
| Bos mutus | O-linked N-acetylglucosamine transferase | XM_005900811.2 |
| Ursus arctos horribilis | O-linked N-acetylglucosamine transferase | XM_026485785.1 |
| Bos taurus | O-linked N-acetylglucosamine transferase | XM_005228027.4 |
| Papio anubis | O-linked N-acetylglucosamine transferase | XM_003917862.3 |

TABLE 2-continued

OGT Genes

| Source Organism | Sequence Description | GI Number |
|---|---|---|
| Ursus maritimus | O-linked N-acetylglucosamine transferase | XM_008712243.1 |
| Ursus arctos horribilis | O-linked N-acetylglucosamine transferase | XM_026485786.1 |
| Papio anubis | O-linked N-acetylglucosamine transferase | XM_003917863.4 |
| Ursus maritimus | O-linked N-acetylglucosamine transferase | XM_008712244.1 |
| Bos taurus | O-linked N-acetylglucosamine transferase | NM_001098070.2 |
| Bos taurus | O-linked N-acetylglucosamine transferase | BC140542.1 |
| Theropithecus gelada | O-linked N-acetylglucosamine transferase | XM_025371879.1 |
| Cercocebus atys | O-linked N-acetylglucosamine transferase | XM_012060760.1 |
| Theropithecus gelada | O-linked N-acetylglucosamine transferase | XM_025371880.1 |
| Cercocebus atys | O-linked N-acetylglucosamine transferase | XM_012060761.1 |
| Mandrillus leucophaeus | O-linked N-acetylglucosamine transferase | XM_011992070.1 |
| Mandrillus leucophaeus | O-linked N-acetylglucosamine transferase | XM_011992071.1 |
| Puma concolor | O-linked N-acetylglucosamine transferase | XM_025933892.1 |
| Ailuropoda melanoleuca | O-linked N-acetylglucosamine transferase | XM_002930577.3 |
| Macaca fascicularis | O-linked N-acetylglucosamine transferase | XM_005593919.1 |
| Colobus angolensis palliatus | O-linked N-acetylglucosamine transferase | XM_011943084.1 |
| Puma concolor | O-linked N-acetylglucosamine transferase | XM_025933893.1 |
| Ailuropoda melanoleuca | O-linked N-acetylglucosamine transferase | XM_002930576.3 |
| Macaca fascicularis | O-linked N-acetylglucosamine transferase | XM_005593920.2 |
| Capra hircus | O-linked N-acetylglucosamine transferase | XM_013976396.2 |
| Macaca mulatta | O-linked N-acetylglucosamine transferase | XM_015127666.1 |
| Ovis aries | O-linked N-acetylglucosamine transferase | XM_004022178.3 |
| Ovis aries musimon | O-linked N-acetylglucosamine transferase | XM_012142301.2 |
| Macaca nemestrina | O-linked N-acetylglucosamine transferase | XM_011732741.1 |
| Colobus angolensis palliatus | O-linked N-acetylglucosamine transferase | XM_011943085.1 |
| Rhinopithecus roxellana | O-linked N-acetylglucosamine transferase | XM_010366585.1 |
| Macaca nemestrina | O-linked N-acetylglucosamine transferase | XM_011732742.2 |
| Capra hircus | O-linked N-acetylglucosamine transferase | XM_013976398.2 |
| Marmota marmota marmota | UDP-N-acetylglucosamine-peptide N-acetylglucosaminetransferase | XR 001502441.1 |
| Macaca mulatta | O-linked N-acetylglucosamine transferase | XM_015127667.1 |
| Ovis aries | O-linked N-acetylglucosamine transferase | XM_004022177.3 |
| Ovis aries musimon | O-linked N-acetylglucosamine transferase | XM_012142302.2 |
| Canis lupus dingo | O-linked N-acetylglucosamine transferase | XM_025466166.1 |
| Equus caballus | O-linked N-acetylglucosamine transferase | XM_001493372.5 |
| Canis lupus familiaris | O-linked N-acetylglucosamine transferase | XM_844299.5 |
| Rhinopithecus roxellana | O-linked N-acetylglucosamine transferase | XM_010366586.1 |
| Chlorocebus sabaeus | O-linked N-acetylglucosamine transferase | XM_007992035.1 |
| Canis lupus dingo | O-linked N-acetylglucosamine transferase | XM_025466167.1 |
| Canis lupus familiaris | O-linked N-acetylglucosamine transferase | XM_538075.6 |
| Chlorocebus sabaeus | O-linked N-acetylglucosamine transferase | XM_007992036.1 |
| Equus caballus | O-linked N-acetylglucosamine transferase | XM_005614262.3 |
| Felis catus | O-linked N-acetylglucosamine transferase | XM_004000621.5 |
| Odocoileus virgianus texanus | O-linked N-acetylglucosamine transferase | XM_020882917.1 |
| Odocoileus virgianus texanus | O-linked N-acetylglucosamine transferase | XM_020882916.1 |
| Panthera pardus | O-linked N-acetylglucosamine transferase | XM_019428710.1 |
| Oryctolagus cuniculus | O-linked N-acetylglucosamine transferase | XM_002720103.3 |
| Equus caballus | O-linked N-acetylglucosamine transferase | XM_001493388.5 |
| Felix catus | O-linked N-acetylglucosamine transferase | XM_004000622.5 |
| Odocoileus virgianus texanus | O-linked N-acetylglucosamine transferase | XM_020882919.1 |
| Odocoileus virgianus texanus | O-linked N-acetylglucosamine transferase | XM_020882918.1 |
| Panthera pardus | O-linked N-acetylglucosamine transferase | XM_019428712.1 |
| Oryctolagus cuniculus | O-linked N-acetylglucosamine transferase | XM_002720102.3 |
| Vulpes vulpes | O-linked N-acetylglucosamine transferase | XM_025982889.1 |
| Pongo abelii | O-linked N-acetylglucosamine transferase | XM_024240358.1 |
| Gorilla gorilla gorilla | O-linked N-acetylglucosamine transferase | XM_004064365.2 |
| Panthera tigris altaica | O-linked N-acetylglucosamine transferase | XM_007089115.2 |
| Callithrix jacchus | O-linked N-acetylglucosamine transferase | XM_002762977.2 |
| Leptonychotes weddellii | O-linked N-acetylglucosamine transferase | XM_006749440.1 |
| Pantholops hodgsonii | O-linked N-acetylglucosamine transferase | XM_005954790.1 |
| Vulpes vulpes | O-linked N-acetylglucosamine transferase | XM_025982890.1 |
| Pongo abelii | O-linked N-acetylglucosamine transferase | XM_024240359.1 |
| Gorilla gorilla gorilla | O-linked N-acetylglucosamine transferase | XM_004064366.2 |
| Callithrix jacchus | O-linked N-acetylglucosamine transferase | XM_002762978.3 |
| Panthera tigris altaica | O-linked N-acetylglucosamine transferase | XM_007089116.2 |
| Leptonychotes weddellii | O-linked N-acetylglucosamine transferase | XM_006749441.1 |
| Pantholops hodgsonii | O-linked N-acetylglucosamine transferase | XM_005954791.1 |
| Pan troglodytes | O-linked N-acetylglucosamine transferase | XM_016943032.2 |
| Equus asinus | O-linked N-acetylglucosamine transferase | XM_014837684.1 |
| Pan paniscus | O-linked N-acetylglucosamine transferase | XM_003820131.2 |
| Homo sapiens | genomic DNA | AL833085.2 |
| Pan troglodytes | O-linked N-acetylglucosamine transferase | XM_016943033.1 |
| Pan paniscus | O-linked N-acetylglucosamine transferase | XM_003820132.2 |
| Equus asinus | O-linked N-acetylglucosamine transferase | XM_014837686.1 |
| Orycteropus afer afer | O-linked N-acetylglucosamine transferase | XM_007959000.1 |
| Homo sapiens | O-linked N-acetylglucosamine transferase | NM_181672.2 |

TABLE 2-continued

OGT Genes

| Source Organism | Sequence Description | GI Number |
| --- | --- | --- |
| Pongo abelii | O-linked N-acetylglucosamine transferase | NM_001133824.1 |
| Homo sapiens | genomic DNA | BX537844.1 |
| Homo sapiens | O-linked N-acetylglucosamine transferase | BC038180.1 |
| Equus asinus | O-linked N-acetylglucosamine transferase | XM_014837685.1 |
| Orycteropus afer afer | O-linked N-acetylglucosamine transferase | XM_007959001.1 |
| Homo sapiens | O-linked N-acetylglucosamine transferase | NM_181673.2 |
| Homo sapiens | O-linked N-acetylglucosamine transferase | BC014434.1 |
| Delphinapterus leucas | O-linked N-acetylglucosamine transferase | XM_022560995.1 |
| Lonchura striata domestica | O-linked N-acetylglucosamine transferase | XM_021534535.1 |
| Ceratotherium simum simum | O-linked N-acetylglucosamine transferase | XM_014794874.1 |
| Ceratotherium simum simum | O-linked N-acetylglucosamine transferase | XM_004439842.2 |
| Microcebus murinus | O-linked N-acetylglucosamine transferase | XM_012736183.1 |
| Saimiri boliviensis boliviensis | O-linked N-acetylglucosamine transferase | XM_003943099.2 |

In one aspect, disclosed herein are biological devices incorporating a gene that expresses OGlcNA, also known as O-GlcNAcase or O-GlcNAc-selective-N-acetyl-β-D-glucosaminidase, where GlcNAc is N-acetyl glucosamine and the prefix "O" indicates a linkage to a protein through an oxygen atom in an amino acid side chain. Without wishing to be bound by theory, glucosamine-induced insulin resistance is associated with an increase in or excess of proteins modified with O-GlcNAc residues, although O-GlcNAc modification is a common (though transient) post-translational modification of many cytoplasmic proteins. The gene encoding OGlcNA is also known as MEGA5 or meningioma expressed antigen 5 (hyaluronidase) and some variants in this gene are associated with an increased risk or precedence of type 2 diabetes in human populations.

In one aspect, the gene that expresses OGlcNA is isolated from *Rattus norvegicus* (commonly known as the brown rat) and can be found in GenBank with GI number NM_131904.1. In a further aspect, the gene that expresses OGlcNA has SEQ ID NO. 3 or at least 70% homology thereto, at least 75% homology thereto, at least 80% homology thereto, at least 85% homology thereto, at least 90% homology thereto, or at least 95% homology thereto. In another aspect, the gene that expresses OGlcNA is isolated from a rodent, carnivorous mammal, shrew, cetacean, pinniped, marsupial, primate, or other mammal. In still another aspect, the gene that expresses OGlcNA is isolated from a brown rat, alpine marmot, wild boar, arctic ground squirrel, thirteen-lined ground squirrel, domestic horse, Przewalski's horse, house mouse, European hedgehog, leopard, white rhinoceros, sea otter, Ord's kangaroo rat, North American beaver, Ryukyu mouse, Siberian tiger, Chinese tree shrew, cheetah, donkey, ferret, Gairdner's shrewmouse, naked mole-rat, domestic cat, Mongolian gerbil, beluga whale, olive baboon, Coquerel's sifaka, common bottlenose dolphin, Egyptian fruit bat, minke whale, gelada, Chinese rufous horseshoe bat, orca, dingo, northern fur seal, domestic dog, Sunda pangolin, common vampire bat, Pacific white-sided dolphin, gorilla, Sumatran orangutan, sperm whale, Ugandan red colobus, black snub-nosed monkey, drill, Bactrian camel, baiji, mouflon, Tibetan antelope, prairie vole, black flying fox, Florida manatee, large flying fox, African bush elephant, white-tailed deer, giant panda, green monkey, common degu, common shrew, Damara mole-rat, black-capped squirrel monkey, Tasmanian devil, great roundleaf bat, narrow-ridged finless porpoise, spalax, rhesus macaque, dromedary, golden snub-nosed monkey, koala, water buffalo, gray short-tailed opossum, Pacific walrus, common marmoset, southern pig-tailed macaque, common chimpanzee, Hawaiian monk seal, crab-eating macaque, polar bear, wild Bactrian camel, grizzly bear, gray mouse lemur, northern white-cheeked gibbon, or bonobo.

Other sequences expressing OGlcNA or related or homologous genes can be identified in a database such as, for example, GenBank. In one aspect, sequences useful herein include those with the GI numbers listed in Table 3.

TABLE 3

OGlcNA Genes

| Source Organism | Sequence Description | GI Number |
| --- | --- | --- |
| Rattus norvegicus | O-GlcNAcase | NM_131904.1 |
| Rattus norvegicus | meningioma expressed antigen 5 | XM_017588708.1 |
| Marmota marmota marmota | meningioma expressed antigen 5 | XM_015494690.1 |
| Sus scrofa | meningioma expressed antigen 5 | XM_003483548.4 |
| Urocitellus parryii | O-GlcNAcase | XM_026407874.1 |
| Ictidomys tridecemlineatus | O-GlcNAcase | XM_013363728.2 |
| Equus caballus | meningioma expressed antigen 5 | XM_023640514.1 |
| Equus caballus | meningioma expressed antigen 5 | XM_001499535.5 |
| Equus przewalskii | meningioma expressed antigen 5 | XM_008520873.1 |
| Mus musculus | cytosolic beta-N-acetylglucosaminidase | AF132214.1 |
| Erinaceus europaeus | meningioma expressed antigen 5 | XM_007533846.2 |
| Panthera pardus | meningioma expressed antigen 5 | XM_019459219.1 |
| Ceratotherium simum simum | meningioma expressed antigen 5 | XM_004427981.2 |
| Mus musculus | meningioma expressed antigen 5 | BC054821.1 |
| Enhydra lutris kenyoni | meningioma expressed antigen 5 | XM_022499195.1 |
| Enhydra lutris kenyoni | meningioma expressed antigen 5 | XM_022499194.1 |
| Dipodomys ordii | meningioma expressed antigen 5 | XM_013017723.1 |

TABLE 3-continued

OGlcNA Genes

| Source Organism | Sequence Description | GI Number |
| --- | --- | --- |
| Castor canadensis | meningioma expressed antigen 5 | XM_020171238.1 |
| Mus caroli | meningioma expressed antigen 5 | XM_021151375.1 |
| Mus caroli | meningioma expressed antigen 5 | XM_021151374.1 |
| Mus caroli | meningioma expressed antigen 5 | XM_021151373.1 |
| Panthera tigris altaica | meningioma expressed antigen 5 | XM_007080283.1 |
| Mus musculus | meningioma expressed antigen 5 | NM_023799.4 |
| Tupaia chinensis | meningioma expressed antigen 5 | XM_006166334.2 |
| Acinonyx jubatus | O-GlcNAcase | XM_027062915.1 |
| Equus asinus | meningioma expressed antigen 5 | XM_014837652.1 |
| Mustela putorius furo | meningioma expressed antigen 5 | XM_004749434.2 |
| Mustela putorius furo | meningioma expressed antigen 5 | XM_004749433.2 |
| Mus musculus | hypothetical protein | AK129188.1 |
| Mus pahari | meningioma expressed antigen 5 | XM_021187683.1 |
| Heterocephalus glaber | meningioma expressed antigen 5 | XM_004866368.3 |
| Felis catus | meningioma expressed antigen 5 | XM_003994344.5 |
| Meriones unguiculatus | meningioma expressed antigen 5 | XM_021649955.1 |
| Delphinapterus leucas | meningioma expressed antigen 5 | XM_022568972.1 |
| Papio anubis | meningioma expressed antigen 5 | XM_003904159.3 |
| Propithecus coquereli | meningioma expressed antigen 5 | XM_012661710.1 |
| Tursiops truncates | meningioma expressed antigen 5 | XM_019939852.1 |
| Rousettus aegyptiacus | meningioma expressed antigen 5 | XM_016120014.1 |
| Balaenoptera acutorostrata scammoni | meningioma expressed antigen 5 | XM_007187305.1 |
| Theropilhecus gelada | O-GlcNAcase | XM_025397972.1 |
| Rhinolophus sinicus | meningioma expressed antigen 5 | XM_019724961.1 |
| Orcinus orca | meningioma expressed antigen 5 | XM_012532559.1 |
| Orcinus orca | meningioma expressed antigen 5 | XM_004268486.2 |
| Canis lupus dingo | O-GlcNAcase | XM_025466984.1 |
| Callorhinus ursinus | O-GlcNAcase | XM_025880995.1 |
| Canis lupus famialiaris | meningioma expressed antigen 5 | XM_534996.6 |
| Manis javanica | meningioma expressed antigen 5 | XM_017674347.1 |
| Desmodus rotundus | meningioma expressed antigen 5 | XM_024555707.1 |
| Lagenorhynchus obliquidens | O-GlcNAcase | XM_027112366.1 |
| Gordla gorilla gorilla | meningioma expressed antigen 5 | XM_004049990.2 |
| Pongo abelii | meningioma expressed antigen 5 | XM_009245728.2 |
| Physeter catodon | meningioma expressed antigen 5 | XM_007116100.2 |
| Piliocolobus tephrosceles | O-GlcNAcase | XM_023206465.1 |
| Rhinopithecus bieti | meningioma expressed antigen 5 | XM_017851728.1 |
| Mandrillus leucophaeus | meningioma expressed antigen 5 | XM_011977442.1 |
| Camelus bactrianus | meningioma expressed antigen 5 | XM_010971007.1 |
| Lipotes vexilifer | meningioma expressed antigen 5 | XM_007470370.1 |
| Ovis aries musimon | meningioma expressed antigen 5 | XM_012119661.2 |
| Pantholops hodgsonii | meningioma expressed antigen 5 | XM_005980709.1 |
| Microtus ochrogaster | O-GlcNAcase | XM_005352373.3 |
| Pteropus alecto | O-GlcNAcase | XM_006925850.3 |
| Trichechus manatus latirostris | meningioma expressed antigen 5 | XM_004370059.2 |
| Pteropus vampyrus | meningioma expressed antigen 5 | XM_011378888.2 |
| Loxodonta africana | meningioma expressed antigen 5 | XM_003409163.3 |
| Odocoileus virginianus texanus | meningioma expressed antigen 5 | XM_020897815.1 |
| Odocoileus virginianus texanus | meningioma expressed antigen 5 | XM_020897813.1 |
| Ailuropoda melanoleuca | meningioma expressed antigen 5 | XM_011236048.2 |
| Ailuropoda melanoleuca | meningioma expressed antigen 5 | XM_002913873.3 |
| Chlorocebus sabaeus | meningioma expressed antigen 5 | XM_007963927.1 |
| Octodon degus | meningioma expressed antigen 5 | XM_004631450.2 |
| Odocoileus virginianus texanus | meningioma expressed antigen 5 | XM_020897814.1 |
| Sorex araneus | meningioma expressed antigen 5 | XM_004616334.2 |
| Fukomys damarensis | meningioma expressed antigen 5 | XM_010626504.1 |
| Saimiri boliviensis boliviensis | meningioma expressed antigen 5 | XM_003922263.2 |
| Sarcophilus harrisii | meningioma expressed antigen 5 | XM_003755444.3 |
| Hipposideros armiger | meningioma expressed antigen 5 | XM_019636367.1 |
| Neophocaena asiaeorientalis asiaeorientalis | O-GlcNAcase | XM_024734837.1 |
| Nannospalax galili | meningioma expressed antigen 5 | XM_008845612.2 |
| Macaca mulatta | meningioma expressed antigen 5 | XM_015148051.1 |
| Camelus dromedarius | meningioma expressed antigen 5 | XM_010974469.1 |
| Rhinopithecus roxellana | meningioma expressed antigen 5 | XM_010356139.1 |
| Phascolarctos cinereus | meningioma expressed antigen 5 | XM_020967113.1 |
| Bubalus bubalis | O-GlcNAcase | NM_001290956.1 |
| Monodelphis domestica | meningioma expressed antigen 5 | XM_001369640.3 |
| Odobenus rosmarus divergens | meningioma expressed antigen 5 | XM_012562921.1 |
| Odobenus rosmarus divergens | meningioma expressed antigen 5 | XM_004401951.1 |
| Callithrix jacchus | meningioma expressed antigen 5 | XM_002756542.3 |
| Macaca nemestrina | O-GlcNAcase | XM_011735546.2 |
| Pan trodlogytes | meningioma expressed antigen 5 | XM_507996.7 |
| Neomonachus schauinslandi | meningioma expressed antigen 5 | XM_021700283.1 |
| Macaca fascicularis | meningioma expressed antigen 5 | XM_005566254.2 |

TABLE 3-continued

OGlcNA Genes

| Source Organism | Sequence Description | GI Number |
|---|---|---|
| Ursus maritimus | meningioma expressed antigen 5 | XM_008709033.1 |
| Equus caballus | meningioma expressed antigen 5 | XM_023640519.1 |
| Castor canadensis | meningioma expressed antigen 5 | XM_020171236.1 |
| Camelus ferus | meningioma expressed antigen 5 | XM_006183010.2 |
| Ursus arctos horribilis | O-GlcNAcase | XM_026493941.1 |
| Microcebus murinus | meningioma expressed antigen 5 | XM_012769426.2 |
| Microcebus murinus | meningioma expressed antigen 5 | XM_020280663.1 |
| Nomascus leucogenys | meningioma expressed antigen 5 | XM_003255376.2 |
| Pan paniscus | O-GlcNAcase | XM_003825499.2 |

In another aspect, said construct further includes a promoter, a terminator or stop sequence, a gene that confers resistance to an antibiotic (a "selective marker"), a reporter protein, or a combination thereof.

In one aspect, the construct includes a regulatory sequence. In a further aspect, the regulatory sequence is already incorporated into a vector such as, for example, a plasmid, prior to genetic manipulation of the vector. In another aspect, the regulatory sequence can be incorporated into the vector through the use of restriction enzymes or any other technique known in the art.

In one aspect, the regulatory sequence is a promoter. The term "promoter" refers to a DNA sequence capable of controlling the expression of a coding sequence. In one aspect, the coding sequence to be controlled is located 3' to the promoter. In another aspect, the promoter is derived from a native gene. In an alternative aspect, the promoter is composed of multiple elements derived from different genes and/or promoters. A promoter can be assembled from elements found in nature, from artificial or synthetic elements, or from a combination thereof. It is understood by those skilled in the art that different promoters can direct the expression of a gene in different tissues or cell types, at different stages of development, in response to different environmental or physiological conditions, and/or in different species. In one aspect, the promoter functions as a switch to activate the expression of a gene.

In one aspect, the promoter is "constitutive." A constitutive promoter is a promoter that causes a gene to be expressed in most cell types at most times. In another aspect, the promoter is "regulated." A regulated promoter is a promoter that becomes active in response to a specific stimulus. A promoter may be regulated chemically, such as, for example, in response to the presence or absence of a particular metabolite (e.g., lactose or tryptophan), a metal ion, a molecule secreted by a pathogen, or the like. A promoter may also be regulated physically, such as, for example, in response to heat, cold, water stress, salt stress, oxygen concentration, illumination, wounding, or the like.

Promoters that are useful to drive expression of the nucleotide sequences described herein are numerous and familiar to those skilled in the art. Suitable promoters include, but are not limited to, the following: T3 promoter, T7 promoter, an iron promoter, a glucose promoter, and GAL1 promoter. In one aspect, the promoter is a glucose promoter. In a further aspect, the glucose promoter has SEQ ID NO. 16, 17, 18, or 19 or at least 70% homology thereto, at least 75% homology thereto, at least 80% homology thereto, at least 85% homology thereto, at least 90% homology thereto, or at least 95% homology thereto. In another aspect, the promoter is the native GAL1 promoter found in the plasmid pYES2. Variants of these promoters are also contemplated. The skilled artisan will be able to use site-directed mutagenesis and/or other mutagenesis techniques to modify the promoters to promote more efficient function. The promoter may be positioned, for example, at about 10-100 nucleotides from a ribosomal binding site. In another aspect, the promoter is positioned before the gene that expresses SNF3, OGT, OGlcNA, or a combination thereof. In an alternative aspect, several different promoters can be used in the same DNA construct.

In one aspect, the promoter is a GAL1 promoter. In another aspect, the GAL1 promoter is native to the plasmid used to create the vector. In another aspect, a GAL1 promoter is positioned before any or all genetic components present in the device. In another aspect, the promoter is a GAL1 promoter obtained from or native to the pYES2 plasmid.

In another aspect, the regulatory sequence is a terminator or stop sequence. As used herein, a "terminator" is a sequence of DNA that marks the end of a gene or operon to be transcribed. In a further aspect, the terminator is an intrinsic terminator or a Rho-dependent transcription terminator. As used herein, an intrinsic terminator is a sequence wherein a hairpin structure can form in the nascent transcript that disrupts the mRNA/DNA/RNA polymerase complex. As used herein, a Rho-dependent transcription terminator requires a Rho factor protein complex to disrupt the mRNA/DNA/RNA polymerase complex. In one aspect, the terminator is a T7 terminator. In an alternative aspect, the terminator is a CYC1 terminator obtained from or native to the pYES2 plasmid. In still another aspect, the DNA construct can include multiple terminators. In one aspect, the terminator is native to the vector in which the DNA construct is incorporated. In an alternative aspect, a terminator is positioned after each gene of interest in the 5' to 3' direction. In one aspect, the terminator has SEQ ID NO. 20 or at least 70% homology thereto, at least 75% homology thereto, at least 80% homology thereto, at least 85% homology thereto, at least 90% homology thereto, or at least 95% homology thereto.

In a further aspect, the regulatory sequence includes both a promoter and a terminator or stop sequence. In a still further aspect, the regulatory sequence can include multiple promoters or terminators. Other regulatory elements, such as enhancers, are also contemplated. Enhancers may be located from about 1 to about 2000 nucleotides in the 5' direction from the start codon of the DNA to be transcribed, or may be located 3' to the DNA to be transcribed. Enhancers may be "cis-acting," that is, located on the same molecule of DNA as the gene whose expression they affect.

In another aspect, the vector contains one or more ribosomal binding sites. As used herein, a "ribosomal binding site" is a sequence of nucleotides located 5' to the start codon of an mRNA that recruits a ribosome to initiate protein translation. In one aspect, the ribosomal binding site can be positioned before any or all genes in a DNA construct, or a before a subset of genes in a DNA construct. In one aspect, the ribosomal binding site has SEQ ID NO. 24, 25, or 26, or about 70% homology thereto, about 75% homology thereto, about 80% homology thereto, about 85% homology thereto, about 90% homology thereto, or about 95% homology thereto.

In some aspects, the vector further includes a riboswitch. In one aspect, the riboswitch has SEQ ID NO. 21, 22, or 23, or about 70% homology thereto, about 75% homology thereto, about 80% homology thereto, about 85% homology thereto, about 90% homology thereto, or about 95% homology thereto. As used herein, a "riboswitch" is a regulatory segment of an mRNA molecule that binds a small molecule such as, for example, glucose, thereby resulting in a change in production of the proteins encoded in the mRNA.

In one aspect, when the vector is a plasmid, the plasmid can also contain a multiple cloning site or polylinker. In a further aspect, the polylinker contains recognition sites for multiple restriction enzymes. The polylinker can contain up to 2, 3, 4, 5, 6, 7, 8, 9, 10, 11, 12, 13, 14, 15, 16, 17, 18, 19, 20, or more than 20 recognition sites for multiple restriction enzymes. Further, restriction sites may be added, disabled, or removed as required, using techniques known in the art. In one aspect, the plasmid contains restriction sites for any known restriction enzyme such as, for example, HindIII, KpnI, SacI, BamHI, BstXI, EcoRI, BsaBI, NotI, XhoI, SphI, XbaI, ApaI, SalI ClaI, EcoRV, PstI, SmaI, SpeI, EagI, SacII, or any combination thereof. In a further aspect, the plasmid contains more than one recognition site for the same restriction enzyme.

In one aspect, the restriction enzyme can cleave DNA at a palindromic or an asymmetrical restriction site. In a further aspect, the restriction enzyme cleaves DNA to leave blunt ends; in an alternative aspect, the restriction enzyme cleaves DNA to leave "sticky" or overhanging ends. In another aspect, the enzyme can cleave DNA a distance of from 20 bases to over 1000 bases away from the restriction site. A variety of restriction enzymes are commercially available and their recognition sequences, as well as instructions for use (e.g., amount of DNA needed, precise volumes of reagents, purification techniques, as well as information about salt concentration, pH, optimum temperature, incubation time, and the like) are provided by enzyme manufacturers.

In one aspect, a plasmid with a polylinker containing one or more restriction sites can be digested with one restriction enzyme and a nucleotide sequence of interest can be ligated into the plasmid using a commercially-available DNA ligase enzyme. Several such enzymes are available, often as kits containing all reagents and instructions required for use. In another aspect, a plasmid with a polylinker containing two or more restriction sites can be simultaneously digested with two restriction enzymes and a nucleotide sequence of interest can be ligated into the plasmid using a DNA ligase enzyme. Using two restriction enzymes provides an asymmetric cut in the DNA, allowing for insertion of a nucleotide sequence of interest in a particular direction and/or on a particular strand of the double-stranded plasmid. Since RNA synthesis from a DNA template proceeds from 5' to 3', usually starting just after a promoter, the order and direction of elements inserted into a plasmid can be especially important. If a plasmid is to be simultaneously digested with multiple restriction enzymes, these enzymes must be compatible in terms of buffer, salt concentration, and other incubation parameters.

In some aspects, prior to ligation using a ligase enzyme, a plasmid that has been digested with a restriction enzyme is treated with an alkaline phosphatase enzyme to remove 5' terminal phosphate groups. This prevents self-ligation of the plasmid and thus facilitates ligation of heterologous nucleotide fragments into the plasmid.

In one aspect, different genes can be ligated into a plasmid in one pot. In this aspect, the genes will first be digested with restriction enzymes. In certain aspects, the digestion of genes with restriction enzymes provides multiple pairs of matching 5' and 3' overhangs that will spontaneously assemble the genes in the desired order. In another aspect, the genes and components to be incorporated into a plasmid can be assembled into a single insert sequence prior to insertion into the plasmid. In a further aspect, a DNA ligase enzyme can be used to assist in the ligation process.

In another aspect, the ligation mix may be incubated in an electromagnetic chamber. In one aspect, this incubation lasts for about 1 minute, about 2 minutes, about 5 minutes, about 10 minutes, about 15 minutes, about 20 minutes, about 30 minutes, or about 1 hour.

The DNA construct described herein can be part of a vector. In general, plasmid vectors containing replicon and control sequences that are derived from species compatible with the host cell are used in connection with the hosts. The vector ordinarily carries a replication site as well as marking sequences that are capable of performing phenotypic selection in transformed cells. Plasmid vectors are well known and are commercially available. Such vectors include, but are not limited to, pWLneo, pSV2cat, pOG44, pXT1, pSG, pSVK3, pBSK, pBR322, pYES, pYES2, pBSKII, pUC, pUC19, and pETDuet-1 vectors.

Plasmids are double-stranded, autonomously-replicating, genetic elements that are not integrated into host cell chromosomes. Further, these genetic elements are usually not part of the host cell's central metabolism. In bacteria, plasmids may range from 1 kilobase (kb) to over 200 kb. Plasmids can be engineered to encode a number of useful traits including the production of secondary metabolites, antibiotic resistance, the production of useful proteins, degradation of complex molecules and/or environmental toxins, and others. Plasmids have been the subject of much research in the field of genetic engineering, as plasmids are convenient expression vectors for foreign DNA in, for example, microorganisms. Plasmids generally contain regulatory elements such as promoters and terminators and also usually have independent replication origins. Ideally, plasmids will be present in multiple copies per host cell and will contain selectable markers (such as genes for antibiotic resistance) to allow the skilled artisan to select host cells that have been successfully transfected with the plasmids (for example, by growing the host cells in a medium containing the antibiotic).

In one aspect, the vector encodes a selective marker. In a further aspect, the selective marker is a gene that confers resistance to an antibiotic. In certain aspects, during fermentation of host cells transformed with the vector, the cells are contacted with the antibiotic. For example, the antibiotic may be included in the culture medium. Cells that have not successfully been transformed cannot survive in the presence of the antibiotic; only cells containing the vector that confers antibiotic resistance can survive. Optimally, only cells containing the vector to be expressed will be cultured, as this will result in the highest production efficiency of the desired gene products (e.g., proteins). Cells that do not contain the vector would otherwise compete with transformed cells for resources. In one aspect, the antibiotic is tetracycline, neomycin, kanamycin, ampicillin, hygromycin, chloramphenicol, amphotericin B, bacitracin, carbapenam, cephalosporin, ethambutol, fluoroquinolones, isoniazid, methicillin, oxacillin, vancomycin, streptomycin, quinolones, rifampin, rifampicin, sulfonamides, cephalothin, erythromycin, gentamycin, penicillin, other commonly-used antibiotics, or a combination thereof.

In certain aspects, the DNA construct can include a gene that expresses a reporter protein. The selection of the reporter protein can vary. For example, the reporter protein can be a yellow fluorescent protein, a red fluorescent protein, a green fluorescent protein, or a cyan fluorescent protein. In one aspect, the reporter protein is a yellow fluorescent protein and the gene that expresses the reporter protein has SEQ ID NO. 27 or at least 70% homology thereto, at least 75% homology thereto, at least 80% homology thereto, at least 85% homology thereto, at least 90% homology thereto, or at least 95% homology thereto. In another aspect, the reporter protein is a green fluorescent protein and the gene that expresses the reporter protein has SEQ ID NO. 4 or at least 70% homology thereto, at least 75% homology thereto, at least 80% homology thereto, at least 85% homology thereto, at least 90% homology thereto, or at least 95% homology thereto. In one aspect, the green fluorescent protein is enhanced green fluorescent protein (EGFP).

The amount of fluorescence that is produced by the biological device can be correlated to the amount of DNA incorporated into the microbial host cells. The fluorescence produced by the device can be detected and quantified using techniques known in the art. For example, spectrofluorometers are typically used to measure fluorescence. The Examples provide exemplary procedures for measuring the amount of fluorescence produced as a result of the expression of DNA.

In one aspect, the construct includes the following genetic components: (a) a gene that expresses SNF3, (b) a gene that expresses OGT, and (c) a gene that expresses OGlcNA. In another aspect, the construct includes the following genetic components: (a) a gene that expresses SNF3, (b) a gene that expresses OGT, (c) a gene that expresses OGlcNA, and (d) a gene that expresses a reporter protein.

In another aspect, the DNA construct has the following genetic components: (1) one or more promoters, (2) a gene that expresses SNF3, (3) a gene that expresses OGT, (4) a gene that expresses OGlcNA, (5) a gene that expresses a reporter protein, and (6) one or more terminators or stop sequences.

In one aspect, the construct includes from 5' to 3' the following genetic components in the following order: (a) a gene that expresses SNF3, (b) a gene that expresses OGT, and (c) a gene that expresses OGlcNA. In another aspect, the construct includes from 5' to 3' the following genetic components in the following order: (a) a gene that expresses SNF3, (b) a gene that expresses OGT, (c) a gene that expresses OGlcNA, and (d) a gene that expresses a reporter protein.

In one aspect, the construct is a pYES2 or pBKSII plasmid having from 5' to 3' the following genetic components in the following order: (a) a gene that expresses SNF3, (b) a gene that expresses OGT, and (c) a gene that expresses OGlcNA. In another aspect, the construct is a pYES2 or pBKSII plasmid having from 5' to 3' the following genetic components in the following order: (a) a gene that expresses SNF3, (b) a gene that expresses OGT, (c) a gene that expresses OGlcNA, and (d) a gene that expresses a reporter protein.

In another aspect, the construct comprises from 5' to 3' the following genetic components in the following order: (a) a gene that expresses SNF3, (b) a CYC1 terminator, (c) a GAL1 promoter, (d) a gene that expresses OGT, (e) a CYC1 terminator, (f) a GAL1 promoter, (g) a gene that expresses OGlcNA, (h) a CYC1 terminator, (i) a GAL1 promoter, and (j) a gene that expresses a reporter protein.

In another aspect, the construct comprises from 5' to 3' the following genetic components in the following order: (a) a gene that expresses SNF3 having SEQ ID NO. 1 or at least 70% homology thereto, (b) a CYC1 terminator, (c) a GAL1 promoter, (d) a gene that expresses OGT having SEQ ID NO. 2 or at least 70% homology thereto, (e) a CYC1 terminator, (f) a GAL1 promoter, (g) a gene that expresses OGlcNA having SEQ ID NO. 3 or at least 70% homology thereto, (h) a CYC1 terminator, (i) a GAL1 promoter, and (j) a gene that expresses a reporter protein having SEQ ID NO. 4 or at least 70% homology thereto.

Figure 2:
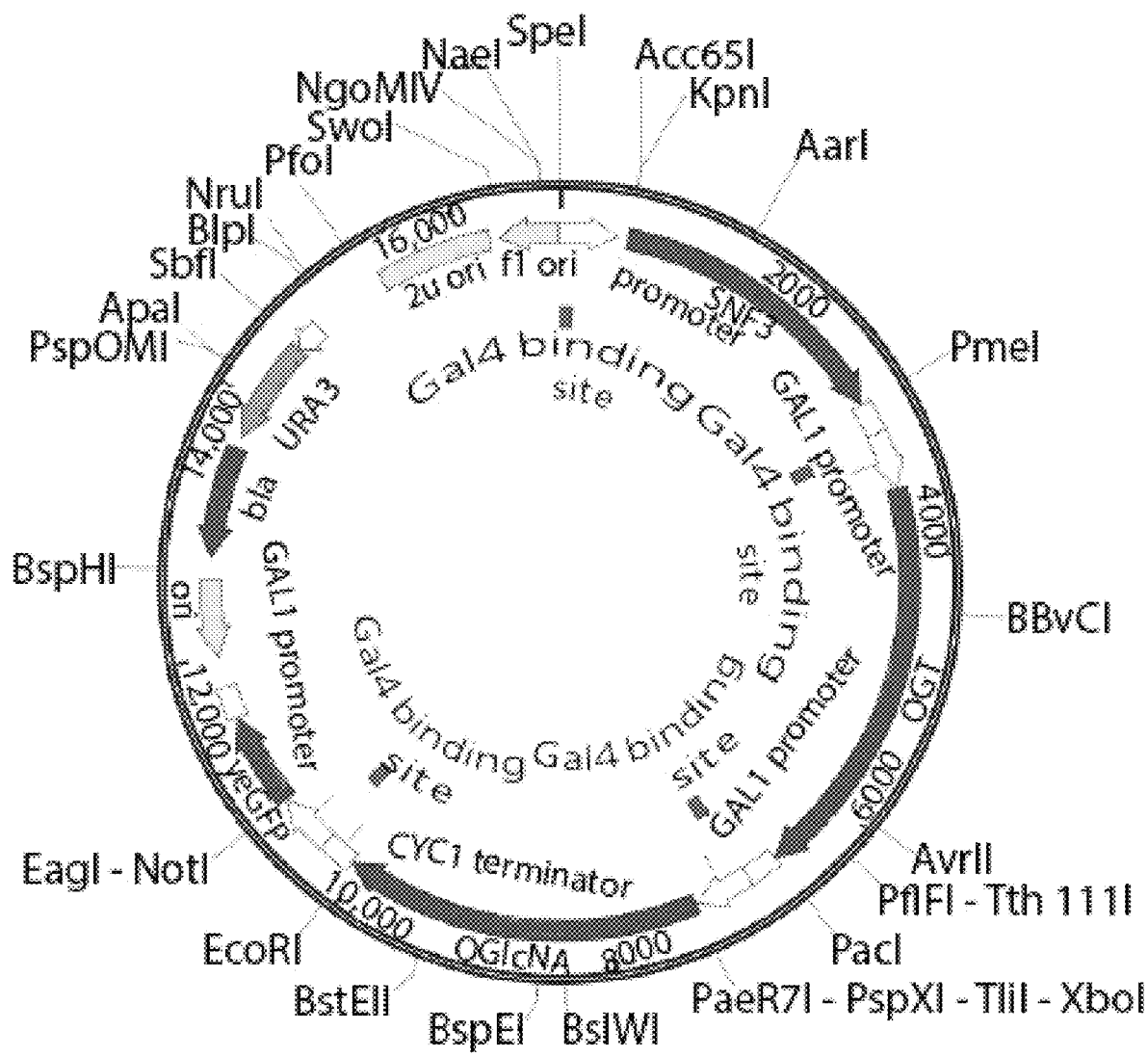
FIG. 2 shows a circular schematic of a vector described herein, wherein the vector has SEQ ID NO. 5.

In another aspect, the DNA construct has SEQ ID NO. 5 or at least 70% homology thereto, at least 75% homology thereto, at least 80% homology thereto, at least 85% homology thereto, at least 90% homology thereto, or at least 95% homology thereto. FIGS. 1 and 2 provide non-limiting examples of DNA constructs described herein.

Exemplary methods for producing the DNA constructs described herein are provided in the Examples. Restriction enzymes and purification techniques known in the art can be used to assemble the DNA constructs. Backbone plasmids and synthetic inserts can be mixed together for ligation purposes at different ratios such as, for example, 1:1, 1:2, 1:3, 1:4, and up to 1:5. In one aspect, the ratio of the backbone plasmid to synthetic insert is 1:4. After the vector comprising the DNA construct has been produced, the resulting vector can be incorporated into the host cells using the methods described below.

II. Biological Devices

In one aspect, a "biological device" is formed when a microbial cell is transfected with the DNA construct described herein. The biological devices are generally composed of microbial host cells, where the host cells are transformed with a DNA construct as described herein.

In one aspect, the DNA construct is carried by the expression vector into the cell and is separate from the host cell's genome. In another aspect, the DNA construct is incorporated into the host cell's genome. In still another aspect, incorporation of the DNA construct into the host cell enables the host cell to produce SNF3, OGT, and OGlcNA, devices and extracts that can be used to measure glucose levels. "Heterologous" genes and proteins are genes and proteins that have been experimentally inserted into a cell that are not normally expressed by that cell. A heterologous gene may be cloned or derived from a different cell type or species than the recipient cell or organism. Heterologous genes may be introduced into cells by transfection or transformation.

An "isolated" nucleic acid is one that has been separated from other nucleic acid molecules and/or cellular material (peptides, proteins, lipids, saccharides, and the like) normally present in the natural source of the nucleic acid. An "isolated" nucleic acid may optionally be free of the flanking sequences found on either side of the nucleic acid as it naturally occurs. An isolated nucleic acid can be naturally occurring, can be chemically synthesized, or can be a cDNA molecule (i.e., is synthesized from an mRNA template using reverse transcriptase and DNA polymerase enzymes).

"Transformation" or "transfection" as used herein refers to a process for introducing heterologous DNA into a host cell. Transformation can occur under natural conditions or may be induced using various methods known in the art. Many methods for transformation are known in the art and the skilled practitioner will know how to choose the best transformation method based on the type of cells being transformed. Methods for transformation include, for example, viral infection, electroporation, lipofection, chemical transformation, and particle bombardment. Cells may be stably transformed (i.e., the heterologous DNA is capable of replicating as an autonomous plasmid or as part of the host chromosome) or may be transiently transformed (i.e., the heterologous DNA is expressed for only a limited period of time).

"Competent cells" refers to microbial cells capable of taking up heterologous DNA. Competent cells can be purchased from a commercial source, or cells can be made competent using procedures known in the art. Exemplary procedures for producing competent cells are provided in the Examples.

The host cells as referred to herein include their progeny, which are any and all subsequent generations formed by cell division. It is understood that not all progeny may be identical due to deliberate or inadvertent mutations. A host cell may be "transfected" or "transformed" which refers to a process by which exogenous nucleic acid is transferred or introduced into the host cell.

The host cells can be naturally-occurring cells or "recombinant" cells. Recombinant cells are distinguishable from naturally-occurring cells in that naturally-occurring cells do not contain heterologous DNA introduced through molecular cloning procedures. In one aspect, the host cell is a prokaryotic cell such as, for example, *Escherichia coli*. In other aspects, the host cell is a eukaryotic cell such as, for example, the yeast *Saccharomyces cerevisiae*. Host cells transformed with the DNA construct described herein are referred to as "biological devices."

The DNA construct is first delivered into the host cell. In one aspect, the host cells are naturally competent (i.e., able to take up exogenous DNA from the surrounding environment). In another aspect, cells must be treated to induce artificial competence. This delivery may be accomplished in vitro, using well-developed laboratory procedures for transforming cell lines. Transformation of bacterial cell lines can be achieved using a variety of techniques. One method involves calcium chloride. The exposure to the calcium ions renders the cells able to take up the DNA construct. Another method is electroporation. In this technique, a high-voltage electric field is applied briefly to cells, producing transient holes in the membranes of the cells through which the vector containing the DNA construct enters. Another method involves exposing intact yeast cells to alkali cations such as, for example, lithium. In one aspect, this method includes exposing yeast to lithium acetate, polyethylene glycol, and single-stranded DNA such as, for example, salmon sperm DNA. Without wishing to be bound by theory, the single-stranded DNA is thought to bind to the cell wall of the yeast, thereby blocking plasmids from binding. The plasmids are then free to enter the yeast cell. Enzymatic and/or electromagnetic techniques can also be used alone, or in combination with other methods, to transform microbial cells. Exemplary procedures for transforming yeast and bacteria with specific DNA constructs are provided in the Examples. In certain aspects, two or more types of DNA can be incorporated into the host cells. Thus, different metabolites can be produced from the same host cells at enhanced rates.

III. Preparation of Devices and Extracts

The biological devices described herein are useful in the production of compositions and extracts that can be used to measure glucose levels in a subject. Once the DNA construct has been incorporated into the host cell, the cells are cultured such that the cells multiply. A satisfactory microbiological culture contains available sources of hydrogen donors and acceptors, carbon, nitrogen, sulfur, phosphorus, inorganic salts, and, in certain cases, vitamins or other growth-promoting substances. For example, the addition of peptone provides a readily-available source of nitrogen and carbon. Furthermore, the use of different types of media results in different growth rates and different stationary phase densities; stationary phase is where secondary metabolite production occurs most frequently. A rich media results in a short doubling time and higher cell density at stationary phase. Minimal media results in slow growth and low final cell densities. Efficient agitation and aeration increase final cell densities.

In one aspect, host cells may be cultured or fermented by any method known in the art. The skilled practitioner will be able to select a culture medium based on the species and/or strain of host cell selected. In certain aspects, the culture medium will contain a carbon source. A variety of carbon sources are contemplated, including, but not limited to: monosaccharides such as glucose and fructose, disaccharides such as lactose or sucrose, oligosaccharides, polysaccharides such as starch, or mixtures thereof. Unpurified mixtures extracted from feedstocks are also contemplated as carbon sources, as are one-carbon substrates such as carbon dioxide and/or methanol in the cases of compatible organisms. The carbon source utilized is limited only by the particular organism being cultured.

Culturing or fermenting of host cells may be accomplished by any technique known in the art. In one aspect, batch fermentation may be conducted. In batch fermentation, the composition of the culture medium is set at the beginning and the system is closed to future artificial alterations. In some aspects, a limited form of batch fermentation may be carried out wherein factors such as oxygen concentration and pH are manipulated, but additional carbon is not added. Continuous fermentation methods are also contemplated. In continuous fermentation, equal amounts of a defined medium are continuously added to and removed from a bioreactor. In other aspects, microbial host cells are immobilized on a substrate. Fermentation may be carried out on any scale and may include methods in which literal "fermentation" is carried out as well as other culture methods that are non-fermentative.

In one aspect, the method involves growing the biological devices described herein for a sufficient time to produce SNF3, OGT, and OGlcNA. The ordinary artisan will be able to choose a culture medium and optimum culture conditions based on the biological identity of the host cells.

In certain aspects, after culturing the biological device to produce the proteins of interest, the host cells of the device can be lysed with one or more enzymes to produce an extract. For example, when the host cells are yeast, the yeast cells can be lysed with lyticase. In one aspect, the lyticase concentration can be 500, 600, 700, 800, 900, or 1000 μL per liter of culture, where any value can be the lower or upper endpoint of a range (e.g., 500 to 900 μL, 600 to 800 μL, etc.).

In addition to enzymes, other components can be used to facilitate lysis of the host cells. In one aspect, chitosan can be used in combination with an enzyme to lyse the host cells.

Chitosan is generally composed of glucosamine units and N-acetylglucosamine units and can be chemically or enzymatically extracted from chitin, which is a component of arthropod exoskeletons and fungal and microbial cell walls. In certain aspects, the chitosan can be acetylated to a specific degree of acetylation. In one aspect, the chitosan is from 60% to about 100%, 70% to 90%, 75% to 85%, or is about 80% acetylated. The molecular weight of the chitosan can vary, as well. For example, the chitosan comprises about 3, 4, 5, 6, 7, 8, 9, 10, 11, 12, 13, 14, 15, 16, 17, 18, 19, or 20 glucosamine units and/or N-acetylglucosamine units. In another aspect, the chitosan includes 5 to 7 glucosamine units and/or N-acetylglucosamine units. In one aspect, the chitosan can be added until a concentration of 0.0015, 0.0025, 0.0050, 0.0075, 0.01, 0.015, 0.02, 0.03, 0.04, or 0.05% (v/v) is achieved in the culture, where any value can be a lower or an upper end-point of a range (e.g., 0.005 to 0.02%, 0.0075 to 0.015%, etc.). Still further in this aspect, the chitosan is present at a concentration of 0.01%.

In a further aspect, a composition composed of SNF3, OGT, OGlcNA, and optionally a reporter protein can be collected, separated from the microbial cells (lysed or intact), and/or purified through any technique known in the art such as, for example, extraction, precipitation, ultracentrifugation, filtration, size exclusion chromatography, ion exchange chromatography, affinity chromatography, high-pressure liquid chromatography, electrophoresis, any other technique known in the art, or a combination thereof. In an alternative aspect, the microbial cells secrete the proteins of interest into the culture medium.

In one aspect, compositions composed of the proteins of interest with lysed and/or intact host cells can be used herein where it is not necessary to separate the host cells and other components from the proteins.

In one aspect, provided herein are extracts containing SNF3, OGT, OGlcNA, and optionally a reporter protein. In a further aspect, the extracts are collected from cultures or culture media of host cells without lysing the cells. Further in this aspect, the cells can be filtered out or can be incorporated into the extract. In an alternative aspect, the extracts are collected from lysed cells and may be further purified. Exemplary procedures for producing and purifying the extracts are provided in the Examples.

IV. Applications of the Devices and Extracts

The biological devices and extracts produced therefrom can be used to detect and quantify glucose levels of a subject. As will be discussed below, elevated levels of glucose are associated with several serious diseases and medical conditions.

In one aspect, elevated levels of blood glucose are associated with diabetes. In another aspect, levels of blood glucose below those of a diabetic patient but elevated compared to the normal population average are associated with pre-diabetes and/or metabolic syndrome, both conditions that can develop into diabetes without treatment and/or lifestyle changes.

In one aspect, described herein is a method for measuring glucose levels in a subject, the method involving the steps of:
 (a) admixing a sample from the subject with the extract or composition produced from a biological device described herein to produce a test sample;
 (b) measuring fluorescence intensity of the test sample; and
 (c) correlating the fluorescence produced by the sample to the amount of glucose present in the sample.

In another aspect, described herein is a method for diagnosing or predicting a disease associated with elevated glucose levels in a subject, the method involving the steps of:
 (a) admixing a sample from the subject with the extract or composition produced from a biological device described herein to produce a test sample;
 (b) measuring fluorescence intensity of the test sample; and
 (c) correlating the fluorescence produced by the sample to the disease.

In one aspect, the sample from the subject can be blood, serum, plasma, saliva, urine, or a combination thereof. In another aspect, the sample can be obtained in a non-invasive manner and/or a manner that will not cause pain for a subject. In a further aspect, the sample does not require specialized equipment (e.g., lancet, lancing device, etc.) to obtain. In one aspect, the sample is saliva.

In a further aspect, biological devices, extracts, and compositions such as those described herein are used in diagnostic tests for the detection of diabetes (type 1 or 2) in living patients, including in the early stages of the disease (i.e., pre-diabetes or metabolic syndrome). In this aspect, the use of these diagnostic tests can identify at-risk patients at an early stage, when few or no symptoms are present, thus enabling physicians to start treatment early and delay the progression of the disease.

After the patient sample has been mixed with the extract or composition produced from the biological device, the amount of fluorescence that is subsequently produced is quantified using techniques and instrumentation known in the art. In one aspect, the amount of fluorescence that is produced can be correlated with glycemia (i.e., blood sugar) values from clinical blood sugar tests.

In one aspect, after the fluorescence has been quantified, the value is correlated in order to determine if (1) the subject has diabetes or (2) if the subject has pre-diabetes or is likely to develop diabetes. In one aspect, a chart or computer program can be used to correlate different fluorescence values to different symptoms or probabilities of having or contracting diabetes. Results from a series of such tests on diabetic, pre-diabetic, and healthy patients are presented in the Examples. In one aspect, the amount of fluorescence that is produced can be correlated with glycemia (i.e., blood sugar) values associated with diabetes or the onset of diabetes (i.e., pre-diabetes).

In one aspect, a clinician or medical provider may diagnose a patient with diabetes based on the presence of high fasting blood sugar levels. In a further aspect, the results from use of the devices, compositions, and methods described herein also correlated with results from clinical blood glucose tests. In a still further aspect, early diagnosis of pre-diabetes conditions paves the way for therapeutic, medical, pharmaceutical, and/or lifestyle intervention to delay or prevent the onset of diabetes.

V. Aspects

The following listing of exemplary aspects supports and is supported by the disclosure provided herein.

Aspect 1: A DNA construct comprising the following genetic components: (a) a gene that expresses SNF3, (b) a gene that expresses an O-linked N-acetylglucosamine transferase (OGT), (c) a gene that expresses an O-linked N-acetylglucosamine-selective-N-acetyl-β-D-glucosaminidase (OGlcNa), and (d) optionally a gene that expresses a fluorescent reporter protein.

Aspect 2: The DNA construct of aspect 1, wherein the gene that expresses SNF3 has one of SEQ ID NO. 1 or 6-15 or at least 70% homology thereto.

Aspect 3: The DNA construct of aspect 1, wherein the gene that expresses SNF3 has SEQ ID NO. 1 or at least 70% homology thereto.

Aspect 4: The DNA construct in any one of aspects 1-3, wherein the gene that expresses O-linked N-acetylglucosamine transferase has SEQ ID NO. 2 or at least 70% homology thereto.

Aspect 5: The DNA construct in any one of aspects 1-3, wherein the gene that expresses O-linked N-acetylglucosamine-selective-N-acetyl-β-D-glucosaminidase has SEQ ID NO. 3 or at least 70% homology thereto.

Aspect 6: The DNA construct in any one of aspects 1-5, wherein the construct further comprises a gene that expresses a fluorescent reporter protein.

Aspect 7: The DNA construct aspect 6, wherein the fluorescent reporter protein is a red fluorescent protein, a green fluorescent protein, a cyan fluorescent protein, or a yellow fluorescent protein.

Aspect 8: The DNA construct of aspect 6, wherein the fluorescent reporter protein is enhanced green fluorescent protein.

Aspect 9: The DNA construct aspect 6, wherein the gene that expresses the reporter protein has SEQ ID NO. 4 or 27 or at least 70% homology thereto.

Aspect 10: The DNA construct of aspect 6, wherein the gene that expresses the reporter protein has SEQ ID NO. 4 or at least 70% homology thereto.

Aspect 11: The DNA construct in any one of aspects 1-10, further comprising one or more promoters.

Aspect 12: The DNA construct of aspect 11, wherein the promoter is a T3 promoter, a T7 promoter, an iron promoter, a GAL1 promoter, or a glucose promoter.

Aspect 13: The DNA construct of aspect 11, wherein the promoter is a GAL1 promoter.

Aspect 14: The DNA construct of aspect 11, wherein the promoter is a GAL1 promoter, wherein the GAL1 promoter precedes each genetic component.

Aspect 15: The DNA construct of aspect 11, wherein the promoter has one of SEQ ID NO. 16-19 or at least 70% homology thereto.

Aspect 16: The DNA construct in any one of aspects 1-15, further comprising at least one terminator.

Aspect 17: The DNA construct of aspect 16, wherein the terminator is a T7 terminator or a CYC1 terminator.

Aspect 18: The DNA construct of aspect 16, wherein the terminator is a CYC1 terminator, wherein the CYC1 terminator follows each genetic component.

Aspect 19: The DNA construct of aspect 16, wherein the terminator has SEQ ID NO. 20 or at least 70% homology thereto.

Aspect 20: The DNA construct in any one of aspects 1-19, further comprising a gene that expresses a riboswitch.

Aspect 21: The DNA construct of aspect 20, wherein the riboswitch has one of SEQ ID NO. 21-23 or at least 70% homology thereto.

Aspect 22: The DNA construct in any one of aspects 1-21, further comprising a gene that expresses a ribosomal binding site.

Aspect 23: The DNA construct of aspect 22, wherein the ribosomal binding site has SEQ ID NO. 24-26 or at least 70% homology thereto.

Aspect 24: The DNA construct in any one of aspects 1-23, wherein the DNA construct comprises from 5' to 3' the following genetic components in the following order:
(a) a gene that expresses SNF3, (b) a gene that expresses O-linked N-acetylglucosamine transferase, and (c) a gene that expresses O-linked N-acetylglucosamine-selective-N-acetyl-β-D-glucosaminidase.

Aspect 25: The DNA construct in any one of aspects 1-23, wherein the DNA construct comprises from 5' to 3' the following genetic components in the following order:
(a) a gene that expresses SNF3, (b) a gene that expresses O-linked N-acetylglucosamine transferase, (c) a gene that expresses O-linked N-acetylglucosamine-selective-N-acetyl-β-D-glucosaminidase, and (d) a gene that expresses a reporter protein.

Aspect 26: The DNA construct in any one of aspects 1-23, wherein the DNA construct comprises from 5' to 3' the following genetic components in the following order:
(a) a gene that expresses SNF3, (b) a CYC1 terminator, (c) a GAL1 promoter, (d) a gene that expresses O-linked N-acetylglucosamine transferase, (e) a CYC1 terminator, (f) a GAL1 promoter, (g) a gene that expresses O-linked N-acetylglucosamine-selective-N-acetyl-β-D-glucosaminidase, (h) a CYC1 terminator, (i) a GAL1 promoter, and (j) a gene that expresses a reporter protein.

Aspect 27: The DNA construct in any one of aspects 1-23, wherein the DNA construct comprises from 5' to 3' the following genetic components in the following order:
(a) a gene that expresses SNF3 having SEQ ID NO. 1 or at least 70% homology thereto, (b) a CYC1 terminator, (c) a GAL1 promoter, (d) a gene that expresses O-linked N-acetylglucosamine transferase having SEQ ID NO. 2 or at least 70% homology thereto, (e) a CYC1 terminator, (f) a GAL1 promoter, (g) a gene that expresses O-linked N-acetylglucosamine-selective-N-acetyl-β-D-glucosaminidase having SEQ ID NO. 3 or at least 70% homology thereto, (h) a CYC1 terminator, (i) a GAL1 promoter, and (j) a gene that expresses a reporter protein having SEQ ID NO. 4 or at least 70% homology thereto.

Aspect 28: The DNA construct of aspect 1, wherein the DNA construct has SEQ ID NO. 5 or at least 70% homology thereto.

Aspect 29: The DNA construct in any one of aspects 1-28, wherein the DNA construct further comprises a gene that confers resistance to an antibiotic.

Aspect 30: The DNA construct of aspect 29, wherein the antibiotic comprises tetracycline, neomycin, kanamycin, ampicillin, hygromycin, chloramphenicol, amphotericin B, bacitracin, carbapenam, cephalosporin, ethambutol, fluoroquinolones, isoniazid, methicillin, oxacillin, vancomycin, streptomycin, quinolones, rifampin, rifampicin, sulfonamides, cephalothin, erythromycin, gentamycin, penicillin, other commonly-used antibiotics, or a combination thereof.

Aspect 31: A vector comprising the DNA construct in any one of aspect 1-30.

Aspect 32: The vector of aspect 31, wherein the vector is a plasmid.

Aspect 33: The vector of aspect 32, wherein the plasmid is pWLneo, pSV2cat, pOG44, pXT1, pSG, pSVK3, pBSK, pBSKII, pYES, pYES2, pUC, pUC19, or pET-Duet-1.

Aspect 34: The vector of aspect 32, wherein the plasmid is pYES2.

Aspect 35: A biological device comprising host cells transformed with the DNA construct in any one of aspects 1-30 or the vector in any one of aspects 31-34.

Aspect 36: The biological device of aspect 35, wherein the host cells comprise fungi or bacteria.

Aspect 37: The biological device of aspect 36, wherein the bacteria comprise E. coli.

Aspect 38: The biological device of aspect 36, wherein the fungi comprise yeast.

Aspect 39: The biological device of aspect 38, wherein the yeast comprise S. cerevisiae.

Aspect 40: An extract produced by culturing the biological device of aspects 35-39.

Aspect 41: The extract of aspect 40, wherein the extract is produced by:
(a) culturing the biological device in a culture medium; and
(b) removing the extract from the culture medium.

Aspect 42: A composition comprising SNF3, O-linked N-acetylglucosamine transferase, O-linked N-acetyl-glucosamine-selective-N-acetyl-β-D-glucosaminidase, and optionally a fluorescent reporter protein.

Aspect 43: A method for quantifying the amount of glucose in a subject, the method comprising:
(a) admixing the extract of aspects 40-41 or the composition of aspect 42 with a sample from the subject to produce a test sample;
(b) measuring the fluorescence produced by the test sample; and
(c) correlating the fluorescence produced by the test sample to the amount of glucose present in the sample.

Aspect 44: The method of aspect 43, wherein the fluorescence produced by the test sample is correlated to the amount of glucose present in the blood of the subject.

Aspect 45: A method for diagnosing or predicting a disease associated with elevated levels of glucose in a subject, the method comprising the steps of:
(a) admixing the extract of aspects 40-41 or the composition of aspect 42 with a sample from the subject to produce a test sample;
(b) measuring the fluorescence produced by the test sample; and
(c) correlating the fluorescence produced by the test sample to the disease.

Aspect 46: The method of aspect 45, wherein the fluorescence produced by the test sample is correlated to the amount of glucose present in the blood of the subject that is associated with the disease.

Aspect 47: The method in any one of aspects 43-46, wherein the sample comprises blood, serum, plasma, saliva, urine, or a combination thereof.

Aspect 48: The method in any one of aspects 43-46, wherein the sample is saliva.

Aspect 49: The method in any one of aspects 45-48, wherein the disease is diabetes, pre-diabetes, or metabolic syndrome.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperatures, etc.) but some errors and deviations should be accounted for.

Unless indicated otherwise, parts are parts by weight, temperature is in ° C. or is at ambient temperature, and pressure is at or near atmospheric. Numerous variations and combinations of reaction conditions (e.g., component concentrations, desired solvents, solvent mixtures, temperatures, pressures, and other reaction ranges and conditions) can be used to optimize the product purity and yield obtained from the desired process. Only reasonable and routine experimentation will be required to optimize such processes and conditions.

I. Preparation of DNA Construct

The genes described below were assembled in pYES2 plasmid vectors and included an array of promoters and terminators. The full sequence of the DNA-based glucose sensor comprises an arrangement of genes, Gal1 promoters, and CYC1 terminators in the following order: SNF3+CYC1 Terminator+GAL1 Promoter+OGT+CYC1 Terminator+GAL1 Promoter+OGlcNA+CYC1 Terminator+GAL1 Promoter+EGFP as provided in FIGS. 1 and 2.

Sequences included the SNF3 glucose receptor with Genbank accession number XM_001386379.1 (a high affinity glucose receptor already proven as a glucose sensor), O-linked acetylglucosamine transferase (OGT) with Genbank accession number EAX05286.1, 0-GlcNAc selective N-Acetyl-beta-D-glucosaminidase (O-GlcNAc) having Genbank accession number NP_571979.1, and Enhanced Green Fluorescent Protein (EGFP) having Genbank accession number ACV20892.1.

Each gene was PCR amplified using gene-specific overlap primers and assembled sequences were subcloned into a HingIII- and XbaI-digested pYES2 vector. PCR amplified pieces of all fragments were combined by using homologous recombination technology (Gibson Assembly). Clones obtained after transformation were sequenced and analyzed for DNA accuracy. At the completion of PCR of all four targeted genes, homologous recombination of the glucose detection device, and sub-cloning into pYES2 vector, four clones were selected from a transformed plate and processed for full length DNA sequencing. A clone with 100% matching sequence corresponding to the construct design was selected and purified to obtain plasmid construct at a mid-scale purification level. This DNA device will allow the detection of proteins related to the presence of glucose in patient saliva samples as well as to detect existence of glucose itself.

II. Host Cell Purification and Transformation

The biological device was constructed using yeast (S. cerevisiae) cells with a pYES2 plasmid vector. After the vector comprising the DNA construct has been produced, the resulting vector can be incorporated into the host cells using methods known in the art (e.g., Gietz, R. D. and R. H. Schiestl, 2007, *Nature Protocols*, "Quick and easy yeast transformation using the LiAc/SS carrier and DNA/PEG method," Vol. 2, 35-37). INVSc1 competent yeast cells (Invitrogen, Inc.) were used for some transformations. A kit for preparing and transforming INVSc1 cells was purchased from Sigma-Aldrich, Inc., and used according to a protocol provided by the manufacturer. In brief, competent yeast cells were transformed with the DNA construct described herein and selected on synthetic complete (SC) dropout plates (deficient in uracil base). A well isolated clone was picked from the SC plate and preserved in YPD medium containing 15% glycerol for storage at −80° C.

DNA expression and effectiveness of transformation were determined by fluorescence of the transformed cells expressed in fluorescence units (FSUs), according to a protocol provided by the manufacturer, using a 20/20 Luminometer (Promega). The blue fluorescence module (with a 450 nm excitation wavelength and a 600 nm emission wavelength) was used to evaluate the effectiveness of transformation. When no fluorescent reporter protein was assembled, no fluorescence was observed. Plasmid DNA extraction purification, PCR, and gel electrophoresis were also used to confirm transformation.

III. Production of Extracts from the Yeast Device

Transformed *S. cerevisiae* cells were grown in yeast malt broth at 30° C. for 24 hours with an optimum OD of 2.56. An extract was produced from the yeast culture as follows: fermentation was conducted in yeast malt broth mixed with raffinose and galactose for 30° C. for 72 hours. The cultures were then centrifuged at 9,000 rpm for 12 min at 15° C. Pellets were resuspended in 50 mL of sterile deionized water per gram of pellet. The resulting solutions were sonicated 4 times for a total of 2 minutes and 30 seconds and were then again centrifuged at 9,000 rpm for 12 min at 15° C. Supernatants were decanted and filtered with 0.56 μm filters and stored for later use.

IV. Sample Collection and Processing

Saliva samples from fasting patients were collected by having the patients spit in a 3 cm×2 cm collection tube until a total saliva volume of 3 ml, per patient was collected. These samples were mixed with the DNA-based glucose sensors prepared as described above, at different ratios, and subjected to vortexing for 30-50 seconds. Although different ratios of the yeast DNA-based glucose sensors to saliva were used (i.e., 1:1, 2:1, 3:1), the ratio 3:1 showed the best efficacy for each sample (i.e., 190 μL of extract: 30 μL of saliva).

A total volume of 200 μL of saliva alone, DNA-based glucose sensor (DGS) alone, or DGS+saliva was used for fluorescence detection. The detection was performed using a Glomax E-8032: Multi+ Detection System with Instinct™ Software: Base Instrument with Shaking (PROMEGA, Madison, Wisconsin USA) by placing the selected sample on a plate reader, and the samples were exposed to a light source using the blue module (Ex: 490 nm, Em: 510-570 nm). Other excitation wavelengths were tested: however the selected blue light module showed the best consistent results. Fluorescence was determined based on fluorescence units (FSU), and compared to the results of the conventional glycemia tests. The natural inherent fluorescence (1,900 FSU) of the yeast was subtracted from the final fluorescence of each sample.

V. Clinical Analysis of Gylcemia

Glycemia levels for both diabetic and non-diabetic subjects were determined quantitatively following standard in vitro diagnostic protocols using a colorimetric technique in Mindray BS380 equipment. Patients were classified as diabetic, pre-diabetic, or healthy based on guidelines established by the American Diabetes Association and the World Health Organization. Blood glucose ranges (in mg/dL) for each group are provided in Table 4.

TABLE 4

Criteria for Diagnosing Diabetes and Related Conditions

| Condition | Glucose Level (mg/dL) |
| --- | --- |
| Diabetic | >126 |
| Pre-Diabetic | 100-125 |
| Healthy | <100 |

VI. Statistical Analysis

The statistical data was analyzed using Microsoft Excel 2013. An analysis of variance (ANOVA) was performed to determine the equal value of the means in the groups of patients and a linear regression was carried out in order to relate the study variables, in this case glycemia and fluorescence (extract+saliva of patients).

VII. Correlation of Glycemia with Fluorescence

Saliva samples mixed with the extracts produced from the biological device from patients with high clinical glycemia (i.e., diagnosed diabetics) exhibited higher fluorescence intensity than patients with low clinical glycemia after background correction for fluorescence intensity of the extracts themselves (4600 FSU). Based on comparative fluorescence intensity and clinical results, patients were classified into three groups. Results are presented in Table 5.

TABLE 5

Results of fluorescence intensity and glycemia of patients placed in the following groups: Group 1 = Diagnosed Diabetics, Group 2 = Pre-Diabetics, and Group 3 = Healthy

| Patient Age | Gender | DNAGYE + Saliva Initial Fluorescence (FSU) | DNAGYE + Saliva Final Fluorescence (FSU) | Clinical Glycemia (mg/dL) |
| --- | --- | --- | --- | --- |
| Group 1: Diabetics Mean = 6957.143 +/- 822.3 | | | | |
| 36 | Female | 10600 | 6000 | 127 |
| 38 | Female | 11000 | 6400 | 135 |
| 39 | Female | 11200 | 6600 | 129 |
| 31 | Female | 11300 | 6700 | 132 |
| 30 | Male | 11500 | 6900 | 172 |
| 35 | Female | 12300 | 7700 | 152 |
| 44 | Female | 13000 | 8400 | 161 |
| Group 2: Pre-Diabetics. Mean = 5500 +/- 308.22 | | | | |
| 23 | Male | 9700 | 5100 | 117 |
| 42 | Male | 10000 | 5400 | 102 |
| 40 | Female | 10000 | 5400 | 123 |
| 37 | Male | 10300 | 5700 | 125 |
| 45 | Male | 10500 | 5900 | 123 |
| Group 3: Healthy Mean = 3600 +/- 930.6 | | | | |
| 4 | Female | 7000 | 2400 | 65 |
| 18 | Female | 7300 | 2700 | 77 |
| 1 | Female | 7500 | 2900 | 84 |
| 12 | Female | 7500 | 2900 | 84 |
| 3 | Female | 7600 | 3000 | 73 |
| 14 | Female | 7700 | 3100 | 77 |
| 28 | Female | 8600 | 4000 | 84 |
| 24 | Female | 9000 | 4400 | 89 |
| 43 | Female | 9000 | 4400 | 93 |
| 6 | Female | 9500 | 4900 | 97 |
| 25 | Female | 9500 | 4900 | 97 |

Note:
DNAGYE: DNA Glucose Yeast Extract, FSU: Fluorescence units
* "DNAGYE + Saliva Final Fluorescence (FSU)" is the fluorescence background corrected for extract fluorescence (4600 FSU)
Note 2:
Results are based on the mean of number of patients per group, after ANOVA.
Note 3:
p-value = $1.5 \times 10^{-7}$ Fluorescence reading ranges were established based on the laboratory and clinical findings; these are presented in Table 6.

TABLE 6

Ranges of fluorescence intensity and glycemia levels according the patient groups 1, 2, and 3.

| Group | Range of glycemia | Range of Fluorescence (FSU) |
| --- | --- | --- |
| Diabetic | >126 mg/dL | 10,600-13,000 |
| Pre-Diabetic | 100 mg/dL-125 mg/dL | 9,700-10.500 |
| Healthy | <100 mg/dL | 6,000-9,500 |

Throughout this application, various publications are referenced. The disclosures of these publications in their entireties are hereby incorporated by reference into this application in order to more fully describe the compounds, compositions, and methods described herein.

Various modifications and variations can be made to the compounds, compositions, and methods described herein. Other aspects of the compounds, compositions, and methods described herein will be apparent from consideration of the specification and practice of the compounds, compositions, and methods disclosed herein. It is intended that the specification and examples be considered as exemplary.

What is claimed:

1. A DNA construct comprising the following genetic components: (a) a gene that expresses SNF3, (b) a gene that expresses an O-linked N-acetylglucosamine transferase (OGT), (c) a gene that expresses an O-linked N-acetylglucosamine-selective-N-acetyl-β-D-glucosaminidase (OGlcNa), and (d) optionally a gene that expresses a fluorescent reporter protein, wherein the gene that expresses SNF3 has one of SEQ ID NO. 1 or 6-15 or at least 90% identity thereto;

the gene that expresses O-linked N-acetylglucosamine transferase has SEQ ID NO. 2 or at least 90% identity thereto; and the gene that expresses O-linked N-acetylglucosamine-selective-N-acetyl-β-D-glucosaminidase has SEQ ID NO. 3 or at least 90% identity thereto.

2. The DNA construct of claim 1, wherein the construct further comprises a gene that expresses a fluorescent reporter protein.

3. The DNA construct claim 2, wherein the fluorescent reporter protein is a red fluorescent protein, a green fluorescent protein, a cyan fluorescent protein, or a yellow fluorescent protein.

4. The DNA construct of claim 2, wherein the fluorescent reporter protein is enhanced green fluorescent protein.

5. The DNA construct of claim 2, wherein the gene that expresses the reporter protein has SEQ ID NO. 4 or 27 or at least 70% identity thereto.

6. The DNA construct of claim 2, wherein the gene that expresses the reporter protein has SEQ ID NO. 4 or at least 70% identity thereto.

7. The DNA construct of claim 1, further comprising one or more promoters.

8. The DNA construct of claim 7, wherein the promoter is a T3 promoter, a T7 promoter, an iron promoter, a GAL1 promoter, or a glucose promoter.

9. The DNA construct of claim 7, wherein the promoter is a GAL1 promoter.

10. The DNA construct of claim 7, wherein the promoter is a GAL1 promoter, wherein the GAL1 promoter precedes each genetic component.

11. The DNA construct of claim 7, wherein the promoter has one of SEQ ID NO. 16-19 or at least 70% identity thereto.

12. The DNA construct of claim 1, further comprising at least one terminator.

13. The DNA construct of claim 12, wherein the terminator is a T7 terminator or a CYC1 terminator.

14. The DNA construct of claim 12, wherein the terminator is a CYC1 terminator, wherein the CYC1 terminator follows each genetic component.

15. The DNA construct of claim 12, wherein the terminator has SEQ ID NO. 20 or at least 70% identity thereto.

16. The DNA construct of claim 1, further comprising a gene that expresses a riboswitch.

17. The DNA construct of claim 16, wherein the riboswitch has one of SEQ ID NO. 21-23 or at least 70% identity thereto.

18. The DNA construct of claim 1, further comprising a gene that expresses a ribosomal binding site.

19. The DNA construct of claim 18, wherein the ribosomal binding site has SEQ ID NO. 24-26 or at least 70% identity thereto.

20. The DNA construct of claim 1, wherein the DNA construct comprises from 5' to 3' the following genetic components in the following order: (a) a gene that expresses SNF3, (b) a gene that expresses O-linked N-acetylglucosamine transferase, and (c) a gene that expresses O-linked N-acetylglucosamine-selective-N-acetyl-β-D-glucosaminidase.

21. The DNA construct of claim 1, wherein the DNA construct comprises from 5' to 3' the following genetic components in the following order: (a) a gene that expresses SNF3, (b) a gene that expresses O-linked N-acetylglucosamine transferase, (c) a gene that expresses O-linked N-acetylglucosamine-selective-N-acetyl-β-D-glucosaminidase, and (d) a gene that expresses a reporter protein.

22. The DNA construct of claim 1, wherein the DNA construct comprises from 5' to 3' the following genetic components in the following order: (a) a gene that expresses SNF3, (b) a CYC1 terminator, (c) a GAL1 promoter, (d) a gene that expresses O-linked N-acetylglucosamine transferase, (e) a CYC1 terminator, (f) a GAL1 promoter, (g) a gene that expresses O-linked N-acetylglucosamine-selective-N-acetyl-β-D-glucosaminidase, (h) a CYC1 terminator, (i) a GAL1 promoter, and (j) a gene that expresses a reporter protein.

23. The DNA construct of claim 1, wherein the DNA construct comprises from 5' to 3' the following genetic components in the following order: (a) a gene that expresses SNF3 having SEQ ID NO. 1 or at least 90% identity thereto, (b) a CYC1 terminator, (c) a GAL1 promoter, (d) a gene that expresses O-linked N-acetylglucosamine transferase having SEQ ID NO. 2 or at least 90% identity thereto, (e) a CYC1 terminator, (f) a GAL1 promoter, (g) a gene that expresses O-linked N-acetylglucosamine-selective-N-acetyl-β-D-glucosaminidase having SEQ ID NO. 3 or at least 90% identity thereto, (h) a CYC1 terminator, (i) a GAL1 promoter, and (j) a gene that expresses a reporter protein having SEQ ID NO. 4 or at least 70% identity thereto.

24. The DNA construct of claim 1, wherein the DNA construct has SEQ ID NO. 5 or at least 70% identity thereto.

25. The DNA construct of claim 1, wherein the DNA construct further comprises a gene that confers resistance to an antibiotic.

26. The DNA construct of claim 25, wherein the antibiotic comprises tetracycline, neomycin, kanamycin, ampicillin, hygromycin, chloramphenicol, amphotericin B, bacitracin, carbapenam, cephalosporin, ethambutol, fluoroquinolones, isoniazid, methicillin, oxacillin, vancomycin, streptomycin, quinolones, rifampin, rifampicin, sulfonamides, cephalothin, erythromycin, gentamycin, penicillin, other commonly-used antibiotics, or a combination thereof.

27. A vector comprising the DNA construct of claim 1.

28. The vector of claim 27, wherein the vector is a plasmid.

29. The vector of claim 28, wherein the plasmid is pWLneo, pSV2cat, pOG44, pXT1, pSG, pSVK3, pBSK, pBSKII, pYES, pYES2, pUC, pUC19, or pETDuet-1.

30. The vector of claim 28, wherein the plasmid is pYES2.

31. A biological device comprising host cells transformed with the DNA construct of claim 1.

32. The biological device of claim 31, wherein the host cells comprise fungi.

33. The biological device of claim 32, wherein the fungi comprise yeast.

34. The biological device of claim 33, wherein the yeast comprise *S. cerevisiae*.

* * * * *

SEQUENCE LISTING

<160> NUMBER OF SEQ ID NOS: 27

<210> SEQ ID NO 1
<211> LENGTH: 2244
<212> TYPE: DNA
<213> ORGANISM: Pichia stipitis

<400> SEQUENCE: 1

```
atgtggaaat ttctagaagc tctactttac gacaacacca tcgaagaaga atactacagg      60
aaaatccgtc aaaagtcctc ctccaagtcg gctgtaatcg taggtcttgt agctgccgtg     120
ggaggctttt tgtatgggta cgatacggga ctcatcaacg acttgctaga aatgagatac     180
gtctacgaaa actttccaga aaatctgcat tcgttcacat cacatgaacg agcgttgatt     240
acggctgtgt tatcgctcgg aacattcata ggagctctca tagcgcctct tatctccgac     300
aactatggcc ggaagttttc catcattgtc tcttccggtc tcattttcaa cgcaggcaac     360
attttgcaaa tcgcatcaac aaacgtagca ttgctttgcg ttggtagagc gatctcgggt     420
gtatctgtag gcattctttc ggccattgta cccttgtacc aagctgaagc ttctcccaaa     480
tgggtcagag gttccgtcgt tttcacatat caatgggcca ttacttgggg cttgttgata     540
gcgagtgccg tctgtcaagg cactcgaaaa atgaccaatt ctggctcata tcggatcccc     600
gtgggcctcc agtttctctg ggctcttatc ttgtacacgg ggatgctttt cttgcccgaa     660
agtccccgtt attatgttca aaaagacgat cttcagaaag ctctagatag tttgtcgaag     720
ttgcgaaagt tgccccccaga cgacgctgat tgatagagg agttggtgga aatcaaggct     780
aactacgact acgagttgtc gtatggtaag accaactatc ttgattgctt ccgtagtgga     840
ggaggaagac acaagcaggt gttgcgaatg ttcactggaa tcggtgctca actctttcag     900
cagtgttcag gcatcaactt catcttctac tatggtgtca acttcttctc cagcaccggc     960
atccagaact tttacatcat gtccttcgtg acgtatttgg tcaacactat cttcacaatc    1020
cccggaataa ttctagtgga tacgataggc aggcgacagt tgctcctatg gggtggcgta    1080
ggcatgtcta ccgcgaactt cataattgcg attacgggag tcagtatctc cagtaaggaa    1140
accagttcga ttctaagcgt ctgtttttcg tgtgtgttca tagcgttttt cgccagttcg    1200
tggggtggat gtgtatgggc actcacttct gatatatacg gtattagtat cagacagaga    1260
gccatatcca tcactacagc cacgaactgg ttggtcaact tcatctttgc ctacataaca    1320
ccgtatctca tcgatacggg acaccatact gcagctatag gaaacaaaat cttctttatc    1380
tggggaggtt gtaacgctgc cggtgtcgtt ttcgtctact tcactgtcta cgaaacaaag    1440
ggattgaagt tggaggaaat tgattatatg tacgctcatt gtgacaatgc gagaaagtcc    1500
accgagttca gtcgaccaa aatcgattac actagattgg acgagaacta caacgctgta    1560
ccctgggatc ctccttatcc atcaacaacg agctcatcgc ctccttctaa catcaacgag    1620
```

| | |
|---|---|
| aaggaccttt catcttctga tcccaaccaa gacgtcaatg tacatagtga caacaacgag | 1680 |
| tttgttccat tgtacaacaa caaaaaactt ccaataatc ctacaaacac caacaaaaac | 1740 |
| gacatcacca tcattcccta caacaatatc attctgccgt cgttatcatc gaactccgag | 1800 |
| ccctcttctg ctgcttcgtc aattctcaac aacagattcc accacaactc tgtctcgact | 1860 |
| acaaacaacg tctctgtatc tacatctaac cctggccaat cttctggtca aggtacagct | 1920 |
| tccaacgact acttgctgta tttggatagt ttgaagtctg agtacggaag tccacctcac | 1980 |
| tacaataacg acacactaca ccagcagcac accaaccaat cgaactccaa gggttctgct | 2040 |
| acagacagaa acagcagcat cactgctagc aacattcacc atactcatag caacatcacc | 2100 |
| agcaacatta ataaccataa tagtaataac attaataaca gtataaccaa caattcgacc | 2160 |
| acgattattg ccacgccata cttcaaccag cctccaccag actcttccga tgaagaagac | 2220 |
| gaagacgagg acgaagaaga atag | 2244 |

<210> SEQ ID NO 2
<211> LENGTH: 3141
<212> TYPE: DNA
<213> ORGANISM: Urocitellus parryii

<400> SEQUENCE: 2

| | |
|---|---|
| atggcttcat ctgttggaaa tgttgccgat tctactgaac ctaccaagag aatgttatca | 60 |
| tttcaaggat tagctgaatt agcccatagg gaataccaag ccggtgactt tgaagctgcc | 120 |
| gaaagacact gtatgcaatt gtggagacag gagccagaca atacaggcgt gttattgttg | 180 |
| ttgtcatcta ttcatttcca atgtagaagg ttggatagat ctgctcactt tagtactttg | 240 |
| gcaatcaaac agaatccatt gttagctgaa gcatattcca acttaggtaa cgtctataag | 300 |
| gaaagaggtc aattgcagga agccatcgag cattaccgtc atgcattaag attgaagccc | 360 |
| gatttcatcg atggttacat taacttagca gcagccttgg ttgcagcagg agatatggaa | 420 |
| ggtgcagtcc aagcctatgt ctccgcatta cagtataacc ctgacttgta ctgtgttaga | 480 |
| tctgatttgg gaaacttatt gaaggcattg ggaaggttgg aagaggcaaa ggcttgctac | 540 |
| ttgaaggcca tagaaactca accaaacttc gcagtcgcat ggtcaaactt gggttgcgtg | 600 |
| ttcaacgcac aaggtgaaat ctggttagct atccaccatt tcgagaaagc agttacttta | 660 |
| gatcccaatt tcttggatgc ctacatcaat ttgggaaatg tgttaaagga ggcaaggatc | 720 |
| ttcgaccgtg ctgtcgcagc atacttaagg gctttgtctt taagtccaaa ccacgcagtt | 780 |
| gtacatggca acttggcttg tgtctactat gagcaaggat tgattgactt agctattgat | 840 |
| acctatcgta gggccattga attacagcca cactttcctg acgcttactg caacttggct | 900 |
| aatgccttga aggagaaggg atctgtggca gaggctgagg attgctacaa caccgcattg | 960 |
| aggttatgtc caacacatgc agattcctta acaatttgg ccaatatcaa gcgtgaacag | 1020 |
| ggtaacatcg aagaagccgt cagattgtat agaaaggcct tagaggtctt tcctgaattt | 1080 |
| gctgctgccc attccaactt agcaagtgtg ttacagcagc aaggcaagtt gcaagaagcc | 1140 |
| ttaatgcact ataaggaagc aatcagaata agtcctacct tgccgatgc ttattccaat | 1200 |
| atgggtaata ctttgaagga aatgcaggat gtccaaggtg ccttacaatg ttataccagg | 1260 |
| gcaattcaaa tcaatcctgc tttcgcagat gctcattcta acttggcatc catccataaa | 1320 |
| gattcaggca acataccaga ggccatcgcc tcttatcgta cagccttgaa gttgaagcct | 1380 |
| gatttcccag atgcctattg caacttggcc cattgtttgc aaattgtatg tgattggaca | 1440 |
| gattacgatg aaagaatgaa gaagttggtg agtatcgttg ctgaccaatt agagaagaac | 1500 |

```
agattgccat cagttcaccc tcatcactct atgttgtacc cattgagtca tggtttcaga    1560
aaggcaattg ctgaaaggca tggcaatttg tgtttggaca agatcaatgt cttacataag    1620
cctccatacg aacatcctaa ggatttgaaa ttgtcagatg gaaggttgcg tgtcggatat    1680
gtttcttctg atttcggtaa tcatccaacc agtcacttaa tgcagagtat ccctggtatg    1740
cataatcccg acaaattcga agtcttctgt tatgccttaa gtccagatga cggcaccaat    1800
ttcagagtga aagttatggc tgaagctaat catttcattg atttgagtca aattccttgt    1860
aacggtaaag ccgcagatag gatacaccaa gacggcattc atatcttggt caatatgaac    1920
ggatacacaa agggtgctag aaacgagttg tttgctttaa gaccagcacc tatacaagca    1980
atgtggttag gctatccagg cacttcaggt gctttgttca tggactacat cataaccgac    2040
caagaaactt ctcccgcaga ggttgctgaa caatacagtg agaagttggc ttacatgcca    2100
catactttct tcattggtga tcatgccaat atgttcccac atttgaagaa gaaagcagtc    2160
atagatttca atctaatgg acatatctat gataacagaa tagtgttaaa cggtattgat    2220
ttgaaagcat tcttggattc cttacctgat gttaagattg ttaagatgaa gtgtccagat    2280
ggtggcgaca acgctgattc ttctaatacc gctttgaata tgcctgtgat cccaatgaat    2340
actatcgccg aggcagttat cgaaatgatc aatagaggcc aaattcaaat cacaatcaat    2400
ggattctcta tttctaacgg tttagcaaca acacagataa acaacaaagc tgctaccgga    2460
gaagaggtgc ctaggaccat tatcgttact acaagatccc agtatggttt acctgaggac    2520
gctatcgtgt actgcaactt caatcagtta tacaagatcg atccttcaac cttacagatg    2580
tgggctaaca tcttgaagag ggttcccaat tcagtattgt ggttgttaag atttcccgca    2640
gtcggtgagc ctaacattca acagtacgct cagaatatgg gcttacctca gaatagaatc    2700
atattctctc ctgtagctcc aaaggaagaa catgtcagac gtggtcaatt ggccgatgtg    2760 tgttggaca ctcccttgtg caacggacac accactggta tggatgtctt gtgggcaggc    2820
actcctatgg taactatgcc tggcgaaaca ttggctagta gagttgcagc tagtcaattg    2880
acatgcttag gttgcttaga gttgattgca aagaacagac aagaatacga agatattgct    2940
gtcaagttag gtactgattt ggagtacttg aagaaggtta gaggtaaggt ctggaaacaa    3000
agaattagta gtccattgtt caacaccaaa caatacacaa tggaattaga aagattgtac    3060
ttacaaatgt gggagcacta tgccgcaggt aacaaacctg accacatgat caaaccagtt    3120
gaagtaaccg aatccgctta a                                              3141

<210> SEQ ID NO 3
<211> LENGTH: 2751
<212> TYPE: DNA
<213> ORGANISM: Rattus norvegicus

<400> SEQUENCE: 3
atggtacaga aggagagtca agctgcatta gaagaaaggg aatcagaaag gaatgcaaac      60
ccagcatccg ttagtggcgc atctttggaa ccatctgccg ctcctgctcc aggtgaagat     120
aatccatcag gtgcaggcgc tgccgcagga actggagccg caggaggagc caggagattc     180
ttatgtggtg tcgtagaagg cttctacggc agaccctggg ttatgaacag agaaaaggag     240
ttgttcagaa gattgcagaa gtgggagttg aatacttact tgtatgctcc taaggatgac     300
tacaagcata gaatgttctg gcgtgaaatg tattctgtgg aagaagctga acagttgatg     360
acattgatat cagctgcaag agaatacgaa attgagttta tctatgcaat ctctccaggc     420
```

-continued

```
ttggacatta ccttctccaa cccaaaggag gtcagtacct taaagcgtaa gttggatcaa      480
gtgtctcaat tcggatgtag aagtttcgcc ttattgttcg atgacatcga ccacaacatg      540
tgcgctgctg acaaagaagt gttctcttct ttcgcacatg cacaggtgtc catcacaaat      600
gaaatctatc aatacttagg agaaccagaa acattcttat tctgcccaac agagtattgt      660
ggcactttct gttatccatc cgtcagtcaa agtccctatt tgagaactgt gggtgagaag      720
ttattgccag gaatcgaagt attgtggact ggacctaaag ttgtgtctaa agaaattcca      780
gtggagtcta ttgaagaagt atcaaagatc ataaagagag cacctgttat ctgggataac      840
attcacgcta acgattacga tcagaagaga ttgttcttgg gtccttacaa aggtaggtct      900
accgagttga ttccaaggtt gaaaggcgta ttgaccaatc ctaactgtga atttgaagca      960
aactatgtag ccattcacac attggctact tggtataagt ccaacatgaa cggcgtacgt     1020
aaagatgttg ttatgaccga ttccgaagat tccacagtat ctatccagat caaattggag     1080
aacgaaggta gtgacgaaga tatagagact gatgtgttgt actctcctca gatggcattg     1140 aaaattggcct tgactgaatg gttgcaggaa tttggtgtgc cacaccaata ctcatcaaga     1200
caagtcgctc attccggagc taagacatct gttgtggatg gcacacccctt ggtggcagca     1260 ccatctttga tgcaacaac agttgttact acagtttatc aagaacccat tatgtcacag     1320
ggtgctgctt tatccggtga gccctctgct ttaactaaag aagaagagaa gaaacaacct     1380
gatgaggaac caatggatat ggtggttgag aagcaagaag agtctgaaca caagtccgat     1440
aaccagatct taacagagat tgtcgaagct aagatggcag aagaattgaa acctatggat     1500
accgataaag aatctattgc cgaaagtaag agtccagaaa tgagtatgca agaagactgt     1560
atcaatgata ttgcacccat gcagactgat gaacaagcca ataaggaaca gttcgttcca     1620
ggcccaaatg agaagccttt gtatgcagca gaacctgtca cttttggaaga cttgcaattg     1680 ttagcagatt tgttctactt accatacgag cacggtccta agggtgcaca aatgttaaga     1740
gaatttcaat ggtaagagc taattcatct gtcgtgtcag taaactgtaa aggtaaggat     1800
agtgagaaga ttgaagagtg gagatcaaga gcagccaagt tcgaggaaat gtgtgcttta     1860
gtcatgggca tgtttaccag attgtctaat tgcgctaata gaactatctt gtatgatatg     1920
tattcatacg tttgggacat aaagtccatt atgtctatgg tcaaatcatt tgtacaatgg     1980
ttgggttgta gaagtcactc ttctgcccag ttcttgattg gtgaccaaga gccttgggcc     2040
tttagaggcg gattggcagg cgaatttcaa cgtttgttac ctattgacgg tgctaatgat     2100
ttgttctttc agccaccacc tttaactcct acctctaaag tctatactat taggccatac     2160
tttcccaaag acgaagccag tgtgtataag atctgtagag agatgtacga tgatggtgta     2220
ggtttgccat ttcaatccca accagacttg ataggtgaca aattggtagg aggttttgttg     2280 tctttatctt tagactattg cttcgtgtta gaggatgagg atggtatttg cggttatgcc     2340
ttaggaactg tagatgtaac tcctttcata aagaaatgca agatatcttg gatacctttc     2400
atgcaagaga agtatactaa accaaatggt gataaggaat tgagtgaagc tgagaagatc     2460
atgttatctt tccatgaaga acaagaagta ttgccagaga cattcttggc caatttccct     2520
tctttgataa agatggatat acataagaag gtgactgatc cttcagtagc caaatctatg     2580
atggcctgct tattgtcatc cttaaaggcc aatggatcaa gaggtgcttt ctgtgaggtg     2640
aggccagatg acaagagaat cttagagttc tatagtaagt taggttgttt cgagattgct     2700
aagatggaag gtttccctaa ggacgtcgtg atcttgggaa ggtctttgta a              2751
```

```
<210> SEQ ID NO 4
<211> LENGTH: 717
<212> TYPE: DNA
<213> ORGANISM: Artificial sequence
<220> FEATURE:
<223> OTHER INFORMATION: Synthetic construct

<400> SEQUENCE: 4
atgtctaaag gtgaagaatt attcactggt gttgtcccaa ttttggttga attagatggt      60
gatgttaatg gtcacaaatt ttctgtctcc ggtgaaggtg aaggtgatgc tacttacggt     120
aaattgacct taaaatttat ttgtactact ggtaaattgc cagttccatg gccaacctta     180
gtcactactt tcggttatgg tgttcaatgt tttgctagat acccagatca tatgaaacaa     240
catgactttt tcaagtctgc catgccagaa ggttatgttc aagaaagaac tatttttttc     300
aaagatgacg gtaactacaa gaccagagct gaagtcaagt ttgaaggtga taccttagtt     360
aatagaatcg aattaaaagg tattgatttt aaagaagatg gtaacatttt aggtcacaaa     420
ttggaataca ctataactc tcacaatgtt tacatcatgg ctgacaaaca aaagaatggt     480
atcaaagtta acttcaaaat tagacacaac attgaagatg gttctgttca attagctgac     540
cattatcaac aaaatactcc aattggtgat ggtccagtct tgttaccaga caaccattac     600
ttatccactc aatctgcctt atccaaagat ccaaacgaaa agagagacca catggtcttg     660
ttagaatttg ttactgctgc tggtattacc catggtatgg atgaattgta caaataa        717

<210> SEQ ID NO 5
<211> LENGTH: 16754
<212> TYPE: DNA
<213> ORGANISM: Artificial sequence
<220> FEATURE:
<223> OTHER INFORMATION: Synthetic construct

<400> SEQUENCE: 5
acggattaga agccgccgag cgggtgacag ccctccgaag gaagactctc ctccgtgcgt      60
cctcgtcttc accggtcgcg ttcctgaaac gcagatgtgc ctcgcgccgc actgctccga     120
acaataaaga ttctacaata ctagctttta tggttatgaa gaggaaaaat tggcagtaac     180
ctggccccac aaaccttcaa atgaacgaat caaattaaca accataggat gataatgcga     240
ttagtttttt agccttattt ctggggtaat taatcagcga agcgatgatt tttgatctat     300
taacagatat ataaatgcaa aaactgcata accactttaa ctaatacttt caacattttc     360
ggtttgtatt acttcttatt caaatgtaat aaaagtatca acaaaaaatt gttaatatac     420
ctctatactt taacgtcaag gagaaaaaac cccggatcgg actactagca gctgtaatac     480
gactcactat agggaatatt aagcttgcca ccggtaccat gtggaaattt ctagaagctc     540
tactttacga caacaccatc gaagaagaat actacaggaa aatccgtcaa aagtcctcct     600
ccaagtcggc tgtaatcgta ggtcttgtag ctgccgtggg aggcttttg tatgggtacg     660 atacgggact catcaacgac ttgctagaaa tgagatacgt ctacgaaaac tttccagaaa     720
atctgcattc gttcacatca catgaacgag cgttgattac ggctgtgtta tcgctcggaa     780
cattcatagg agctctcata gcgcctctta tctccgacaa ctatggccgg aagttttcca     840
tcattgtctc ttccggtctc attttcaacg caggcaacat tttgcaaatc gcatcaacaa     900
acgtagcatt gctttgcgtt ggtagagcga tctcgggtgt atctgtaggc attctttcgg     960
ccattgtacc cttgtaccaa gctgaagctt ctcccaaatg gtcagaggt tccgtcgttt     1020 tcacatatca atgggccatt acttgggggct tgttgatagc gagtgccgtc tgtcaaggca    1080
```

```
ctcgaaaaat gaccaattct ggctcatatc ggatccccgt gggcctccag tttctctggg    1140
ctcttatctt gtacacgggg atgcttttct tgcccgaaag tccccgttat tatgttcaaa    1200
aagacgatct tcagaaagct ctagatagtt tgtcgaagtt gcgaaagttg ccccagacg     1260 acgctgattt gatagaggag ttggtggaaa tcaaggctaa ctacgactac gagttgtcgt    1320
atggtaagac caactatctt gattgcttcc gtagtggagg aggaagacac aagcaggtgt    1380
tgcgaatgtt cactggaatc ggtgctcaac tctttcagca gtgttcaggc atcaacttca    1440
tcttctacta tggtgtcaac ttcttctcca gcaccggcat ccagaacttt tacatcatgt    1500
ccttcgtgac gtatttggtc aacactatct tcacaatccc cggaataatt ctagtggata    1560
cgataggcag gcgacagttg ctcctatggg gtggcgtagg catgtctacc gcgaacttca    1620
taattgcgat tacgggagtc agtatctcca gtaaggaaac cagttcgatt ctaagcgtct    1680 gttttcgtg tgtgttcata gcgttttcg ccagttcgtg gggtggatgt gtatgggcac      1740
tcacttctga tatatacggt attagtatca gacagagagc catatccatc actacagcca    1800
cgaactggtt ggtcaacttc atcttgcct acataacacc gtatctcatc gatacgggac     1860
accatactgc agctatagga aacaaaatct tctttatctg gggaggttgt aacgctgccg    1920
gtgtcgtttt cgtctacttc actgtctacg aaacaaaggg attgaagttg gaggaaattg    1980
attatatgta cgctcattgt gacaatgcga gaaagtccac cgagttcaag tcgaccaaaa    2040
tcgattacac tagattggac gagaactaca acgctgtacc ctgggatcct ccttatccat    2100
caacaacgag ctcatcgcct ccttctaaca tcaacgagaa ggacctttca tcttctgatc    2160
ccaaccaaga cgtcaatgta catagtgaca acaacgagtt tgttccattg tacaacaaca    2220
aaaaacttcc aaataatcct acaaacacca acaaaaacga catcaccatc attccctaca    2280
acaatatcat tctgccgtcg ttatcatcga actccgagcc ctcttctgct gcttcgtcaa    2340
ttctcaacaa cagattccac cacaactctg tctcgactac aaacaacgtc tctgtatcta    2400
catctaaccc tggccaatct tctggtcaag gtacagcttc caacgactac ttgctgtatt    2460
tggatagttt gaagtctgag tacggaagtc cacctcacta caataacgac acactacacc    2520
agcagcacac caaccaatcg aactccaagg gttctgctac agacagaaac agcagcatca    2580
ctgctagcaa cattcaccat actcatagca acatcaccag caacattaat aaccataata    2640
gtaataacat taataacagt ataaccaaca attcgaccac gattattgcc acgccatact    2700
tcaaccagcc tccaccagac tcttccgatg aagaagacga agacgaggac gaagaagaat    2760
aggtttaaac tcatgtaatt agttatgtca cgcttacatt cacgccctcc ccccacatcc    2820
gctctaaccg aaaaggaagg agttagacaa cctgaagtct aggtccctat ttattttttt    2880
atagttatgt tagtattaag aacgttattt atatttcaaa ttttttctttt ttttctgtac    2940 agacgcgtgt acgcatgtaa cattatactg aaaaccttgc ttgagaaggt tttgggacgc    3000
tcgaaggctt taatttgccg gattagaagc cgccgagcgg gtgacagccc tccgaaggaa    3060
gactctcctc cgtgcgtcct cgtcttcacc ggtcgcgttc ctgaaacgca gatgtgcctc    3120
gcgccgcact gctccgaaca ataaagattc tacaatacta gcttttatgg ttatgaagag    3180
gaaaaattgg cagtaacctg gccccacaaa ccttcaaatg aacgaatcaa attaacaacc    3240
ataggatgat aatgcgatta gttttttagc cttatttctg gggtaattaa tcagcgaagc    3300
gatgattttt gatctattaa cagatatata aatgcaaaaa ctgcataacc actttaacta    3360
atactttcaa cattttcggt ttgtattact tcttattcaa atgtaataaa agtatcaaca    3420
aaaaattgtt aatataccct ctatactttaa cgtcaaggag gtcgacgcca ccatggcttc    3480
```

```
atctgttgga aatgttgccg attctactga acctaccaag agaatgttat catttcaagg    3540
attagctgaa ttagcccata gggaatacca agccggtgac tttgaagctg ccgaaagaca    3600
ctgtatgcaa ttgtggagac aggagccaga caatacaggc gtgttattgt tgttgtcatc    3660
tattcatttc aatgtagaa ggttggatag atctgctcac tttagtactt tggcaatcaa     3720
acagaatcca ttgttagctg aagcatattc caacttaggt aacgtctata aggaaagagg    3780
tcaattgcag gaagccatcg agcattaccg tcatgcatta agattgaagc ccgatttcat    3840
cgatggttac attaacttag cagcagcctt ggttgcagca ggagatatgg aaggtgcagt    3900
ccaagcctat gtctccgcat tacagtataa ccctgacttg tactgtgtta gatctgattt    3960
gggaaactta ttgaaggcat tgggaaggtt ggaagaggca aaggcttgct acttgaaggc    4020
catagaaact caaccaaact tcgcagtcgc atggtcaaac ttgggttgcg tgttcaacgc    4080
acaaggtgaa atctggttag ctatccacca tttcgagaaa gcagttactt tagatcccaa    4140
tttcttggat gcctacatca atttgggaaa tgtgttaaag gaggcaagga tcttcgaccg    4200
tgctgtcgca gcatacttaa gggctttgtc tttaagtcca aaccacgcag ttgtacatgg    4260
caacttggct tgtgtctact atgagcaagg attgattgac ttagctattg atacctatcg    4320
tagggccatt gaattacagc cacactttcc tgacgcttac tgcaacttgg ctaatgcctt    4380
gaaggagaag ggatcgtgtg gcagaggctga ggattgctac aacaccgcat tgaggttatg   4440
tccaacacat gcagattcct taaacaattt ggccaatatc aagcgtgaac agggtaacat    4500
cgaagaagcc gtcagattgt atagaaaggc cttagaggtc tttcctgaat ttgctgctgc    4560
ccattccaac ttagcaagtg tgttacagca gcaaggcaag ttgcaagaag ccttaatgca    4620
ctataaggaa gcaatcagaa taagtcctac ctttgccgat gcttattcca atatgggtaa    4680
tactttgaag gaaatgcagg atgtccaagg tgccttacaa tgttatacca gggcaattca    4740
aatcaatcct gctttcgcag atgctcattc taacttggca tccatccata aagattcagg    4800
caacatacca gaggccatcg cctcttatcg tacagccttg aagttgaagc ctgatttccc    4860
agatgcctat tgcaacttgg cccattgttt gcaaattgta tgtgattgga cagattacga    4920
tgaaagaatg aagaagttgg tgagtatcgt tgctgaccaa ttagaagaga acagattgcc    4980
atcagttcac cctcatcact ctatgttgta cccattgagt catggtttca gaaaggcaat    5040
tgctgaaagg catggcaatt tgtgtttgga caagatcaat gtcttacata gcctccata    5100 cgaacatcct aaggatttga aattgtcaga tggaaggttg cgtgtcggat atgtttcttc    5160
tgatttcggt aatcatccaa ccagtcactt aatgcagagt atccctggta tgcataatcc    5220
cgacaaattc gaagtcttct gttatgcctt aagtccagat gacggcacca atttcagagt    5280
gaaagttatg gctgaagcta atcatttcat tgatttgagt caaattcctt gtaacggtaa    5340
agccgcagat aggatacacc aagacggcat tcatatcttg gtcaatatga acggatacac    5400
aaagggtgct agaaacgagt tgtttgcttt aagaccagca cctatacaag caatgtggtt    5460
aggctatcca ggcacttcag gtgctttgtt catggactac atcataaccg accaagaaac    5520
ttctcccgca gaggttgctg aacaatacag tgagaagttg gcttacatgc cacatacttt    5580
cttcattggt gatcatgcca atatgttccc acatttgaag aagaaagcag tcatagattt    5640
caaatctaat ggacatatct atgataacag aatagtgtta aacggtattg atttgaaagc    5700
attcttggat tccttacctg atgttaagat tgttaagatg aagtgtccag atggtggcga    5760
caacgctgat tcttctaata ccgctttgaa tatgcctgtg atcccaatga atactatcgc    5820
```

```
cgaggcagtt atcgaaatga tcaatagagg ccaaattcaa atcacaatca atggattctc    5880
tatttctaac ggtttagcaa caacacagat aaacaacaaa gctgctaccg agaagaggt     5940 gcctaggacc attatcgtta ctacaagatc ccagtatggt ttacctgagg acgctatcgt    6000
gtactgcaac ttcaatcagt tatacaagat cgatccttca accttacaga tgtgggctaa    6060
catcttgaag agggttccca attcagtatt gtggttgtta agatttcccg cagtcggtga    6120
gcctaacatt caacagtacg ctcagaatat gggcttacct cagaatagaa tcatattctc    6180
tcctgtagct ccaaaggaag aacatgtcag acgtggtcaa ttggccgatg tgtgtttgga    6240
cactcccttg tgcaacggac acaccactgg tatggatgtc ttgtgggcag gcactcctat    6300
ggtaactatg cctggcgaaa cattggctag tagagttgca gctagtcaat tgacatgctt    6360
aggttgctta gagttgattg caagaacag acaagaatac gaagatattg ctgtcaagtt     6420
aggtactgat ttggagtact tgaagaaggt tagaggtaag gtctggaaac aaagaattag    6480
tagtccattg ttcaacacca aacaatacac aatggaatta gaaagattgt acttacaaat    6540
gtgggagcac tatgccgcag gtaacaaacc tgaccacatg atcaaaccag ttgaagtaac    6600
cgaatccgct taattaatca tgtaattagt tatgtcacgc ttacattcac gccctccccc    6660
cacatccgct ctaaccgaaa aggaaggagt tagacaacct gaagtctagg tccctattta    6720 ttttttata gttatgttag tattaagaac gttatttata tttcaaattt ttcttttttt     6780
tctgtacaga cgcgtgtacg catgtaacat tatactgaaa accttgcttg agaaggtttt    6840
gggacgctcg aaggctttaa tttgccggat tagaagccgc cgagcgggtg acagccctcc    6900
gaaggaagac tctcctccgt gcgtcctcgt cttcaccggt cgcgttcctg aaacgcagat    6960
gtgcctcgcg ccgcactgct ccgaacaata aagattctac aatactagct tttatggtta    7020
tgaagaggaa aaattggcag taacctggcc ccacaaacct tcaaatgaac gaatcaaatt    7080
aacaaccata ggatgataat gcgattagtt ttttagcctt atttctgggg taattaatca    7140
gcgaagcgat gattttgat ctattaacag atatataaat gcaaaaactg cataaccact     7200
ttaactaata ctttcaacat tttcggtttg tattacttct tattcaaatg taataaaagt    7260
atcaacaaaa aattgttaat atacctctat actttaacgt caaggagctc gaggccacca    7320
tggtacagaa ggagagtcaa gctgcattag aagaagggga atcagaaagg aatgcaaacc    7380
cagcatccgt tagtggcgca tctttggaac catctgccgc tcctgctcca ggtgaagata    7440
atccatcagg tgcaggcgct gccgcaggaa ctggagccgc aggaggagcc aggagattct    7500
tatgtggtgt cgtagaaggc ttctacggca gaccctgggt tatggaacag agaaaggagt    7560
tgttcagaag attgcagaag tgggagttga atacttactt gtatgctcct aaggatgact    7620
acaagcatag aatgttctgg cgtgaaatgt attctgtgga agaagctgaa cagttgatga    7680
cattgatatc agctgcaaga gaatacgaaa ttgagtttat ctatgcaatc tctccaggct    7740
tggacattac cttctccaac ccaaaggagg tcagtacctt aaagcgtaag ttggatcaag    7800
tgtctcaatt cggatgtaga agtttcgcct tattgttcga tgcatcgac cacaacatgt     7860 gcgctgctga caagaagtg ttctcttctt tcgcacatgc acaggtgtcc atcacaaatg     7920
aaatctatca atacttagga gaaccagaaa cattcttatt ctgcccaaca gagtattgtg    7980
gcactttctg ttatccatcc gtcagtcaaa gtccctattt gagaactgtg ggtgagaagt    8040
tattgccagg aatcgaagta ttgtggactg gacctaaagt tgtgtctaaa gaaattccag    8100
tggagtctat tgaagaagta tcaaagatca taaagagagc acctgttatc tgggataaca    8160
ttcacgctaa cgattacgat cagaagagat tgttcttggg tccttacaaa ggtaggtcta    8220
```

```
ccgagttgat tccaaggttg aaaggcgtat tgaccaatcc taactgtgaa tttgaagcaa   8280
actatgtagc cattcacaca ttggctactt ggtataagtc caacatgaac ggcgtacgta   8340
aagatgttgt tatgaccgat tccgaagatt ccacagtatc tatccagatc aaattggaga   8400
acgaaggtag tgacgaagat atagagactg atgtgttgta ctctcctcag atggcattga   8460
aattggcctt gactgaatgg ttgcaggaat ttggtgtgcc acaccaatac tcatcaagac   8520
aagtcgctca ttccggagct aagacatctg ttgtggatgg cacacccttg gtggcagcac   8580
catctttgaa tgcaacaaca gttgttacta cagtttatca agaacccatt atgtcacagg   8640
gtgctgcttt atccggtgag ccctctgctt taactaaaga agaagagaag aaacaacctg   8700
atgaggaacc aatggatatg gtggttgaga agcaagaaga gtctgaacac aagtccgata   8760
accagatctt aacagagatt gtcgaagcta agatggcaga agaattgaaa cctatggata   8820
ccgataaaga atctattgcc gaaagtaaga gtccagaaat gagtatgcaa gaagactgta   8880
tcaatgatat tgcacccatg cagactgatg aacaagccaa taaggaacag ttcgttccag   8940
gcccaaatga gaagcctttg tatgcagcag aacctgtcac tttggaagac ttgcaattgt   9000
tagcagattt gttctactta ccatacgagc acggtcctaa gggtgcacaa atgttaagag   9060
aatttcaatg gttaagagct aattcatctg tcgtgtcagt aaactgtaaa ggtaaggata   9120
gtgagaagat tgaagagtgg agatcaagag cagccaagtt cgaggaaatg tgtgctttag   9180
tcatgggcat gtttaccaga ttgtctaatt gcgctaatag aactatcttg tatgatatgt   9240
attcatacgt ttgggacata aagtccatta tgtctatggt caaatcattt gtacaatggt   9300
tgggttgtag aagtcactct tctgcccagt tcttgattgg tgaccaagag ccttgggcct   9360
ttagaggcgg attggcaggc gaatttcaac gtttgttacc tattgacggt gctaatgatt   9420
tgttctttca gccaccacct ttaactccta cctctaaagt ctatactatt aggccatact   9480
ttcccaaaga cgaagccagt gtgtataaga tctgtagaga gatgtacgat gatggtgtag   9540
gtttgccatt tcaatcccaa ccagacttga taggtgacaa attggtagga ggtttgttgt   9600
ctttatcttt agactattgc ttcgtgttag aggatgagga tggtatttgc ggttatgcct   9660
taggaactgt agatgtaact ccctttcataa agaaatgcaa gatatcttgg atacctttca   9720
tgcaagagaa gtatactaaa ccaaatggtg ataaggaatt gagtgaagct gagaagatca   9780
tgttatcttt ccatgaagaa caagaagtat tgccagagac attcttggcc aatttccctt   9840
ctttgataaa gatggatata cataagaagg tgactgatcc ttcagtagcc aaatctatga   9900
tggcctgctt attgtcatcc ttaaaggcca atggatcaag aggtgctttc tgtgaggtga   9960
ggccagatga caagagaatc ttagagttct atagtaagtt aggttgtttc gagattgcta  10020
agatggaagg tttccctaag gacgtcgtga tcttgggaag gtcttttgtaa gaattctcat  10080 gtaattagtt atgtcacgct tacattcacg ccctcccccc acatccgctc taaccgaaaa  10140
ggaaggagtt agacaacctg aagtctaggt ccctatttat ttttttatag ttatgttagt  10200
attaagaacg ttatttatat ttcaaatttt tctttttttt ctgtacagac gcgtgtacgc  10260
atgtaacatt atactgaaaa ccttgcttga gaaggttttg ggacgctcga aggctttaat  10320
ttgccggatt agaagccgcc gagcgggtga cagccctccg aaggaagact ctcctccgtg  10380
cgtcctcgtc ttcaccggtc gcgttcctga aacgcagatg tgcctcgcgc cgcactgctc  10440
cgaacaataa agattctaca atactagctt ttatggttat gaagaggaaa aattggcagt  10500
aacctggccc cacaaacctt caaatgaacg aatcaaatta caaccatagg atgataatg   10560
```

```
cgattagttt tttagcctta tttctggggt aattaatcag cgaagcgatg attttttgatc    10620
tattaacaga tatataaatg caaaaactgc ataaccactt taactaatac tttcaacatt    10680
ttcggtttgt attacttctt attcaaatgt aataaaagta tcaacaaaaa attgttaata    10740
tacctctata ctttaacgtc aaggaggcgg ccgccatgtc taaaggtgaa gaattattca    10800
ctggtgttgt cccaattttg gttgaattag atggtgatgt taatggtcac aaattttctg    10860
tctccggtga aggtgaaggt gatgctactt acggtaaatt gaccttaaaa tttatttgta    10920
ctactggtaa attgccagtt ccatggccaa ccttagtcac tactttcggt tatggtgttc    10980
aatgttttgc tagatacccc gatcatatga acaacatga cttttttcaag tctgccatgc    11040
cagaaggtta tgttcaagaa agaactattt ttttcaaaga tgacggtaac tacaagacca    11100
gagctgaagt caagtttgaa ggtgatacct tagttaatag aatcgaatta aaaggtattg    11160
attttaaaga agatggtaac attttaggtc acaaattgga atacaactat aactctcaca    11220
atgtttacat catggctgac aaacaaaaga atggtatcaa agttaacttc aaaattagac    11280
acaacattga agatggttct gttcaattag ctgaccatta tcaacaaaat actccaattg    11340
gtgatggtcc agtcttgtta ccagacaacc attacttatc cactcaatct gccttatcca    11400
aagatccaaa cgaaaagaga gaccacatgg tcttgttaga atttgttact gctgctggta    11460
ttacccatgg tatggatgaa ttgtacaaat aatctagagg ccgcatcat gtaattagtt    11520
atgtcacgct tacattcacg ccctcccccc acatccgctc taaccgaaaa ggaaggagtt    11580
agacaacctg aagtctaggt ccctatttat ttttttatag ttatgttagt attaagaacg    11640
ttatttatat ttcaaatttt tcttttttttt ctgtacagac gcgtgtacgc atgtaacatt    11700
atactgaaaa ccttgcttga aaggttttg ggacgctcga aggctttaat ttgcggccct    11760
gcattaatga atcggccaac gcgcggggag aggcggtttg cgtattgggc gctcttccgc    11820
ttcctcgctc actgactcgc tgcgctcggt cgttcggctg cggcgagcgg tatcagctca    11880
ctcaaaggcg gtaatacggt tatccacaga atcaggggat aacgcaggaa agaacatgtg    11940
agcaaaaggc cagcaaaagc ccaggaaccg taaaaaggcc gcgttgctgg cgttttttcca    12000
taggctccgc cccctgacg agcatcacaa aaatcgacgc tcaagtcaga ggtggcgaaa    12060
cccgacagga ctataaagat accaggcgtt tccccctgga agctccctcg tgcgctctcc    12120
tgttccgacc ctgccgctta ccggatacct gtccgccttt ctcccttcgg gaagcgtggc    12180
gctttctcat agctcacgct gtaggtatct cagttcggtg taggtcgttc gctccaagct    12240
gggctgtgtg cacgaacccc ccgttcagcc cgaccgctgc gccttatccg gtaactatcg    12300
tcttgagtcc aacccggtaa gacacgactt atcgccactg gcagcagcca ctggtaacag    12360
gattagcaga gcgaggtatg taggcggtgc tacagagttc ttgaagtggt ggcctaacta    12420
cggctacact agaaggacag tatttggtat ctgcgctctg ctgaagccag ttaccttcgg    12480
aaaaagagtt ggtagctctt gatccggcaa acaaaccacc gctggtagcg gtggtttttt    12540
tgtttgcaag cagcagatta cgcgcagaaa aaaaggatct caagaagatc ctttgatctt    12600
ttctacgggg tctgacgctc agtggaacga aaactcacgt taagggattt tggtcatgag    12660
attatcaaaa aggatcttca cctagatcct ttttaaattaa aaatgaagtt ttaaatcaat    12720
ctaaagtata tatgagtaaa cttggtctga cagttaccaa tgcttaatca gtgaggcacc    12780
tatctcagcg atctgtctat ttcgttcatc catagttgcc tgactccccg tcgtgtagat    12840
aactacgata cgggagcgct taccatctgg ccccagtgct gcaatgatac cgcgagaccc    12900
acgctcaccg gctccagatt tatcagcaat aaaccagcca gccggaaggg ccgagcgcag    12960
```

```
aagtggtcct gcaactttat ccgcctccat ccagtctatt aattgttgcc gggaagctag    13020
agtaagtagt tcgccagtta atagtttgcg caacgttgtt ggcattgcta caggcatcgt    13080
ggtgtcactc tcgtcgtttg gtatggcttc attcagctcc ggttcccaac gatcaaggcg    13140
agttacatga tcccccatgt tgtgcaaaaa agcggttagc tccttcggtc ctccgatcgt    13200
tgtcagaagt aagttggccg cagtgttatc actcatggtt atggcagcac tgcataattc    13260
tcttactgtc atgccatccg taagatgctt ttctgtgact ggtgagtact caaccaagtc    13320
attctgagaa tagtgtatgc ggcgaccgag ttgctcttgc ccggcgtcaa tacgggataa    13380
tagtgtatca catagcagaa ctttaaaagt gctcatcatt ggaaaacgtt cttcggggcg    13440
aaaactctca aggatcttac cgctgttgag atccagttcg atgtaaccca ctcgtgcacc    13500
caactgatct tcagcatctt ttactttcac cagcgtttct gggtgagcaa aaacaggaag    13560
gcaaaatgcc gcaaaaagg gaataagggc gacacggaaa tgttgaatac tcatactctt    13620 ccttttcaa tgggtaataa ctgatataat taaattgaag ctctaatttg tgagtttagt    13680
atacatgcat ttacttataa tacagttttt tagttttgct ggccgcatct tctcaaatat    13740
gcttcccagc ctgcttttct gtaacgttca ccctctacct tagcatccct tccctttgca    13800
aatagtcctc ttccaacaat aataatgtca gatcctgtag agaccacatc atccacggtt    13860
ctatactgtt gacccaatgc gtctcccttg tcatctaaac ccacaccggg tgtcataatc    13920
aaccaatcgt aaccttcatc tcttccaccc atgtctcttt gagcaataaa gccgataaca    13980
aaatctttgt cgctcttcgc aatgtcaaca gtacccttag tatattctcc agtagatagg    14040
gagcccttgc atgacaattc tgctaacatc aaaaggcctc taggttcctt tgttacttct    14100
tctgccgcct gcttcaaacc gctaacaata cctgggccca ccacccgtg tgcattcgta    14160 atgtctgccc attctgctat tctgtataca cccgcagagt actgcaattt gactgtatta    14220
ccaatgtcag caaattttct gtcttcgaag agtaaaaaat tgtacttggc ggataatgcc    14280
tttagcggct taactgtgcc ctccatggaa aaatcagtca agatatccac atgtgttttt    14340
agtaaacaaa ttttgggacc taatgcttca actaactcca gtaattcctt ggtggtacga    14400
acatccaatg aagcacacaa gtttgtttgc ttttcgtgca tgatattaaa tagcttggca    14460
gcaacaggac taggatgagt agcagcacgt tccttatatg tagctttcga catgatttat    14520 cttcgttttcc tgcaggtttt tgttctgtgc agttgggtta agaatactgg gcaatttcat    14580
gtttcttcaa cactacatat gcgtatatat accaatctaa gtctgtgctc cttccttcgt    14640
tcttccttct gttcggagat taccgaatca aaaaatttc aaagaaaccg aaatcaaaaa    14700
aaagaataaa aaaaaatga tgaattgaat tgaaaagcta gcttatcgat gataagctgt    14760
caaagatgag aattaattcc acggactata gactatacta gatactccgt ctactgtacg    14820
atacacttcc gctcaggtcc ttgtcctttta acgaggcctt accactcttt tgttactcta    14880
ttgatccagc tcagcaaagg cagtgtgatc taagattcta tcttcgcgat gtagtaaaac    14940
tagctagacc gagaaagaga ctagaaatgc aaaaggcact tctacaatgg ctgccatcat    15000
tattatccga tgtgacgctg cagcttctca atgatattcg aatacgcttt gaggagatac    15060
agcctaatat ccgacaaact gttttacaga tttcgatcg tacttgttac ccatcattga    15120
attttgaaca tccgaacctg ggagttttcc ctgaaacaga tagtatattt gaacctgtat    15180
aataatatat agtctagcgc tttacggaag acaatgtatg tatttcggtt cctggagaaa    15240
ctattgcatc tattgcatag gtaatcttgc acgtcgcatc cccggttcat tttctgcgtt    15300
```

```
tccatcttgc acttcaatag catatctttg ttaacgaagc atctgtgctt cattttgtag    15360
aacaaaaatg caacgcgaga gcgctaattt ttcaaacaaa gaatctgagc tgcattttta    15420
cagaacagaa atgcaacgcg aaagcgctat tttaccaacg aagaatctgt gcttcatttt    15480
tgtaaaacaa aaatgcaacg cgacgagagc gctaattttt caaacaaaga atctgagctg    15540 cattttaca gaacagaaat gcaacgcgag agcgctattt taccaacaaa gaatctatac     15600
ttcttttttg ttctacaaaa atgcatcccg agagcgctat ttttctaaca aagcatctta    15660
gattactttt tttctccttt gtgcgctcta taatgcagtc tcttgataac ttttttgcact   15720 gtaggtccgt taaggttaga agaaggctac tttggtgtct attttctctt ccataaaaaa    15780
agcctgactc cacttcccgc gtttactgat tactagcgaa gctgcgggtg catttttttca   15840 agataaaggc atccccgatt atattctata ccgatgtgga ttgcgcatac tttgtgaaca    15900
gaaagtgata gcgttgatga ttcttcattg gtcagaaaat tatgaacggt ttcttctatt    15960
ttgtctctat atactacgta taggaaatgt ttacattttc gtattgtttt cgattcactc    16020
tatgaatagt tcttactaca attttttttgt ctaaagagta atactagaga taaacataaa   16080
aaatgtagag gtcgagttta gatgcaagtt caaggagcga aaggtggatg ggtaggttat    16140
atagggatat agcacagaga tatatagcaa agagatactt ttgagcaatg tttgtggaag    16200
cggtattcgc aatgggaagc tccacccccgg ttgataatca gaaaagcccc aaaaacagga    16260
agattgtata agcaaatatt taaattgtaa acgttaatat tttgttaaaa ttcgcgttaa    16320 attttttgtta aatcagctca ttttttttaacg aatagcccga aatcggcaaa atcccttata   16380
aatcaaaaga atagaccgag atagggttga gtgttgttcc agtttccaac aagagtccac    16440
tattaaagaa cgtggactcc aacgtcaaag ggcgaaaaag ggtctatcag ggcgatggcc    16500
cactacgtga accatcaccc taatcaagtt ttttggggtc gaggtgccgt aaagcagtaa    16560
atcggaaggg taaacggatg cccccattta gagcttgacg gggaaagccg gcgaacgtgg    16620
cgagaaagga agggaagaaa gcgaaaggag cgggggctag ggcggtggga agtgtagggg    16680
tcacgctggg cgtaaccacc acacccgccg cgcttaatgg ggcgctacag ggcgcgtggg    16740
gatgatccac tagt                                                      16754
```

<210> SEQ ID NO 6
<211> LENGTH: 1155
<212> TYPE: DNA
<213> ORGANISM: Saccharomyces cerevisiae

<400> SEQUENCE: 6

```
atgtccaaga gcaaaacttt cttatttacc tctgaatccg tcggtgaagg tcacccagac      60
aagatttgtg accaagtttc tgatgctatt ttggacgctt gtttagaaca agatccattc    120
tccaaggttg cctgtgaaac agctgccaaa actggtatga ttatggtttt cggtgaaatt    180
accaccaaag ctagacttga ctaccaacaa atagtaagag ataccatcaa gaagattggt    240
tatgacgatt ctgccaaggg tttcgactac aagacatgta atgttttagt agctatcgaa    300
caacaatctc cagatatcgc tcaaggtctg cactatgaaa agagcttaga agacttaggt    360
gctggtgacc aagtataat gtttggttac gctacagacg aaactccaga agggttacca    420
ttgaccattc ttttggctca caaattgaac atggctatgg cagatgctag aagagatggt    480
tctctcccat ggttgagacc agacacaaag actcaagtca ctgtcgaata cgaagacgac    540
aatggtagat gggttccaaa gaggatagat accgttgtta tttctgctca acatgctgat    600
gaaatttcca ccgctgactt gagaactcaa cttcaaaaag atattgttga aaaggtcata    660
```

```
ccaaaggata tgttagacga aaataccaaa tatttcatcc aaccatccgg tagattcgtc    720
atcggtggtc ctcaaggtga cgctggtttg accggtagaa agattattgt cgacgcttac    780
ggtggtgcct catccgtcgg tggtggtgcc ttctccggta aggactattc caaggtcgat    840
cgttccgctg cttacgctgc tagatgggtt gccaagtctc tagttgccgc tggtttgtgt    900
aagagagtcc aagtccaatt ttcatatgct attggtattg ctgaaccatt gtctttacat    960
gtggacacct atggtacagc tacaaaatca gatgacgaaa tcattgaaat tattaagaag   1020
aacttcgact tgagaccagg tgtgttagta aaggaattag atttggctag accaatttac   1080
ttaccaaccg cttcttatgg tcacttcact aatcaagagt actcatggga aaaaccaaag   1140
aaattggaat tttaa                                                     1155
```

<210> SEQ ID NO 7
<211> LENGTH: 1503
<212> TYPE: DNA
<213> ORGANISM: Saccharomyces cerevisiae

<400> SEQUENCE: 7

```
atgtctagat tagaaagatt gacctcatta aacgttgttg ctggttctga cttgagaaga     60
acctccatca ttggtaccat cggtccaaag accaacaacc cagaaacctt ggttgctttg    120
agaaaggctg gtttgaacat tgtccgtatg aacttctctc acggttctta cgaataccac    180
aagtctgtca ttgacaacgc cagaaagtcc gaagaattgt acccaggtag accattggcc    240
attgctttgg acaccaaggg tccagaaatc agaactggta ccaccaccaa cgatgttgac    300
tacccaatcc caccaaacca cgaaatgatc ttcaccaccg atgacaagta cgctaaggct    360
tgtgacgaca gatcatgta cgttgactac aagaacatca ccaaggtcat ctccgctggt    420
agaatcatct acgttgatga tggtgttttg tctttccaag ttttggaagt cgttgacgac    480
aagactttga aggtcaaggc tttgaacgcc ggtaagatct gttccacaa gggtgtcaac    540 ttaccaggta ccgatgtcga tttgccagct ttgtctgaaa aggacaagga agatttgaga    600
ttcggtgtca agaacggtgt ccacatggtc ttcgcttctt tcatcagaac cgccaacgat    660
gttttgacca tcagagaagt cttgggtgaa caaggtaagg acgtcaagat cattgtcaag    720
attgaaaacc aacaaggtgt taacaacttc gacgaaatct gaaggtcac tgacggtgtt    780 atggttgcca gaggtgactt gggtattgaa atcccagccc agaagtcttg gctgtccaa    840 aagaaattga ttgctaagtc taacttggct ggtaagccag ttatctgtgc tacccaaatg   900
ttggaatcca tgacttacaa cccaagacca accagagctg aagtttccga tgtcggtaac    960
gctatcttgg atggtgctga ctgtgttatg ttgtctggtg aaaccgccaa gggtaactac   1020
ccaatcaacg ccgttaccac tatggctgaa accgctgtca ttgctgaaca agctatcgct   1080
tacttgccaa actacgatga catgagaaac tgtactccaa agccaacctc caccaccgaa   1140
accgtcgctg cctccgctgt cgctgctgtt tcgaacaaa aggccaaggc tatcattgtc   1200
ttgtccactt ccggtaccac cccaagattg gtttccaagt acagaccaaa ctgtccaatc   1260
atcttggtta ccagatgccc aagagctgct agattctctc acttgtacag aggtgtcttc   1320
ccattcgttt tcgaaaagga acctgtctct gactggactg atgatgttga agcccgtatc   1380
aacttcggta ttgaaaaggc taaggaattc ggtatcttga agaagggtga cacttacgtt   1440
tccatccaag gtttcaaggc cggtgctggt cactccaaca ctttgcaagt ctctaccgtt   1500
taa                                                                 1503
```

<210> SEQ ID NO 8
<211> LENGTH: 765
<212> TYPE: DNA
<213> ORGANISM: Saccharomyces cerevisiae

<400> SEQUENCE: 8

| | | | | | |
|---|---|---|---|---|---|
| atgagtatcg | ctgaattcgc | ttacaaggaa | aaaccagaaa | ctttggtttt | attcgatgtt | 60 |
| gatggtacct | tgacaccagc | cagattaact | gtttctgaag | aagttagaaa | actttggcc | 120 |
| aagttgagaa | acaagtgctg | cattggtttt | gtcggtggtt | ctgacttaag | caagcaatta | 180 |
| gaacagttag | gcccaaacgt | tttagatgaa | tttgactatt | cttttctctga | aaatggtttg | 240 |
| accgcctaca | gattaggtaa | ggaattagct | tctcaatcct | tcatcaactg | gctcggtgag | 300 |
| gaaaaataca | ataaattggc | cgtcttcatt | ttgagatatc | tatctgaaat | tgacttgcca | 360 |
| aagagaagag | gtactttctt | ggaatttaga | atggtatga | tcaacgtttc | cccaattggt | 420 |
| agaaatgctt | ctactgagga | aagaaacgaa | ttcgaaagat | acgataagga | acaccaaatc | 480 |
| agagccaagt | tcgttgaagc | tttgaaaaag | gaattcccag | actacggttt | gactttctcc | 540 |
| attggtggcc | aaatctcttt | cgacgttttc | cccgctggtt | gggataagac | ctactgtttg | 600 |
| caacacgttg | aaaaagatgg | tttcaaggaa | attcatttct | tggtgacaa | gactatggtc | 660 |
| ggtggtaacg | attacgaaat | ttttgtcgat | gaaagaacca | tcggacattc | agtacaatcc | 720 |
| cctgatgaca | ccgtcaaaat | tttgactgaa | ctattcaact | tatag | | 765 |

<210> SEQ ID NO 9
<211> LENGTH: 1005
<212> TYPE: DNA
<213> ORGANISM: Saccharomyces cerevisiae

<400> SEQUENCE: 9

| | | | | | |
|---|---|---|---|---|---|
| atgttgtcaa | gagtagctaa | acgtgcgttt | ccctctacag | ttgccaaccc | ttataaagtg | 60 |
| actgttttgg | gtgcaggcgg | tggtattgga | caaccattgt | ctttgcttct | aaagcttaac | 120 |
| cataaagtca | cggacttaag | actgtacgac | ctaaagggcg | caaaggtgt | tgccaccgat | 180 |
| ttgtctcata | ttccaacaaa | ctccgtggtc | aaggggttta | ctccagaaga | gccagacgga | 240 |
| ttgaacaacg | ctttaaagga | cacagacatg | gttttaattc | ctgctggtgt | gcccagaaag | 300 |
| cctggtatga | cacgtgatga | cttgttcgcc | atcaacgcaa | gcatcgttcg | cgatttggca | 360 |
| gcagcaaccg | ccgaatccgc | tcccaatgct | gccattctgg | tcatttccaa | cccagtcaat | 420 |
| tctaccgttc | caattgtcgc | ccaagtcttg | aaaaacaagg | gtgtttacaa | cccaaagaaa | 480 |
| ttgttcggtg | tgactacctt | ggactctatt | agagccgcca | gattcatctc | agaagtcgag | 540 |
| aacaccgatc | caactcagga | aagggttaac | gtcatcggtg | acattctgg | tattaccatc | 600 |
| atcccattga | tttcgcaaac | aaaccataag | ttgatgtctg | atgacaagag | acacgaattg | 660 |
| attcacagaa | tacagtttgg | tggtgacgaa | gtcgtcaaag | caagaatgg | tgctggctct | 720 |
| gctacgttgt | caatggccca | tgctggtgct | aaattcgcta | acgctgtttt | gtccggtttc | 780 |
| aaaggcgaaa | gagacgtcat | cgagccttcc | ttcgtggact | ctcccttgtt | caaatccgaa | 840 |
| ggcatcgaat | tctttgcatc | tccggtcact | ttgggcccag | atggtattga | aaagatccat | 900 |
| ccaataggtg | agttatcttc | agaagaagaa | gaaatgctac | aaaaatgtaa | agaaaccttg | 960 |
| aagaagaata | tcgaaaaggg | tgtcaacttt | gttgctagta | aatag | | 1005 |

<210> SEQ ID NO 10
<211> LENGTH: 1458

```
<212> TYPE: DNA
<213> ORGANISM: Saccharomyces cerevisiae

<400> SEQUENCE: 10
atggttcatt taggtccaaa gaaaccacag gctagaaagg gttccatggc tgatgtgccc     60
aaggaattga tggatgaaat tcatcagttg aagatatgt ttacagttga cagcgagacc    120
ttgagaaagg ttgttaagca ctttatcgac gaattgaata aaggtttgac aaagaaggga    180
ggtaacattc caatgattcc cggttgggtc atggaattcc caacaggtaa agaatctggt    240
aactatttgg ccattgattt gggtggtact aacttaagag tcgtgttggt caagttgagc    300
ggtaaccata cctttgacac cactcaatcc aagtataaac taccacatga catgagaacc    360
actaagcacc aagaggagtt atggtccttt attgccgact cttttgaagga ctttatggtc    420 gagcaagaat tgctaaacac caaggacacc ttaccattag gtttcacctt ctcgtaccca    480
gcttcccaaa acaagattaa cgaaggtatt ttgcaaagat ggaccaaggg tttcgatatt    540
ccaaatgtcg aaggccacga tgtcgtccca ttgctacaaa acgaaatttc caagagagag    600
ttgcctattg aaattgtagc attgattaat gatactgttg gtactttaat tgcctcatac    660
tacactgacc cagagactaa gatgggtgtg atttttcggta ctggtgtcaa cggtgctttc    720
tatgatgttg tttccgatat cgaaaagttg gagggcaaat tagcagacga tattccaagt    780
aactctccaa tggctatcaa ttgtgaatat ggttccttcg ataatgaaca tttggtcttg    840
ccaagaacca agtacgatgt tgctgtcgac gaacaatctc caagacctgg tcaacaagct    900
tttgaaaaga tgacctccgg ttactacttg ggtgaattgt tgcgtctagt gttacttgaa    960
ttaaacgaga agggcttgat gttgaaggat caagatctaa gcaagttgaa acaaccatac   1020
atcatggata cctcctaccc agcaagaatc gaggatgatc catttgaaaa cttggaagat   1080
actgatgaca tcttccaaaa ggactttggt gtcaagacca ctctgccaga acgtaagttg   1140
attagaagac tttgtgaatt gatcggtacc agagctgcta gattagctgt ttgtggtatt   1200
gccgctattt gccaaaagag aggttacaag actggtcaca ttgccgctga cggttctgtc   1260
tataacaaat acccaggttt caaggaagcc gccgctaagg gtttgagaga tatctatgga   1320
tggactggtg acgcaagcaa agatccaatt acgattgttc cagctgagga tggttcaggt   1380
gcaggtgctg ctgttattgc tgcattgtcc gaaaaaagaa ttgccgaagg taagtctctt   1440
ggtatcattg gcgcttaa                                                1458

<210> SEQ ID NO 11
<211> LENGTH: 468
<212> TYPE: DNA
<213> ORGANISM: Hordeum vulgare

<400> SEQUENCE: 11
atgctcgtgt accaggacaa gctttccggc gatgaactcc tgtcggattc cttcccgtac     60
agggagctgg agaacggtgt gctctgggaa gtcgatggcc attgggtcgt tcaaggagca    120
gttgatgtgg acattggtgc caacccctct gctgagggtg gtggtgagga tgagggtgtc    180
gatgaccagg ccgtgaaggt ggttgacatt gttgacacct ccgtcttca ggagcaacct    240 gcttttgaca agaagcagtt tattgcttac atcaagcgct acatcaagaa cctcactgcc    300
aagcttgaag gtgaggagct agatgctttc aagaagaacg ttgagtctgc cacgaagtat    360
cttcttagca agctcaagga ccttcagttc tttgtgggcg agagcatgca tgatgatggc    420
agcgtggtgt ttaagcttga ttgcctacta cagggaggga gctgctga                468
```

<210> SEQ ID NO 12
<211> LENGTH: 6438
<212> TYPE: DNA
<213> ORGANISM: Saccharomyces cerevisiae

<400> SEQUENCE: 12

| | |
|---|---|
| atgccagtgt tgaaatcaga caatttcgat ccattggaag aagcttacga aggtgggaca | 60 |
| attcaaaact ataacgatga acaccatctt cataaatctt gggcaaatgt gattccggac | 120 |
| aaacgaggac tttacgaccc tgattatgaa catgacgctt gtggtgtcgg tttcgtagca | 180 |
| aataagcatg gtgaacagtc tcacaagatt gttactgacg ctagatatct tttagtgaat | 240 |
| atgacacatc gtggtgccgt ctcatctgat gggaacggtg acggtgccgg tattctgcta | 300 |
| ggtattcctc acgaatttat gaaaagagaa ttcaagttag atcttgatct agacatacct | 360 |
| gagatgggca atacgccgt aggtaacgtc ttcttcaaga agaacgaaaa aaataacaag | 420 |
| aaaaatttaa ttaagtgtca gaagattttc gaggatttag ctgcatcctt caacttatcc | 480 |
| gtattaggtt ggagaaacgt ccccgtagat tctactattt taggagacgt tgcattatct | 540 |
| cgtgaaccta ctattctaca gccattattg gttccattgt atgatgaaaa acaaccggag | 600 |
| tttaatgaaa ctaaatttag aactcaattg tatcttttaa ggaaggaggc ctctcttcaa | 660 |
| ataggactgg aaaactggtt ctatgtttgt tccctaaaca ataccaccat tgtttacaag | 720 |
| ggtcaattga cgccagctca agtgtataac tactatcccg acttgactaa tgcgcatttc | 780 |
| aaatcccaca tggcgttggt ccattcaaga ttttccacta atactttccc ctcttgggat | 840 |
| agagctcaac ctttacgttg gctagctcat aatggtgaaa ttaacacctt aagaggtaac | 900 |
| aagaattgga tgcgctccag agaaggtgtg atgaattcag caactttcaa agatgagtta | 960 |
| gacaaactat acccaattat cgaagaaggt ggttctgatt cagctgcatt ggataacgtt | 1020 |
| ttagaactat tgactattaa tggcacatta tctctacctg aagctgttat gatgatggtt | 1080 |
| cctgaagcgt atcataagga tatggattct gacctaaaag catggtacga ctgggctgca | 1140 |
| tgtctgatgg aaccttggga tggtccagct tgttaactt tcactgatgg acgttactgt | 1200 |
| ggtgctatat ggatagaaa tggtttaaga ccttgtcgtt attacatcac tagtgatgac | 1260 |
| agagttatct gtgcttcaga ggtaggtgtc attcctatcg aaaattcatt ggttgttcaa | 1320 |
| aaaggtaaac tgaagccagg tgatttattc ctagtggata tcaattggg tgaaatggtc | 1380 |
| gatactaaaa agttaaaatc tcaaatctca aaaagacaag attttaagtc ttggttatcc | 1440 |
| aaagtcatca gttagacga cttgttatca aaaccgcta atttggttcc taaagaattt | 1500 |
| atatcacagg attcattgtc tttgaaagtt caaagtgacc cacgtctatt ggccaatggt | 1560 |
| tataccttcg aacaagtcac atttctgtta actccaatgg ctttaacagg taaagaagct | 1620 |
| ttaggttcga tgggtaacga tgcgccactg gcttgtttaa atgaaaatcc tgtcttactt | 1680 |
| tatgattatt tcagacaatt gtttgctcaa gtgaccaatc ctccaattga cccaattcgt | 1740 |
| gaagcaaatg ttatgtcgtt agaatgttat gtcggacctc aaggcaacct tttggaaatg | 1800 |
| cattcatctc aatgtgatcg tttattattg aaatctccta ttttgcattg gaatgagttc | 1860 |
| caagctttga aaacattga agctgcttac ccatcatggt ctgtagcaga aattgatatc | 1920 |
| acattcgaca gagtgaggg tctattgggc tataccgaca caattgataa aatcactaag | 1980 |
| ttagcgagcg aagcaattga tgatggtaaa aagatcttaa taattactga caggaaaatg | 2040 |
| ggtgccaacc gtgtttccat ctcctctttg attgcaattt catgtattca tcatcaccta | 2100 |
| atcagaaaca agcagcgttc ccaagttgct ttgattttgg aaacaggtga agccagagaa | 2160 |

```
attcaccatt tctgtgtcct actaggttat ggttgtgatg gtgtttatcc atacttagcc   2220
atggaaactt tggtcagaat gaatagagaa ggtctacttc gtaatgtcaa caatgacaat   2280
gatacacttg aggaagggca aatactagaa aattacaagc acgctattga tgcaggtatc   2340
ttgaaggtta tgtctaaaat gggtatctcc actctagcat cctacaaagg tgctcaaatt   2400
tttgaagccc taggtttaga taactctatt gttgatttgt gtttcacagg tacttcttcc   2460
agaattagag gtgtaacttt cgagtatttg gctcaagatg cctttctttt acatgagcgt   2520
ggttatccat ccagacaaac cattagtaaa tctgttaact taccagaaag tggtgaatac   2580
cactttaggg atggtggtta caaacacgtc aacgaaccaa ccgcaattgc ttcgttacaa   2640
gatactgtca gaaacaaaaa tgatgtctct tggcaattat atgtaaagaa ggaaatggaa   2700
gcaattagag actgtacact aagaggactg ttagaattag attttgaaaa ttctgtcagt   2760
atccctctag aacaagttga accatggact gaaattgcca gaagatttgc gtcaggtgca   2820
atgtcttatg gttctatttc tatggaagct cactctacat tggctattgc catgaatcgt   2880
ttaggggcca aatccaattg tggtgaaggt ggtgaagacg cagaacgttc tgctgttcaa   2940
gaaaacggtg atactatgag atctgctatc aaacaagttg cttccgctag attcggtgta   3000
acttcatact acttgtcaga tgctgatgaa atccaaatta gattgctca gggtgctaag   3060 ccgggtgaag tggtgaact accagcccac aaagtgtcta aggatatcgc aaaaaccagg   3120
cactccaccc ctaatgttgg gttaatctct cctcctcctc atcacgatat ttattccatt   3180
gaagatttga acaactgat ttatgatttg aaatgtgcta atccaagagc gggaatttct   3240
gtaaagttgg tttccgaagt tggtgttggt attgttgcct ctggtgtagc taaggctaaa   3300
gccgatcata tcttagtttc tggtcatgat ggtggtacag gtgctgcaag atggacgagt   3360
gtcaaatatg cgggttttgcc atgggaatta ggtctagctg aaaactcacca gactttagtc   3420 ttgaatgatt taagacgtaa tgttgttgtc caaaccgatg gtcaattgag aactgggttt   3480
gatattgctg ttgcagtttt attaggggca gaatctttta ccttggcaac agttccatta   3540
attgctatgg gttgtgttat gttaagaaga tgtcacttga actcttgtgc tgttggtatt   3600
gccacacaag atccatattt gagaagtaag tttaagggtc agcccgaaca tgttatcaac   3660
ttcttctatt acttgatcca agatttaaga caaatcatgg ccaagttagg attccgtacc   3720
attgacgaaa tggtgggtca ttctgaaaaa ttaaagaaaa gggacgacgt aaatgccaaa   3780
gccataaaat tcgatttatc tcctattttg accccagcac atgttattcg tccaggtgtt   3840
ccaaccaagt tcactaagaa acaagaccac aaactccaca cccgtctaga taataagtta   3900
atcgatgagg ctgaagttac tttggatcgt ggcttaccag tgaatattga cgcctctata   3960
atcaatactg atcgtgcact cggttctact ttatcttaca gagtctcgaa gaaatttggt   4020
gaagatggtt tgccaaagga caccgttgtc gttaacatag aaggttcagc gggtcaatct   4080
tttgtgcttt cctagcttc tggtatcact tttatcttga atggtgatgc taatgattat   4140
gttggtaaag gtttatccgg tggtattatt gtcattaaac caccaaagga ttctaaattc   4200
aagagtgatg aaaatgtaat tgttggtaac acttgtttct atggtgctac ttctggtact   4260
gcattcattt caggtagtgc cggtgagcgt ttcggtgtca gaaactctgg tgccaccatc   4320
gttgttgaga gaattaaggg taacaatgcc tttgagtata tgactggtgg tcgtgccatt   4380
gtcttatcac aaatgggaatc cctaaacgcc ttctctggtg ctactggtgg tattgcatac   4440
tgtttaactt ccgattacga cgattttgtt ggaaagatta acaaagatac tgttgagtta   4500
```

```
gaatcattat gtgacccggt cgagattgcg tttgttaaga atttgatcca ggagcattgg    4560
aactacacac aatctgatct agcagccagg attctcggta atttcaacca ttatttgaaa    4620
gatttcgtta aagtcattcc aactgattat aagaaagttt tgttgaagga gaaagcagaa    4680
gctgccaagg caaaggctaa ggcaacttca gaatacttaa agaagtttag atcgaaccaa    4740
gaagttgatg acgaagtcaa tactctattg attgctaatc aaaaagctaa agagcaagaa    4800
aaaaagaaga gtattactat ttcaaataag gccactttga aggagcctaa ggttgttgat    4860
ttagaagatg cagttccaga ttccaaacag ctagagaaga atagcgaaag gattgaaaaa    4920
acacgtggtt ttatgatcca caacgtcgt catgagacac acagagatcc aagaaccaga    4980
gttaatgact ggaaagaatt tactaaccct attaccaaga aggatgccaa atatcaaact    5040
gcgagatgta tggattgtgg tacaccattc tgtttatctg ataccggttg tccctatct    5100 aacattatcc ccaagtttaa tgaattgtta ttcaagaacc aatggaagtt ggcactggac    5160
aaattgctag agacaaacaa tttcccagaa ttcactggaa gagtatgtcc agcaccctgt    5220
gagggagctt gtacactagg tattattgaa gacccagtcg gcataaaatc ggttgaaaga    5280
attatcattg acaatgcttt caaggaagga tggattaagc cttgtccacc aagtacacgc    5340
actggcttta cagtgggtgt cattggttct ggtccagcag gtttagcgtg tgctgatatg    5400
ttgaaccgtg ccggacatac ggtcactgtt tatgaaagat ccgaccgttg tggtgggtta    5460
ttgatgtatg gtattccaaa catgaagttg ataaggcta tagtgcaacg tcgtattgat    5520
ctattgagtg ccgaaggtat tgactttgtt accaacaccg aaattggtaa aaccataagc    5580
atggatgagc taaagaacaa gcacaatgca gtagtgtatg ctatcggttc taccattcca    5640
cgtgacttac ctattaaggg tcgtgaattg aagaatattg attttgccat gcagttgttg    5700
gaatctaaca caaaagcttt attgaacaaa gatctggaaa tcattcgtga aaagatccaa    5760
ggtaagaaag taattgttgt cggtggtggt gacacaggta acgattgttt aggtacatct    5820 gtaagcacg tgtcagcatc agttttgaat ttcgaattgt tgcctgagcc accagtggaa    5880
cgtgccaaag acaatccatg gcctcaatgg ccgcgtgtca tgagagtgga ctacggtcat    5940
gctgaagtga aagagcatta tggtagagac cctcgtgaat actgcatctt gtccaaggaa    6000
tttatcggta acgatgaggg tgaagtcact gccatcagaa ctgtgcgcgt agaatggaag    6060
aagtcacaaa gtggcgtatg gcaaatggta gaaattccca acagtgaaga gatctttgaa    6120
gccgatatca ttttgttgtc tatgggtttc gtgggtcctg aattgatcaa tggcaacgat    6180
aacgaagtta agaagacaag acgtggtacg attgccacac tcgacgactc ctcatactct    6240
attgatggag gaaagacttt tgcatgtggt gactgtagaa gagggcaatc tttgattgtc    6300
tgggccatcc aagaaggtag aaaatgtgct gcctctgtcg ataagttcct aatggacggc    6360
actacgtatc taccaagtaa tggtggtatc gttcaacgtg attacaaact attgaaagaa    6420
ttagctagtc aagtctaa                                                  6438

<210> SEQ ID NO 13
<211> LENGTH: 2409
<212> TYPE: DNA
<213> ORGANISM: Saccharomyces cerevisiae

<400> SEQUENCE: 13
atgctcaaca ttctcgtttt aggaaacggt gcaagagaac acgttcttgt caccaagctg      60
gctcagtcac ccaccgtggg taagatctat gtcgctccag gtaatggagg gaccgcaacc     120
atggatcctt cgcgtgtgat aaactgggat attacgccag atgtcgccaa ttttgctcgt     180
```

```
ttgcagtcga tggctgtgga acataagatc aacttggtcg ttcctggtcc agaattacct    240
ctagtcaacg gcatcacctc cgtgttccat agcgttggta ttcccgtttt tggaccttcc    300
gtcaaagccg ctcagttgga agcttccaag gctttctcca agagatttat gtcaaaacac    360
aatattccaa ccgcgtctta tgatgtcttc actaatccag aagaagccat ttcattcttg    420
caagctcata ctgacaaagc ttttgtcatc aaggccgacg ggatcgctgc tgggaaaggt    480
gttattatcc catctagcat cgacgagtcc gtccaagcta tcaaggacat aatggtcacc    540
aagcaattcg gtgaagaagc gggcaagcag gttgtgatag aacaattctt ggaaggtgat    600
gaaatctctc tactcaccat tgttgacggg tactctcact tcaatctccc cgtcgcacaa    660
gatcacaaga ggatctttga tggcgacaag ggcttgaaca ccggtgggat gggtgcctat    720
gcccccgctc ctgtggccac accatctttg ttgaagacca tagattcaca gattgtgaag    780
cctacgattg atgggatgag acgtgatggt atgccctttg ttggtgtgct gttcaccggg    840
atgattttgg tgaaggattc taagacaaat caacttgttc ccgaagtgtt agaatataat    900
gtcagattcg gtgacccaga gacacaggct gttttgagtt tacttgatga tcaaaccgat    960
ttggcgcaag tgttttttggc tgctgctgaa catcgtttgg attccgtaaa cataggaatc   1020
gatgacacaa gatctgccgt tactgtcgta gtggctgcag gtggttatcc tgaatcatac   1080
gccaaaggtg acaaaattac cttggatacc gataaattac ctccacatac acaaatcttc   1140
caagcaggta ccaaatacga ttccgccacc gattctttat tgaccaatgg tggtagagtt   1200
ctttctgtga cctccactgc tcaggacttg agaacagcag tagatacagt atatgaagcc   1260
gtcaaatgcg tccatttcca aaattcttac tacagaaagg acatcgcata ccgtgcgttc   1320
caaaactcag aatcatcaaa agttgccatc acatacgcag actcaggtgt ctctgttgat   1380
aatggtaaca atctcgtaca aactatcaaa gaaatggtca gatccacaag aaggccaggt   1440
gcagactctg atattggtgg ttttggtggt ttattcgatt tggctcaagc aggtttccgt   1500
caaaacgaag ataccttact agtaggtgct acagatggtc tcggtactaa attaatcatt   1560
gcccaagaga ccgggattca taatactgtc ggtattgacc tggtggccat gaatgttaac   1620
gatttggtgg tacaaggtgc tgagcctcta ttcttttttgg actactttgc cactggtgct   1680
cttgacattc aagttgcctc tgattttgtg tccggtgttg ctaatggttg tattcaaagt   1740
ggttgtgctc ttgtgggtgg tgaaacttcg gaaatgcccg gtatgtatcc acccggccac   1800
tacgatacta atggtaccgc tgttggtgct gtattaagac aagatatctt gcccaagata   1860
aatgaaatgg ccgcaggaga tgttcttctg ggtctcgcct ctagcggtgt tcattctaat   1920
ggtttctctt tggttagaaa aattattcaa catgtagcat taccatggga cgctccatgt   1980
ccatgggatg aatctaagac gttaggtgaa ggtattcttg aaccaacaaa aatttacgtc   2040
aagcaattat tgccatcaat tagacaaaga ctactactag gtttagctca tataacaggt   2100
ggtggtttag tagagaatat cccaagagct attccagacc acctacaggc ccgcgttgat   2160
atgtcaacct gggaagtacc ccgtgtcttc aaatggtttg gtcaagcagg taatgttcca   2220
cacgatgaca ttttaagaac cttcaacatg ggtgttggta tggttttgat tgtcaagaga   2280
gaaaacgtca aggctgtttg tgattcattg actgaagaag gtgaaattat ttgggagctt   2340
ggttctttgc aagaaagacc aaaggatgct cccggttgtg tgattgaaaa cggaactaag   2400
ctttactaa                                                           2409
```

<210> SEQ ID NO 14

<211> LENGTH: 13047
<212> TYPE: DNA
<213> ORGANISM: Mus musculus

<400> SEQUENCE: 14

| | |
|---|---|
| cggttcacta gaggagggaa gaagtctaca aggacccatc aatttcctgc ctgcctgcag | 60 |
| caaggacaga cggcatgagc actgcgggaa aagtaaggaa aagatctcac tgttggaaat | 120 |
| gtattctcag taatacgtgg agagatgcag agtcctacct tagaaataac aggctctgat | 180 |
| ctgctgtagt gcagaaggtg tcctgggtga gcacagcttg acctgctact aaatatcttt | 240 |
| aacaagaggg catagaacct gggtttgtga aagtctttat tccctcactt cctctgcagg | 300 |
| acagggaact tattccaagt cagtggtggc tgctttgcaa acagaaagtt tttaaaaagg | 360 |
| tcttttactg aaagtctgta tttatcaata atgtgttatt ctttctggtc atattttgtt | 420 |
| atgaacatag aaaagttaaa tctggcaaga gtttcatagg aggaatttga ttcagggagc | 480 |
| ttagtactgt tcctgtagcc attaggtaac gtttctggtg agagatggac tgatttgaaa | 540 |
| gcattagagt cattcacagt aagattatgt taccatgtaa attgtgattt gaagggccca | 600 |
| ttattgcaca actcacggat ttctacaaaa atcctataaa cagtctctct cctgtttaaa | 660 |
| aaaaaatcat ccagatttta tggaaaatta atttgaataa aaatggaact gattgttagt | 720 |
| attaagaata cacacatatg gtactgagtt ttccacaaaa atcacactca tttgttcagc | 780 |
| gtttacatgg taccgcaatg atggtgaaca gccaatcagt ataattaatt atctatcgct | 840 |
| taattatata agcctatgtt tctgttggca cagaggctat tttaggagtg ggtcaagagt | 900 |
| ccaacaactg acagtgagaa ctgggtgtcc gacgtcgcag aggtttctgc acgcactgtg | 960 |
| tgacaaaatt cttcattttt atttcaattc acttcacact ggttatgttt agggtggcat | 1020 |
| attacatttc aaagaaaaag cagttaggaa aaaagttaa actgaaattt ctagctgaaa | 1080 |
| aagtaaaaaa aaaaaaaaaa gtaagttcat acagcaagaa tgtaaaccca ccacatccat | 1140 |
| caaacagcaa tcgagggagg ggacagagaa agcagtctga ggtacagagg tcaataacag | 1200 |
| tgctgtgatg atagtcagtc tatgcttata cttcctagag cagcaaaatc ataatgtagc | 1260 |
| caggtatggt agaatatctc tgaaatcttg ggaataggaa ggcccctagc ttaaggccag | 1320 |
| cctgggctgc ttattagaat ttttgtctca gaagtcccac ccctgggggt taactctgtg | 1380 |
| atagaggact tgcctagagt gcacaaagtt ctgggtactg tcctcggtgc ctgaaaaata | 1440 |
| aataattata atttagaatt aaatatatgc ccaacaattg cacagaaaca acctttttgg | 1500 |
| ggacagtaca ggtgacatcc agaaagcaaa ccaacaagca agcagtcaaa acatggggca | 1560 |
| gcgtagcttg acagcacccg tgtcacttta acttggtata ctacacttac ttgtgttttc | 1620 |
| ccgaccttgg gctaagctgt cacacatttt ttttaaaggct ttttaactct ttgtaaatca | 1680 |
| gaactgtctg tctctatgta acacttactg ggtgacatag acggggacag atgatatata | 1740 |
| tatatatata tatatatata tatatatatg tgtgtgtgtg tgtgtatata tatatatata | 1800 |
| tatatatata tatatatata tacatacata catatacata tacacacaca tatatgtatg | 1860 |
| tatgtatatg tgtgcatgta tatgtatatg tatatgtgta tgtgtatgtg tatgtgtgtg | 1920 |
| tgtgtgtgtg tgtgtgtgtg tgtgtgtgta tgtgtatgtg tatatgtata tgtatatgta | 1980 |
| tatgtatatg tatatgtata tgtataatgt atatgtatat gtacatgaat gaaaggatgc | 2040 |
| aatcgcagtg atgtcattgg agctgaagta acccttcgct ttccaggtga tcaaatgcaa | 2100 |
| agctgcggtg ctatgggagc ttcacaaacc cttcaccatc gaggacatag aagtcgcacc | 2160 |
| ccccaaggcc catgaagttc gaattaaggt gactgcccct ttcaacttct gcaaagttag | 2220 |

```
gttggaaaaa ctcgaaaagt actccatagc cacatccaga aatccgttaa tagccccttt    2280
catgtgctta attaatttgc tgctatcaat atcaaatgtc caaagtttga agtgactaga    2340
aagtatgttt aacctaatct cagaattttc tttagatgct tatgtgttta tgaagtgcta    2400
aaacatcttg agtccaaaac caactcatgt tgggtaatgt cttggtgcta atgtttgatt    2460
tctatttgca taaagcagca tgcattttca tatattccat aaaacacatt ttcagagcca    2520
cctactctac aggattgata attgagccat ttaattggga aaaggtaaac ggaaacactg    2580
gagaatcttg gagataaatg aactctttgg aatttggaag cagtaaggat tgttaggaag    2640
cccctcagaa gcacgactgc agacgaatag gcttgtgaaa cctccacaat cacaaacttg    2700
gttaactgga ctttacccttt aatccacaga tggtggccac tggtgtctgc cgctcagacg    2760
atcacgtggt tagtggaacc ctggtcacac ctcttcctgc agttttaggc catgagggag    2820
caggcattgt tgagagcgtt ggagaagggg tgacttgtgt gaaaccaggt acagaattca    2880
ccctcagggc ttgtgtttcg gttctgatct caagagcatc cctcccaaga gaggaagttg    2940
aggaagtggg agatgaaaag ccaggcaata aaggcttcc tctgccccttt cctcccggca    3000 tgcctcagtc gtgctacatc caagcaagtc ttttctcttt caacatctgt ttatctccta    3060
catgtcaggc atcaagccag aggctcctat atgaagatct ggaagcacgg tgcccgtaag    3120
ggtgtgcagt ttataatctg ctaacttcta ctttattgtc cctgagcgct gtggactttc    3180
aaaacccaga cagaccttaa aaagtatccg aggcgggaaa tgcaggtcca ggttctgaga    3240
tacacggcag ctgttctgtg ctgaacgcag agacgtgaag gcttgcccta ctcgcaggac    3300
gcccaccata gttttaacca cacactggga caacatgatg gcttcctctt ttcctgtatg    3360
ctccttcttt atgaatatag ataaaataaa atgtaagagg gaatataagg gaaaatcata    3420
gccaaaggcc ttcaaaccca cagaccttct tatcattaat tgtggctgta ggtggtaggt    3480
cacacagtat ttattgcgtt acacatggct ccactttata tgttttttaag gtaaagggtg    3540 agcaaaacat aaaatttccg tgataccatc ccacattaat tttatctatg aaatataatg    3600
accaaacctt ttttttttggt ccaataacat aggtagcata catgatttaa aaacaaaaat    3660
tatgttcatc ttcaaaaaga tcgctttagt caatagagtc agacttctct tctaaatgac    3720
taagctgtaa gcaaaaaata ggaaaagaac taatctggtt tgagttaagc ttgtattatt    3780
tcttttattc agaaaagaac aaaacaacaa caacaaacct agcagcaaaa tgacacctt    3840 actcttcagg ttgcttcttc tatggcagaa aaatcaataa ttcataaata attatcttta    3900
aaaaacaaaa gtttcttgtt atttcccaga gaaagtattt aactcattaa gaactgagat    3960
ttccaaagca atttgtggct tgtcatgttt ttattatgct tcctcaaaaa ataactaaga    4020
ttttttaagc ctttatttca tagtaggaga agcacaatca ccttaaaaag ccaaaactgg    4080
accacgaaga aatgataacg tggctcaggg cataccatgc tcttatagag cacccaactg    4140
ggttactcac aaccacttgt aactccagct cctggggacc caacacccttt tgctggcttc    4200 caagggcaca catacagaga tggcacacac acacaggtac tctcacatgc acacaaaaag    4260
aaaaaaacca acaccaacaa caaagtctta aacaataaaa gggcaaaagc taactatcaa    4320
gattcccact ttaatttgat ttcatgatca agtttaattt gttttatttt tactataaaa    4380
tattgcctgt atagtgtttc tttaatctta cttttattga aactatcata tcagttctcg    4440
ccaaaatcta acaggaagat agcaactcat ttgcagagaa agtgtatatt tcttcttagc    4500
agcaagcata tccaaggttt gattaggata tgtacaaagc tcctaagaga aactgaggca    4560
```

```
cacaacaaag tttaactgct gacgggtgga aatggctggt ttcggctcat ttttctctcc   4620
cgggaatctt caggcgcttt aaatgcgaat gactaattag actgacatag cctgggtgag   4680
gcctcatctc ctggagactt ttcaaagaca caatgtctct aataagcttc aagttgttgc   4740
tttattgatt tctggacaga catttaagtc attttgtttt tcttcatcca ggtgataaag   4800
tcattccact cttttcccct cagtgtggag aatgcaggat ttgcaagcac ccggaaagca   4860
acttttgtag ccgaagcgag tacgtttctt attgtcttct tgcacagttg ggtgggcaca   4920
ctgctttgtt ctgtctcatg tcctttgtat gcctgtgttt caccaaccag tctgctaatg   4980
cctcggggga ctttgcgcga aggcaccagc aggttctcct gcaagggaaa gcagatccac   5040
aactttatca gcaccagcac cttctcccag tacaccgtgg tagatgatat agcagtggcc   5100
aaaatcgatg gagcttcacc actgacaaaa gtctgcctca tcggctgtgg gttctcaact   5160
ggctatggct ctgccgtcaa agtcgccaag gtaggatgga cagtgggcca tggaacaagc   5220
taagtgcata ttattggtac ctaaagggaa gacatggctc ctgggcgggc atcagagtat   5280
ttttgtagaa gtgaaataag cctctccagc cccagtgaga attcactcca cacacttgag   5340
agaagcaagg gaaagctcta taatagtgtg tgtctagttc tagctcttgc ccaaagagaa   5400
accagcgtct aacagaaatt atttgaagtt tgtttaggtc ttgggctgta acattctaca   5460
tatgccattg tctgcagatc tctgttatgt cccagctgca agactcactg agcaatgaaa   5520
tacattttaa ggagacagaa actggaaagc ttgactatat tggacaaatg ggagatttta   5580
taaagtggag atgccatcac tgttatttct aaagcaagcc acaatgggga tatttgtact   5640
gcagagatag tgccacaagt gtgcgttagt ttgtttttaa gtagaccaac attgttacct   5700
agagccgtcc tgccttccag gtagaatttt ctagataaga aaccaaggc ttttaatagc   5760 agagtagtac tccattgtgt agatgtacca cattttctgt atctatccat tcctctgttg   5820
aaagacatct gggttctttc cagcttctgg ctattataaa taaggctgtt atgaacatag   5880
tggagcatgt gtccttgtta tatgttggag catcttctgt gtatatgccc aggagtatat   5940
gctgagtcct catgtcaaat ttctgaggaa ccaacagact gatttccaga gtggttgtaa   6000
tcctaccaac aatggaggaa tgtgcctctt tctcccacatc ctcaccagca tctgctgaaa   6060
ttcttaggca aatggatgga actagaaaat atcatcctga atgaggtaac ccaatcacaa   6120
aagaacacac atagtatgca ttcactaata agtggggata ttagccgcaa agcatggaat   6180
actcaagata caattcacag atcacataaa gctcaagaag aaggagacct aagtgtgggt   6240
ccttcttaga aaggggaaca aaagactgtt ggaagccaat atagagatga agcataaagc   6300
agaggctgaa ggaaggtcat ccagagaatt cactccacac atgccccact tggggatcca   6360
tcccaaatac agtcaccaaa gccagacact attgtagatg ccaagaagtg catgctgaca   6420
ggagcatgat acagctgtct cctgagaggc cctgccagag ccttacaaat acagatgcag   6480
atgctcaaag ccaaccattg gactgagagc agggccccaa atggaggatt tagagaaaga   6540
acttaaggag ccgaagggac taagacacca accaaagagt acacatggag ggacccatgg   6600
ctcagcctta tatgtaacag aggttggtct tgtcaggcat caatgggagg agaggttctt   6660
ggtcctgtga aggctcgata gatgcccag tgtaggagaa tgccagggtg gtgaggtggg   6720
agtgggtggg tgggtgaagg aacaccctca tagaagcagg gggaggggga gtagtataga   6780
gggtttctag aagtggggga aactggaaag ggggataata tttgaaatgt aaataaagga   6840
aatatccaat taaaaaatcc ttacatttaa aaaaagaaa gaaaaccaag cttaatgat    6900 ggaccaggat ttaatggtac catgacccag tgcagcattg tgagctgcct gacagaggca   6960
```

```
tgctctttga taatgggaag agcctagtgg ccagctgtgg gctgtggttg tctctgtttg    7020
ttaacatatt catgatgtca gaggcatgcc ttttcctata gtttctgaca agcctgccta    7080
gtgtgttggt cttccttaac tcatgcaagc gacaacacca ggttagctaa actctacttt    7140
gtgtgatata atatttccta agcaagttca ttagtagatc cttcaagaca tcaatttatc    7200
actctaggat tctcctatgt cacttcatag atttatggtt ttgaattatt aatagaaaaa    7260
taaccccaga tggaactgga aaaaagaaa attcatcttt tttttaaaga tgaaaattat    7320
gctgattctg aattaagaaa aagtaaatat ttataaatat aataaatatt tataataaat    7380
ataatacatg tagaagatat tataatctgt gtattctata tgactaccaa aatttaaagc    7440
tgggaactct tgtagtagcc tattctccag ttgaaaagag atgtcactca tccatcatga    7500
tgggttccgc taggttctca agtagccaaa gcaaacggtt tgtcttctcc cagccttacc    7560
tgattcatct gcagcatggc cacccactga gtggatccca aagactcaa gagaacttaa    7620 gcaaagtatt gattacattt gagacctcat cactacatct tttcccttgc aaccaaaaca    7680
cacaaacaca cacacacaca aatacacata cgcatacaaa cacacatatg catacaaaca    7740
caaacagaaa catacacaca aacacactca taaccaacac acacacacac actagaagtt    7800
ttagatgttt agttttagac attttagatg gcgattttaa aaataaattc cttcccaaat    7860
ggttgaaaca aatccagtag ttatctttca ttttatgaaa actaaaatcc aggaagctaa    7920
agctaaaact attcatctaa attttcacta gggaaataaa gactagaatt cctctcaact    7980
tctctgctgc atctgaaact agagtgcaca ctggtcatga ctcccatcac agtaacaggc    8040
cttgcatttt tctgggccag gtggagagtg gcgatgtgtc ccagagcatt taagagcatt    8100
tgatggatga atgacaagat agacaccact aggggaagt gacagtcggg tatgggacac    8160
aggtggctgc accaattaaa tagacctaag ccagtcacag taatgaggag cctgccttt    8220 ccaattctga ggctttagac ctaaatgcaa ttcgtgcttg tgctgttgtt taactgtctc    8280
agctggaagg ccgagtgtgc ctatttgcaa gccaagggta gttgtaatca tggattttaa    8340
ttaatcgtga ctaaaataca gattagcttt tgttgaagta tttgtcattt gcttcttcta    8400
aacattcagg cataaagtct cacagagatt acattggtct catgctatct tgtcttaaag    8460
tttcgtgtcc actttcctat tgctttaagc caggtatgac ttctacatgc ttctcagccg    8520
acttctgctc ccagtaccgt agttgtgact actgaaagtt agtgaaccaa gaaggagtt    8580 cacgagcaaa gggcagttgg gttacctttt agtctcctgg agtaaccttg atcacttgtt    8640
tcatttattc aaattgctta tgtgcgtgtg taagatgtta ttgtaaagct ctcaaagatg    8700
taagtcgttt ttatttagaa ttcaaagatc atctggtaca gctgatctca acttgagttt    8760
tccccattga aataggaatg aggttccatt tgcagtgatt ccaattaat tggtagaagc    8820 tgctatcaga ccttgagatt aacgaaagaa atccccagat atgtctaata catagcaaat    8880
cttgagtacc aatgatgtac actttgggca accataacca gaagtggatt tggcaacaaa    8940
tggaatgagg tagccgtgat aaaggacaca gcaaggcaat atgtgcagtg gggagcaccc    9000
cctaacagtc accattcaat ccacttttgt attttctgga aatacaggtg accccaggct    9060
ccacatgtgc cgtgtttggc ctcggaggtg tcggtctgtc tgtcatcatt ggctgtaaag    9120
cagcaggagc agccaggatc attgctgtgg acatcaacaa ggacaagttt gccaaggcca    9180
aagagttggg tgcaactgag tgcatcaacc ctcaagacta cagcaaaccc atccaggaag    9240
ttctccagga gatgaccgac ggaggggtgg acttttcgtt tgaagtcatc ggccgccttg    9300
```

```
acaccatggt atgtactttg gcacgccttg agatctgtcc ttccatctag aatgctctag   9360
gtagactaac agaaatctca tgcagaaagc tattttaga gtggtcatct tccatctcct   9420
gtttcctgct cagactgctt aattcgctgt tgagataaac ctttcatttt gtcagttctg   9480
caaacttgtc tcaagtgcta atcctccttt aatgcaacga agctttcaat ggggacactg   9540
tgaattaact tactgatttt ctgtaaaaaa tcacttcatc gagcaggttt aaatacaaag   9600
tctggtctta aatggatgaa tatgattttc tccctcattc ttaatatttt ttaatattta   9660
gaattgaata ttctgaaaag catttttaag tatcatcata cggccaaaag gaataatgaa   9720
caatttgggg cccaaggatc attttattaa cacacaacac gtagagggaa gtgactgatt   9780
tatacatcac catttagttc tcgttgcaga gacagcacag ggctgggcct tccaagcttc   9840
cagatctacc ggttgtagta aatacctttt aaaaaagaa ttctggcata tctcctaaat   9900
ttaagagata cattttatag gattgcttat gatctccaca agacagtgca tataaaatac   9960
taactgtaga gcccctgcca tgtggtaagc actcagtaaa ggtcagctga ggataatgat  10020
aagaaatact acggtcaagc ttagagcgat tggattttgg agtacaaatg acactacagt  10080
caagtagtta caaatgtcat cctttgctaa agaactgttc tccggttaca tctcacctaa  10140
ccaaagacct ctagaactct actgagaaat gtccccaggg agcaaggaag tcaccattat  10200
caaggctctc cacaaagtct tggcagagtt ggtgctggat aataggtatg gcgccctgag  10260
agtgatggtt tggtttagtt ttttttccat ccttgaactg tgacaagatg ccatagactg  10320
tagaagattc aagtgcacag cacctcctct ttccaaaccc aggcttccag ctctccccag  10380
agccactgct ctcgtggctc actggtagat ttctcaatct gctcatctta agctgggctg  10440
tcaattgact tgaagatcca aaagtctgat aaccacatgt tctgaggata tctggtttct  10500
aaacatcata ttgcaaaatc aaaggccact catgtatctt taaggattcc aaatgatttt  10560
ttactagaga atgtgtttta acaaacaaa caaaaaacca aacaaactaa agaaaagtac  10620
ctattggaag gcaaaaactt cctggatgtc tacagctata gaataatata aaactatcgc  10680
ataaccactt aaaacatgcc cattcttgat gtaagcaccc gaggagggac tcattaaatg  10740
agaatttgac aaaatggttaa aagataagtt ttgatgatgt catcatttat cttcttcacc  10800
attagatttc tggctcagag tactagttta gaaattgtcc ttactgggca aatgaaaagt  10860
gaactaagca gttcatagag agttatgcga tggggaaaca atattctcct ttgagaacca  10920
gactttactt tctcatgatg attcttgcac ctttaaggaa gaattaaaca tagataagtt  10980
aattcattca ctctttcatt aaaaaagaa aaaatcttc agtgtacttc tttgtaatgc  11040
ctgaaactgc atagtgagga gagaccacaa aagactctac tttaactatt actctttatt  11100
ccagacttct gccctgctga gctgccatgc agcatgtggt gtaagcgtcg tcgtaggagt  11160
gcctcccaat gcccagaacc tctccatgaa ccccatgttg ctgctgctgg gacgcacctg  11220
gaagggagca atatttggcg gtatgtattc acagctcaag atcaatcctg catctgtctg  11280
tatacgtcag ggcgggcgtg tggatgtgtg tgtggaggac agagaacatt cgattcatta  11340
cctgggagcc atttgccacg ttctttgtga cagggtgtca cagtgaccag gctagccttg  11400
ctggctggaa tccactggtt ccctttatcc agagctggaa ttacaagaac tcccacaacc  11460
acatcagctg ttggttggtt ggttggttgg ttggttggtc agttgttgtt ttgttattca  11520
aactcaggtt tgactgagcc atctcctcag ctttgaggat caaattttta atgtatttca  11580
gaatttcttc ccttctgtta cagagaaggt cagattttag aaggcaaaac aatttaaaaa  11640
catgaaaatt actgttctct ctaagcaaga actaatgcag gaaattgtaa gacaagcttc  11700
```

```
attgtgtccc cataaactag ccagggcttc ttctggctcc tcctacttcc taatgtcatt   11760
gtgagagccc caaaatgcct tataggacac aggaaatcca aggcagtagt agtccatgcc   11820
tataatcatg acctaagtct gaacagcggt gagaatggca aagctcccct actttgagta   11880
caaacatctt caatatgatt tctctaggaa agaactaata agccaccttc attagcgaga   11940
gatcgcggtt tagaggggtg gcatacgata aaaatgttaa tgaaatgcag aatgtttttg   12000
agcctcagtg tctgtgcagc ctgcagacca ctgttctttt atgaaccttta gtttccctgc   12060 aaagtctggt tggcttgctc ccccgccac tcccccacac attccctccc tccaaccccc   12120
caggctggat ctcatggaga tgttgctctc cttccaggtt taagagtaa agattctgtc   12180 cctaaacttg tggctgactt catggctaag aagtttccgt tggacccgtt aattacccat   12240
gttttacctt tcgagaaaat aaatgaagca tttgacctgc ttcgttctgg aaagaggtaa   12300
gctttgagat tatttttatg gcagaggaat tggctaacag aaaatgaagg agaagtggga   12360
taagaccata aatgaagggg gtgggggaag gggctggctt ctgtcaccag tttggctctg   12420
cacacaggta tatgacatag gacaattgca aacctaagct ttagtttcca cagttcctaa   12480
aggtgacaat atgtgataat ccaccttgta gtattgctgt ttaggatgag gtttaaatga   12540
gataaccatg ccttaaaagc ttccataaag cacatggcag gtagcaagga ggaaatggct   12600
ggtgttgccc attgttacac aagggatcca gacttttagt gttgtttaag agtgctaaac   12660
tagaaccgga atcaaaatgg cagtcacatc aggatgttaa gtgtgagttt agagctggag   12720
agaatgcaag agcgatcaga aaggtggatt gctcgtttac tgacttgacc ttgggcatag   12780
catggttggg aacccggata gattttctca gagactccta acatgtcttc tactcacttt   12840
tatggtgagt tatggaatgt gaaatcacta tcttctgttc tgtatttcag catccgtacc   12900
gtcctgactt tctgagatca tgtggatgcc ttcccacgca ccagtttctg aaccctaaac   12960
cagactgatt caagcaccag ccacatcaca gccttaatct ttgctcttta gagacacagc   13020
caataaagta cttgtgtaag ctctcca                                       13047

<210> SEQ ID NO 15
<211> LENGTH: 2024
<212> TYPE: DNA
<213> ORGANISM: Arabidopsis thaliana

<400> SEQUENCE: 15
tctacttctt ccaattacca gctgctatat aaatcccctt ctctgtttct cttttcttac     60
atcacaatca cacaaaacta acaaaagatc aaaagcaagt tcttcactgt tgataatgtc    120
taccaccgga cagattattc gatgcaaagg ttttcttttt attctgtctt tttccaaata    180
tttattgatc ggttacattt ctgttgaggt ttttgttatg aatccacaat ttctatgttg    240
aattaacaaa acctgtgtcg ttttttttgtg gtggttgcag ctgctgtggc atgggaagcc    300
ggaaagccac tggtgatcga ggaagtggag gttgctccac cgcagaaaca cgaagttcgt    360
atcaagattc tcttcacttc tctctgtcac accgatgttt acttctggga agctaaggta    420
gagtaatcaa tttattacac tccaaattca taatcaagtt ctaattttt tagaattcta    480 attttttatc taaaaaaatt caacctttt gattccacag gacaaacac cgttgtttcc    540 acgtatcttc ggccatgaag ctggagggta atagaaacac taatcttctt tgcttcgttt    600
tggatatttt taaggtttta gagattcaag gtcgtttttt ttgttgttgt gtaggattgt    660
tgagagtgtt ggagaaggag tgactgatct tcagccagga gatcatgtgt tgccgatctt    720
```

| | | | | |
|---|---|---|---|---|
| taccggagaa | tgtggggagt | gtcgtcattg | ccactcggag | gaatcaaaca tgtgtgatct | 780 |
| tctcaggatc | aacaccgagc | gaggagggat | gattcacgat | ggtgaatcaa gattctccat | 840 |
| taatggcaaa | ccaatttacc | atttccttgg | gacttccacg | ttcagtgagt acacagtggt | 900 |
| tcactctggt | caggttgcta | agatcaatcc | ggatgctcct | cttgacaagg tctgtattgt | 960 |
| cagttgtggt | ttgtctactg | ggttaggagc | aactttgaat | gtggctaaac ccaagaaagg | 1020 |
| tcaaagtgtt | gccattttg | gtcttggtgc | tgttggttta | ggcgctgcag aaggtgctag | 1080 |
| aatcgctggt | gcttctagga | tcatcggtgt | tgattttaac | tctaaaagat tcgaccaagg | 1140 |
| tattcaaaaa | gatgatagtc | tgttttgac | tatgttcttc | tataatctcc cttcacttac | 1200 |
| attgaatttg | atatgttatt | ggcagctaag | gaattcggtg | tgaccgagtg tgtgaacccg | 1260 |
| aaagaccatg | acaagccaat | tcaacaggta | atcgctgaga | tgacggatgg tggggtggac | 1320 |
| aggagtgtgg | aatgcaccgg | aagcgttcag | gccatgattc | aagcatttga atgtgtccac | 1380 |
| gatgtaatcc | tcccttcaca | tcattcggac | caaaactttt | gtaactacat tgtgggtatc | 1440 |
| tgaacttatc | acatatgatg | ttgtttcagg | gctggggtgt | tgcagtgctg gtgggtgtgc | 1500 |
| caagcaaaga | cgatgccttc | aagactcatc | cgatgaattt | cttgaatgag aggactctta | 1560 |
| agggtacttt | cttcgggaac | tacaaaccca | aaactgacat | tcccggggtt gtggaaaagt | 1620 |
| acatgaacaa | ggtaatgaga | agctttgata | tcttatgatg | ccaactttga atatatatca | 1680 |
| atgttctgat | gattttatg | acataggagc | tggagcttga | gaaattcatc actcacacag | 1740 |
| tgccattctc | ggaaatcaac | aaggcctttg | attacatgct | gaagggagag agtattcgtt | 1800 |
| gcatcatcac | catgggtgct | tgaagccatt | ctctcgcaga | tgatgttcac tttgtgtttt | 1860 |
| acttccttta | tgcattcaca | gcaataaaag | aaagaaatct | ccatcgcttt tggttttctt | 1920 |
| ctctgtctta | agttagtcgt | tttcgtgtct | aatctattac | ttatcattgt aatagactct | 1980 |
| tcttctattg | agatttgaat | ataaactaaa | acacattcca | tttt | 2024 |

<210> SEQ ID NO 16
<211> LENGTH: 1445
<212> TYPE: DNA
<213> ORGANISM: Saccharomyces cerevisiae

<400> SEQUENCE: 16

| | | | | |
|---|---|---|---|---|
| aagaaatgat | ggtaaatgaa | ataggaaatc | aaggagcatg | aaggcaaaag acaaatataa | 60 |
| gggtcgaacg | aaaaataaag | tgaaaagtgt | tgatatgatg | tatttggctt tgcggcgccg | 120 |
| aaaaaacgag | tttacgcaat | tgcacaatca | tgctgactct | gtggcggacc cgcgctcttg | 180 |
| ccggcccggc | gataacgctg | ggcgtgaggc | tgtgcccggc | ggagtttttt gcgcctgcat | 240 |
| tttccaaggt | ttaccctgcg | ctaaggggcg | agattggaga | agcaataaga atgccggttg | 300 |
| gggttgcgat | gatgacgacc | acgacaactg | gtgtcattat | ttaagttgcc gaaagaacct | 360 |
| gagtgcattt | gcaacatgag | tatactagaa | gaatgagcca | agacttgcga gacgcgagtt | 420 |
| tgccggtggt | gcgaacaata | gagcgaccat | gaccttgaag | gtgagacgcg cataaccgct | 480 |
| agagtacttt | gaagaggaaa | cagcaatagg | gttgctacca | gtataaatag acaggtacat | 540 |
| acaacactgg | aaatggttgt | ctgtttgagt | acgctttcaa | ttcatttggg tgtgcacttt | 600 |
| attatgttac | aatatggaag | ggaactttac | acttctccta | tgcacatata ttaattaaag | 660 |
| tccaatgcta | gtagagaagg | ggggtaacac | ccctccgcgc | tcttttccga tttttttcta | 720 |
| aaccgtggaa | tatttcggat | atcctttgt | tgttccggg | tgtacaatat ggacttcctc | 780 |
| ttttctggca | accaaaccca | tacatcggga | ttcctataat | accttcgttg gtctccctaa | 840 |

| | | |
|---|---|---|
| catgtaggtg gcggaggggga gatatacaat agaacagata ccagacaaga cataatgggc | 900 |
| taaacaagac tacaccaatt acactgcctc attgatggtg gtacataacg aactaatact | 960 |
| gtagccctag acttgatagc catcatcata tcgaagtttc actacccttt ttccatttgc | 1020 |
| catctattga agtaataata ggcgcatgca acttctttc tttttttttc ttttctctct | 1080 |
| cccccgttgt tgtctcacca tatccgcaat gacaaaaaaa atgatggaag acactaaagg | 1140 |
| aaaaaattaa cgacaaagac agcaccaaca gatgtcgttg ttccagagct gatgaggggt | 1200 |
| atcttcgaac acacgaaact ttttccttcc ttcattcacg cacactactc tctaatgagc | 1260 |
| aacggtatac ggccttcctt ccagttactt gaatttgaaa taaaaaagt ttgccgcttt | 1320 |
| gctatcaagt ataaatagac ctgcaattat taatcttttg tttcctcgtc attgttctcg | 1380 |
| ttcccttct tccttgtttc tttttctgca caatatttca agctataccta agcatacaat | 1440 |
| caact | 1445 |

<210> SEQ ID NO 17
<211> LENGTH: 2655
<212> TYPE: DNA
<213> ORGANISM: Saccharomyces cerevisiae

<400> SEQUENCE: 17

| | | |
|---|---|---|
| atggatccta atagtaacag ttctagcgaa acattacgcc aagagaaaca gggtttccta | 60 |
| gacaaagctc ttcagagggt gaagggcata gcactgcgac gaaacaatag taacaaagat | 120 |
| catacaacag atgatacgac aggtagcata cgaaccccta cgagcttgca gcggcaaaat | 180 |
| tctgacaggc aatctaatat gacatccgtg tttacggatg acatttctac catagacgac | 240 |
| aactcaattt tattttcaga gcctcctcag aaacaatcta tgatgatgtc tatatgcgta | 300 |
| ggtgttttg ttgcagttgg cggattttta tttggttatg atacaggtct gatcaacagt | 360 |
| attacatcta tgaactatgt gaagtcacac gtagcaccta atcacgattc atttaccgcc | 420 |
| caacaaatgt ccattttggt gtcatttttg tcattgggaa cttttttgg ggctttaact | 480 |
| gcaccattta tatctgattc gtatggcagg aagcctacta tcattttcag tacaattttc | 540 |
| atcttctcta tcggaaattc tttacaggta ggtgctggag aatcacatt attgattgtg | 600 |
| ggaagggtca tttcaggtat cggtataggc gcaatttcag cggttgttcc attataccaa | 660 |
| gcagaagcta cacataaatc attaagaggt gctattattt ctacttacca atgggccatt | 720 |
| acctggggct tgctcgtgtc aagtgcagtg tcgcaaggga cacacgcaag aaacgacgca | 780 |
| tcttcgtatc ggattcccat agggttgcaa tatgtctggt cgtcatttct cgctatcggg | 840 |
| atgttctttc tccctgagag tccacgctat tacgttttga agacaagct agatgaagca | 900 |
| gctaaatctt tatcgttttt aagaggtgta ccagtccatg attctgggtt actggaagaa | 960 |
| ctagttgaaa taaaggcaac atatgattac gaggcatctt ttggttcttc gaacttcatt | 1020 |
| gattgtttta tttcaagtaa aagtagacca agcaaactc taaggatgtt tacgggaatt | 1080 |
| gcccttcaag catttcaaca attttcaggt atcaactta tattttacta cggtgtcaat | 1140 |
| ttcttcaata agacaggagt cagtaatagt tatctggttt catttataac ctatgctgtt | 1200 |
| aatgttgtct ttaatgttcc tggtttgttt tttgtggaat tttttggtag acgtaaggtg | 1260 |
| ctggttgttg ggggtgttat catgactata gccaactta ttgtggccat tgttgggtgt | 1320 |
| tccttaaaga ctgtagcggc cgcaaaagtt atgatagcat ttatatgtct attcatagct | 1380 |
| gccttttctg ctacatgggg tggtgttgtt tgggttattt cagcagaact gtacccattg | 1440 |

```
ggtgtgagat ctaaatgtac ggctatatgc gctgctgcta actggcttgt aaactttatt         1500
tgtgctttaa ttaccccta tattgtagat actgggtcgc atacatcatc attaggtgca          1560
aaaatattct tcatttgggg ctccttaaat gcgatggggg tgatagttgt ttacttgacc         1620
gtttatgaaa cgaagggttt gacattagaa gagattgatg aattatatat taagtcatcc        1680
actggtgtcg tgtcaccaaa atttaataaa gatattaggg aacgcgcact taaattccaa        1740
tacgatcctt tgcaaagatt agaagacgga agaacactt ttgttgctaa aagaaataat         1800
tttgacgatg aaacaccaag aaatgatttt cgaaatacga tatcgggcga aatagatcat        1860
agtcccaatc aaaagaagt tcattctatc ccagaacgtg ttgatattcc tactagtaca         1920
gaaattcttg aaagcccgaa caaaagtagt ggtatgacag tccctgtgtc accttctctg        1980
caagacgttc caatcccgca acaacagag cctgctgaaa ttcgaaccaa atatgtggac         2040
ctaggaaatg ggcttggtct taatacgtat aatagagggc ctccctcact ctcaagcgac        2100
tcaagcgaag attacacaga agatgaaata ggcgggccct catctcaagg cgaccaaagt        2160
aatagaagta ctatgaatga tattaatgat tatatgcac gtctcattca cagtacttct         2220
actgcaagta acacgacaga taagttctcc ggtaaccaaa gtaccttcg ttaccacacg         2280 gcttcctcac attcggatac aactgaagag gacagcaatt tgatggacct gggaaacggg        2340
cttgccttga tgcttataa cagaggtcca ccttcaattt taatgaattc cagtgatgaa         2400
gaggcaaatg gtggtgagac gtctgataat ttgaacacag ctcaagactt ggctggtatg        2460
aaggaacgaa tggcgcagtt tgcgcagagc tatattgaca agagaggcgg tctggaacct        2520
gaaactcaat ctaatatttt gagcacttct ctctccgtga tggctgacac taatgaacat        2580
aataatgaaa tcctccactc aagcgaagaa aacgccacta atcaacctgt aaatgaaaat        2640
aatgatttga aataa                                                         2655
```

<210> SEQ ID NO 18
<211> LENGTH: 2655
<212> TYPE: DNA
<213> ORGANISM: Saccharomyces cerevisiae

<400> SEQUENCE: 18

```
atggatccta atagtaacag ttctagcgaa acattacgcc aagagaaaca gggtttccta          60
gacaaagctc ttcagagggt gaagggcata gcactgcgac gaaacaatag taacaaagat        120
catacaacag atgatacgac aggtagcata cgaaccccta cgagcttgca gcggcaaaat        180
tctgacaggc aatctaatat gacatccgtg tttacggatg acatttctac catagacgac        240
aactcaattt tattttcaga gcctcctcag aaacaatcta tgatgatgtc tatatgcgta        300 ggtgttttg ttgcagttgg cggatttta tttggttatg atacaggtct gatcaacagt         360
attacatcta tgaactatgt gaagtcacac gtagcaccta atcacgattc atttaccgcc        420
caacaaatgt ccattttggt gtcattttg tcattgggaa ctttttttgg ggcttttact         480
gcaccattta tatctgattc gtatggcagg aagcctacta tcattttcag tacaattttc        540
atcttctcta tcggaaattc tttacaggta ggtgctggag gaatcacatt attgattgtg       600
ggaagggtca tttcaggtat cggtataggc gcaatttcag cggttgttcc attataccaa       660
gcagaagcta cacataaatc attaagaggt gctattattt ctacttacca atgggccatt       720
acctggggct tgctcgtgtc aagtgcagtg tcgcaaggga cacacgcaag aaacgacgca       780
tcttcgtatc ggattcccat agggttgcaa tatgtctggt cgtcatttct cgctatcggg       840
atgttctttc tccctgagag tccacgctat tacgttttga aagacaagct agatgaagca       900
```

```
gctaaatctt tatcgttttt aagaggtgta ccagtccatg attctgggtt actggaagaa    960
ctagttgaaa taaaggcaac atatgattac gaggcatctt ttggttcttc gaacttcatt   1020
gattgtttta tttcaagtaa aagtagacca aagcaaactc taaggatgtt tacgggaatt   1080
gcccttcaag catttcaaca attttcaggt atcaacttta tattttacta cggtgtcaat   1140
ttcttcaata agacaggagt cagtaatagt tatctggttt catttataac ctatgctgtt   1200
aatgttgtct ttaatgttcc tggtttgttt tttgtggaat tttttggtag acgtaaggtg   1260
ctggttgttg ggggtgttat catgactata gccaacttta ttgtggccat tgttgggtgt   1320
tccttaaaga ctgtagcggc cgcaaaagtt atgatagcat ttatatgtct attcatagct   1380
gccttttctg ctacatgggg tggtgttgtt tgggttattt cagcagaact gtacccattg   1440
ggtgtgagat ctaaatgtac ggctatatgc gctgctgcta actggcttgt aaactttatt   1500
tgtgctttaa ttacccctta tattgtagat actgggtcgc atacatcatc attaggtgca   1560
aaaatattct tcatttgggg ctccttaaat gcgatggggg tgatagttgt ttacttgacc   1620
gtttatgaaa cgaagggttt gacattagaa gagattgatg aattatatat taagtcatcc   1680
actggtgtcg tgtcaccaaa atttaataaa gatattaggg aacgcgcact taaattccaa   1740
tacgatcctt tgcaaagatt agaagacgga aagaacactt tgttgctaa aagaaataat   1800 tttgacgatg aaacaccaag aaatgatttt cgaaatacga tatcgggcga aatagatcat   1860
agtcccaatc aaaaagaagt tcattctatc ccagaacgtg ttgatattcc tactagtaca   1920
gaaattcttg aaagcccgaa caaaagtagt ggtatgacag tccctgtgtc accttctctg   1980
caagacgttc caatcccgca acaacagag cctgctgaaa ttcgaaccaa atatgtggac   2040
ctaggaaatg ggcttggtct taatacgtat aatagagggc ctccctcact ctcaagcgac   2100
tcaagcgaag attacacaga agatgaaata ggcgggccct catctcaagg cgaccaaagt   2160
aatagaagta ctatgaatga tattaatgat tatatggcac gtctcattca cagtacttct   2220
actgcaagta acacgacaga taagttctcc ggtaaccaaa gtacccttcg ttaccacacg   2280
gcttcctcac attcggatac aactgaagag acagcaatt tgatggacct gggaacggg    2340 cttgccttga atgcttataa cagaggtcca ccttcaattt taatgaattc cagtgatgaa   2400
gaggcaaatg gtggtgagac gtctgataat ttgaacacag ctcaagactt ggctggtatg   2460
aaggaacgaa tggcgcagtt tgcgcagagc tatattgaca agagaggcgg tctgaacct    2520 gaaactcaat ctaatatttt gagcacttct ctctccgtga tggctgacac taatgaacat   2580
aataatgaaa tcctccactc aagcgaagaa acgccacta atcaacctgt aaatgaaaat    2640
aatgatttga aataa                                                   2655
```

<210> SEQ ID NO 19
<211> LENGTH: 1581
<212> TYPE: DNA
<213> ORGANISM: Candida albicans

<400> SEQUENCE: 19

```
atgagtgcaa atatccaagc tcttatgaaa agctatgtca attttgacga acacacttct     60
ggttccgctg ccagaggtat tttaatcggt atgtttgctg cttttggtgg gttttttgttt    120 ggttacgaca ctggtactat ttctggtgta ttgtctatgg actacgttaa agccagattc    180
cccaacaaca aaaccgattt cacttctggt gaaagttccc ttattgtctc catttttatca   240 gtcggtactt tgttggttc cttgattgcc ccattgtttt ccgatagaat tggtcgtaga    300
```

```
tggacattga ttttatctac tttgattgtt tttaacttgg gagttctttt acaaactgtt    360
gccactgaaa agaaattgct tattgcaggt agagccattg ccggtactgg tgttggttta    420
atttcatctg ttattcctaa ttatatttcg gaaacaacac caaagtgggc tagaggtgct    480
gtcactgctt cataccaatg gatgatcacc tggggtcttt taattgctgc ttgtgccaac    540
aagggttccc aaggtagaaa agactctggt tcctatagaa tacccattgg tattcaattt    600
ttgtgggcat tgattttggg tattggtttc ttgtttctcc cagaaacccc aagatactgg    660
gtttccaagt ctgaagaaac taaagctaaa gattctttga gaagaattag aaacttgcct    720
gttgatcacc cagatttggt gctggaatac gatgacatta aagcaaactt tgatttcgaa    780
tccaaatatg ccacttcttc ttggacccaa gttttcaaaa acgttaacaa acaacaccac    840
agattattca ctggggttgc catccaagct ttgcaacaac ttactggtat taatttcatc    900
ttctactatg gtactcaatt cttcaagcgt tctggtattg aagatccttt ccttatccaa    960
cttgccacta atattgttaa tgttggtatg actgtgccgg gtattatttt ggttgaaacc   1020
tggggtagaa gaccattgtt gatggccggt agtgttgtta tggctgtctc ccaattgatt   1080
gttgccattg ttggtgttgc tgctagcagt catgctgcaa atcaatgttt agttgctttc   1140
agttgtattt tcattgctgg tttcgcagca acttggggac ctctttgttg ggctatttgt   1200
ggtgaatcct ttgctttgaa cgtgagactg aaatcaatct ccttgtgtac cgcaagtaac   1260
tggctttgga atttcggtat tggttatgct actccttata tggttgattc aggtaaaggg   1320
aacgccgact tgggttcaaa ggtgtttttc atttggggtg gatgtaacgt cattggtggg   1380
ttgtttgcat actttatggt ttacgaaacc aagagtctta cattagaaca agttgatgaa   1440
ttgtacttga agttgatca cgcttggcaa tctaaaggat tgttcctag tgtccacgca   1500 tttagagatg atggcgatat tgagcacatc tcttctgatg gaaaagccga aatggttgaa   1560
gttgatgaaa attccgttta a                                              1581

<210> SEQ ID NO 20
<211> LENGTH: 129
<212> TYPE: DNA
<213> ORGANISM: Artificial sequence
<220> FEATURE:
<223> OTHER INFORMATION: Synthetic construct

<400> SEQUENCE: 20
ccaggcatca aataaaacga aaggctcagt cgaaagactg gcctttcgt tttatctgtt     60 gtttgtcggt gaacgctctc tactagagtc acactggctc accttcgggt gggcctttct    120
gcgtttata                                                            129

<210> SEQ ID NO 21
<211> LENGTH: 76
<212> TYPE: RNA
<213> ORGANISM: Saccharomyces cerevisiae

<400> SEQUENCE: 21
ugcuuaaggc cuaaaacaua ccagaucgcc acccgcgcuu uaaucuggag aggugaauac     60
gaccaccuag gccaaa                                                    76

<210> SEQ ID NO 22
<211> LENGTH: 111
<212> TYPE: DNA
<213> ORGANISM: Ostreococcus tauri

<400> SEQUENCE: 22
```
cgcgcgtcgt gcgagtggct cgatcgatct cacgctcgat cgcgtctgag aacacatcgc    60
tggaacttga ctcaggataa tacctgcgta aggaacgacc gcggcatcgc g            111

<210> SEQ ID NO 23
<211> LENGTH: 1362
<212> TYPE: DNA
<213> ORGANISM: Artificial sequence
<220> FEATURE:
<223> OTHER INFORMATION: Synthetic construct

<400> SEQUENCE: 23
tggctgcgtc tggtgggacc gttgtatacg ccggtagtgg tttgcggggc tacggcgagt    60
tggtcatcat caaacacaac gagacctacg tgagtgccta cggtcacaac cgcaggctgc   120
tggtgcggga agggcaacag gtcaaggtag ggcaatcgat tgccgagatg ggctccacag   180
gaaccgatcg ggtgaagctg cacttcgaga ttcgccgcca gggtaagcct gtcgatccac   240
tgcaatattt gccacgtcgc tgaccgggag ttcgcccgcc cacatcatgt aggtgagcgg   300
gtccgggcgt gtccagcggg aaaggaatcg cccgggcttg agtcgaactc atgcaaggga   360
taacgacatg gcactcaaaa aagaagggcc ggagtttgac cacgatgatg aagtgctcct   420
cctggagccc ggcatcatgc tggacgagtc gtctgccgac gagcagcctt ctccccgggc   480
aactccaaaa gccaccactt ccttctcttc caaacaacac aagcacatcg actacacgcg   540
cgcgttggac gcaacgcagc tgtatctcaa cgaaatcggt ttctcgcccc tgttgacgcc   600
cgaagaggaa gtccacttcg ctcgtctggc gcagaagggc gatcccgctg gtcggaagcg   660
gatgatcgag agcaacctgc ggttggtggt gaagatcgcc cggcgctatg tcaatcgcgg   720
actgtccctg ctcgacctga tcgaggaagg caacctaggc ctgatccgcg ccgtggagaa   780
gttcgatccg gagcgcggat tccggttctc gacctacgcc acctggtgga tccgccagac   840
catcgagcgg gccatcatga accagacccg gaccattcgc ttgccgatcc atgtggtcaa   900
ggagctcaac gtctacctgc gtgcggcgcg ggaactgacc cacaagctcg accacgaacc   960
ttcacccgaa gaaatcgcca acctgctgga gaagccggtc gccgaggtca agcgcatgct  1020
cggcctgaac gaacgggtga cttcggtaga cgtctctctt ggtccggact cggacaagac  1080
cctgctggat acgctcaccg acgatcgccc caccgatccg tgcgagctgc tgcaggatga  1140
cgatctcagc gaaagcagct gacgaactc accgacaagc agcgtgaggt ggtgattcgc  1200
cgcttcggct tgcgcggtca cgaaagcagc acgctggaag aggtcggcca ggaaatcggc  1260
ctgacccgcg agcgggttcg tcagatccag gtcgaggcgc tgaagcgcct gcgggagatt  1320
ctggagaaga atggcctgtc gagtgacgcg ctgttccagt ga                     1362

<210> SEQ ID NO 24
<211> LENGTH: 29
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<222> LOCATION: (13)..(15)
<223> OTHER INFORMATION: n is a, c, g, or t
<220> FEATURE:
<221> NAME/KEY: misc_feature
<222> LOCATION: (18)..(20)
<223> OTHER INFORMATION: n is a, c, g, or t

<400> SEQUENCE: 24

```
<210> SEQ ID NO 25
<211> LENGTH: 18
<212> TYPE: DNA
<213> ORGANISM: Artificial sequence
<220> FEATURE:
<223> OTHER INFORMATION: Synthetic construct

<400> SEQUENCE: 25
cccgccgcca ccatggag                                                    18

<210> SEQ ID NO 26
<211> LENGTH: 13
<212> TYPE: DNA
<213> ORGANISM: Artificial sequence
<220> FEATURE:
<223> OTHER INFORMATION: Synthetic construct

<400> SEQUENCE: 26
tcacacagga aag                                                         13

<210> SEQ ID NO 27
<211> LENGTH: 979
<212> TYPE: DNA
<213> ORGANISM: Artificial sequence
<220> FEATURE:
<223> OTHER INFORMATION: Synthetic construct

<400> SEQUENCE: 27
tccctatcag tgatagagat tgacatccct atcagtgata gagatactga gcactactag      60
agaaagagga gaaatactag atggtgagca agggcgagga gctgttcacc ggggtggtgc     120
ccatcctggt cgagctggac ggcgacgtga acggccacaa gttcagcgtg tccggcgagg     180
gcgagggcga tgccacctac ggcaagctga ccctgaagtt catctgcacc accggcaagc     240
tgcccgtgcc ctggcccacc ctcgtgacca ccctgacctg gggcgtgcag tgcttcagcc     300
gctaccccga ccacatgaag cagcacgact tcttcaagtc cgccatgccc gaaggctacg     360
tccaggagcg caccatcttc ttcaaggacg acggcaacta caagacccgc gccgaggtga     420
agttcgaggg cgacaccctg gtgaaccgca tcgagctgaa gggcatcgac ttcaaggagg     480
acggcaacat cctggggcac aagctggagt acaactacaa cagccacaac gtctatatca     540
ccgccgacaa gcagaagaac ggcatcaagg ccaacttcaa gatccgccac aacatcgagg     600
acggcagcgt gcagctcgcc gaccactacc agcagaacac ccccatcggc gacggccccg     660
tgctgctgcc cgacaaccac tacctgagca cccagtccgc cctgagcaaa gaccccaacg     720
agaagcgcga tcacatggtc ctgctggagt tcgtgaccgc cgccgggatc actctcggca     780
tggacgagct gtacaagagg cctgctgcaa acgacgaaaa ctacgcttta gtagcttaat     840
aatactagag ccaggcatca aataaaacga aaggctcagt cgaaagactg gcctttcgt     900 tttatctgtt gtttgtcggt gaacgctctc tactagagtc acactggctc accttcgggt     960
gggcctttct gcgtttata                                                  979
```